US006399761B1

(12) United States Patent
Miller et al.

(10) Patent No.: US 6,399,761 B1
(45) Date of Patent: Jun. 4, 2002

(54) NUCLEIC ACID ENCODING HUMAN POTASSIUM CHANNEL K+ NOV1 PROTEIN

(75) Inventors: Andrew P. Miller, San Mateo, CA (US); Ping Hu, Bethesda, MD (US); Mark Edward Curran, Raleigh, NC (US); Marc Rutter; Wang Jiang-Yang, both of San Diego, CA (US)

(73) Assignee: ICAgen, Inc., Durham, NC (US)

( * ) Notice: Subject to any disclaimer, the term of this patent is extended or adjusted under 35 U.S.C. 154(b) by 0 days.

(21) Appl. No.: 09/336,643

(22) Filed: Jun. 18, 1999

Related U.S. Application Data
(60) Provisional application No. 60/116,448, filed on Jan. 19, 1999, and provisional application No. 60/095,836, filed on Aug. 7, 1998.

(51) Int. Cl.[7] ............ C12N 15/12; C12N 15/63; C07K 14/705
(52) U.S. Cl. ............ 536/23.5; 435/69.1; 435/252.3; 435/254.11; 435/320.1; 435/325; 435/471; 435/71.1; 435/71.2; 530/350
(58) Field of Search ............... 536/23.1, 23.5, 536/24.3, 24.31; 530/350; 435/69.1, 252.3, 254.11, 320.1, 325, 471, 71.1, 71.2

(56) References Cited

FOREIGN PATENT DOCUMENTS
| EP | 0922763 A1 | 6/1999 |
| EP | 0930364 A1 | 7/1999 |

OTHER PUBLICATIONS

Mikayama et al. Natl. Acad. Sci. USA vol. 90, pp. 10056–10060, 1993.*
Voet et al. Biochemistry. John Wiley & Sons, Inc. pp. 126–128 and 228–234, 1990.*
Derst et al. Genomics, vol. 54, pp. 560–563, 1993.*
Partiseti et al., Cloning and characterization of a novel human inwardly rectifying potassium channel predominantly expressed in small intestine, *FEBS Letters* 434:171–176 (1998).

GenBank Accession No. AB022697, Aug. 31, 1999.
GenBank Accession No. AB022696, Aug. 31, 1999.
GenBank Accession No. AB033108.1, Nov. 11, 1999.
GenBank Accession No. AJ007557, Sep. 24, 1998.
GenBank Accession No.AF061118, May 4, 1998.
GenBank Accession No. ABO13889, Nov. 10, 1998.
GenBank Accession No. AJ006128, Nov. 17, 1998.
GenBank Accession No. AJ006129, Nov. 17, 1998.
GenBank Accession No. ABO13890, Nov. 10, 1999.
GenBank Accession No. AF200713, Nov. 23, 1999.
GenBank Accession No. NM_002252, Mar. 19, 1999.
GenBank Accession No. AF209723, Jan. 3, 2000.
Gen Bank Accession No. Y17607, Sep. 7, 1998.
GenBank Accession No. AFO29056 Jan. 6, 1998.
GenBank Accession No. AF167082, Dec. 20, 1999.
GenBank Accession No. MAU62810, Aug. 24, 1996.
GenBank Accession No. X98564, Jul. 23, 1997.
GenBank Accession No. NM_004979, Sep. 30, 1999.
GenBank Accession No. AF110522, May 11, 1999.
GenBank Accession No. AB032970, Nov. 11, 1999.
GenBank Accession No. NM_008436.1, Jan. 4, 2000.
GenBank Accession No. AF139471, Dec. 17, 1999.
GenBank Accession No. AF129399.1 Aug. 9, 1999.
GenBank Accession No. AF004711, Jan. 5, 1999.
GenBank Accession No. NM_004823, May 7, 1999.
GenBank Accession No. AF134149.1, Jun. 14, 1999.

* cited by examiner

*Primary Examiner*—Prema Mertz
(74) *Attorney, Agent, or Firm*—Townsend and Townsend and Crew LLP

(57) ABSTRACT

Methods for isolating K+Hnov genes are provided. The K+Hnov nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

6 Claims, No Drawings

SEQUENCE LISTING

<160> NUMBER OF SEQ ID NOS: 87

<210> SEQ ID NO 1
<211> LENGTH: 2932
<212> TYPE: DNA
<213> ORGANISM: H. sapiens
<220> FEATURE:
<221> NAME/KEY: CDS
<222> LOCATION: (103)...(1180)
<223> OTHER INFORMATION: K+Hnov1

<400> SEQUENCE: 1

```
attaaaatta tctgatcaaa aaggcagact ctgtaaattt ccttaagacc t accttggca      60 taaaggctga cccagcaaaa gaactgagaa atacagcctg ag atg ga c agc agt        114
                                                  Met Asp Ser Ser
                                                    1 aat tgc aaa gtt att gct cct ctc cta agt c aa aga tac cgg agg atg       162
Asn Cys Lys Val Ile Ala Pro Leu Leu Ser G ln Arg Tyr Arg Arg Met
 5                  10                  15                  20 gtc acc aag gat ggc cac agc aca ctt caa a tg gat ggc gct caa aga       210
Val Thr Lys Asp Gly His Ser Thr Leu Gln M et Asp Gly Ala Gln Arg
                 25                  30                  35 ggt ctt gca tat ctt cga gat gct tgg gga a tc cta atg gac atg cgc       258
Gly Leu Ala Tyr Leu Arg Asp Ala Trp Gly I le Leu Met Asp Met Arg
             40                  45                  50 tgg cgt tgg atg atg ttg gtc ttt tct gct t ct ttt gtt gtc cac tgg       306
Trp Arg Trp Met Met Leu Val Phe Ser Ala S er Phe Val Val His Trp
         55                  60                  65 ctt gtc ttt gca gtg ctc tgg tat gtt ctg g ct gag atg aat ggt gat       354
Leu Val Phe Ala Val Leu Trp Tyr Val Leu A la Glu Met Asn Gly Asp
     70                  75                  80 ctg gaa cta gat cat gat gcc cca cct gaa a ac cac act atc tgt gtc       402
Leu Glu Leu Asp His Asp Ala Pro Pro Glu A sn His Thr Ile Cys Val
 85                  90                  95                 100 aag tat atc acc agt ttc aca gct gca ttc t cc ttc tcc ctg gag aca       450
Lys Tyr Ile Thr Ser Phe Thr Ala Ala Phe S er Phe Ser Leu Glu Thr
                105                 110                 115 caa ctc aca att ggt tat ggt acc atg ttc c cc agt ggt gac tgt cca       498
Gln Leu Thr Ile Gly Tyr Gly Thr Met Phe P ro Ser Gly Asp Cys Pro
```

-continued

```
                  120                 125                 130
agt gca atc gcc tta ctt gcc ata caa atg c tc cta ggc ctc atg cta       546
Ser Ala Ile Ala Leu Leu Ala Ile Gln Met L eu Leu Gly Leu Met Leu
            135                 140                 145 gag gct ttt atc aca ggt gct ttt gtg gcg a ag att gcc cgg cca aaa       594
Glu Ala Phe Ile Thr Gly Ala Phe Val Ala L ys Ile Ala Arg Pro Lys
150                 155                 160 aat cga gct ttt tca att cgc ttt act gac a ca gca gta gta gct cac       642
Asn Arg Ala Phe Ser Ile Arg Phe Thr Asp T hr Ala Val Val Ala His
165                 170                 175                 180 atg gat ggc aaa cct aat ctt atc ttc caa g tg gcc aac acc cga cct       690
Met Asp Gly Lys Pro Asn Leu Ile Phe Gln V al Ala Asn Thr Arg Pro
                185                 190                 195 agc cct cta acc agt gtc cgg gtc tca gct g ta ctc tat cag gaa aga       738
Ser Pro Leu Thr Ser Val Arg Val Ser Ala V al Leu Tyr Gln Glu Arg
            200                 205                 210 gaa aat ggc aaa ctc tac cag acc agt gtg g at ttc cac ctt gat ggc       786
Glu Asn Gly Lys Leu Tyr Gln Thr Ser Val A sp Phe His Leu Asp Gly
            215                 220                 225 atc agt tct gac gaa tgt cca ttc ttc atc t tt cca cta acg tac tat       834
Ile Ser Ser Asp Glu Cys Pro Phe Phe Ile P he Pro Leu Thr Tyr Tyr
        230                 235                 240 cac tcc att aca cca tca agt cct ctg gct a ct ctg ctc cag cat gaa       882
His Ser Ile Thr Pro Ser Ser Pro Leu Ala T hr Leu Leu Gln His Glu
245                 250                 255                 260 aat cct tct cac ttt gaa tta gtt gta ttc c tt tca gca atg cag gag       930
Asn Pro Ser His Phe Glu Leu Val Val Phe L eu Ser Ala Met Gln Glu
                265                 270                 275 ggc act gga gaa ata tgc caa agg agg aca t cc tac cta ccg tct gaa       978
Gly Thr Gly Glu Ile Cys Gln Arg Arg Thr S er Tyr Leu Pro Ser Glu
            280                 285                 290 atc atg tta cat cac tgt ttt gca tct ctg t tg acc cga ggt tcc aaa      1026
Ile Met Leu His His Cys Phe Ala Ser Leu L eu Thr Arg Gly Ser Lys
            295                 300                 305 ggt gaa tat caa atc aag atg gag aat ttt g ac aag act gtc cct gaa      1074
Gly Glu Tyr Gln Ile Lys Met Glu Asn Phe A sp Lys Thr Val Pro Glu
        310                 315                 320 ttt cca act cct ctg gtt tct aaa agc cca a ac agg act gac ctg gat      1122
Phe Pro Thr Pro Leu Val Ser Lys Ser Pro A sn Arg Thr Asp Leu Asp
325                 330                 335                 340 atc cac atc aat gga caa agc att gac aat t tt cag atc tct gaa aca      1170
Ile His Ile Asn Gly Gln Ser Ile Asp Asn P he Gln Ile Ser Glu Thr
                345                 350                 355 gga ctg aca g aataagactt atccattttt taatgtatta aat acaccca            1220
Gly Leu Thr gccagttatg cagctacttt ttctttactg tatctcatgt tttcttttttt c aatgctaat   1280 tatagctctc tacatcacgg taatcatgcc tatgcctaca taagaatggc t gagctaaca    1340 atacacattc tggaaacata acactctaca ttacaaagtt tgttacctgc t gaaatcaat    1400 gtaactcaac ttgacagaca cttatacaga aatgttgctg gtgaatttat a agaatgtgg    1460 tatgatacta gtaatgaagg caaaatggac agtgaagttt aacacaactg a actctaaga   1520 aaatcaacca ttaatctctc attttcatct gcaaattgaa gcaacagttt a gtttcaaac   1580 ctagctccct gggtggaatg acgacttcac tatacttagt gaatatcctt t aagagctgg   1640 gattttttc aagacaacaa agatcattca tttggttctt tatactatga a acttgagta    1700 agtattacct ccttaatttt taacaactaa gaacaaaaat taacgagaaa a acaacaaag   1760
```

-continued

```
tacagattta tacataaacc taaaagcatt tgaacatgac acccgaacac a tacatatat    1820 gttcacttat ttgtggcaga aggtgatcag ataagctcca gcccaaatgg a acctgtggg    1880 gtggtatttt gcattgcaag gagacgcaaa attttatttt aaaactgtcc t ccataataa    1940 tcaaacggtg attcatctaa atgacttcta gcaacctaag taaaaacatt c ccctcctat    2000 gtatgattca tttgatcata taaaacatca tgatggctct aattcataaa t acaaaaata    2060 tatttaagtc tttatagata taaagcttta cttagatata acttgagtga g tagggaaaa    2120 aaatctacag tagataaagc aaaagataat taggcaacaa agcattttca a actcaaatt    2180 cctgttttcca acttcaaata gttttttcta taaacacaaa atcagtgttt a ttcaccagt    2240 aggaggttgg actagatgaa ctctattatt tctttctaaa tctaatagtc t ataaaaatt    2300 atgtttcctc tgtttttttat tttatctatg ctaaaatgag ccctttccct t atgtccagt    2360 ttaagatgat catttgcatg atttcattt caataaaaaa aagagaaact g tccttaaaa    2420 caaacaaaa accaaaaaag tcaccctatc aggtttcaaa cagatttgtg g ctgttcttt    2480 tctgaaattt cccttattca ggtttctgtg ggaaaaatga aagattaacc t tccccactg    2540 gtgatgacct aggcaggaat catctcttga aataaatact agctgagtaa a ggcaagcag    2600 gtgtgaagag cagggctcag cagcaagtca cattttttcta ctatttgacc a aaaggaaaa    2660 gaaaataaag aagaactctg gagtggtcta agactgataa tagcagaaga a tatcaagaa    2720 cacagaaact taattattgt gaacttttgc tgtttgaaaa tcttagacat t cattcttaa    2780 gtagaaatca gaccaacaga ttttcccaac ccaagactat tgtaacacat a aagacagca    2840 agaattctta tttctataat aaattaacaa gattcaccta acctttgaaa a taaagtagt    2900 attgaagact taaaaaaaaa aaaaaaaaaa aa                                   2932
```

<210> SEQ ID NO 2
<211> LENGTH: 359
<212> TYPE: PRT
<213> ORGANISM: H. sapiens

<400> SEQUENCE: 2

```
Met Asp Ser Ser Asn Cys Lys Val Ile Ala P ro Leu Leu Ser Gln Arg
  1               5                  10                  15

Tyr Arg Arg Met Val Thr Lys Asp Gly His S er Thr Leu Gln Met Asp
             20                  25                  30

Gly Ala Gln Arg Gly Leu Ala Tyr Leu Arg A sp Ala Trp Gly Ile Leu
         35                  40                  45

Met Asp Met Arg Trp Arg Trp Met Met Leu V al Phe Ser Ala Ser Phe
     50                  55                  60

Val Val His Trp Leu Val Phe Ala Val Leu T rp Tyr Val Leu Ala Glu
 65                  70                  75                  80

Met Asn Gly Asp Leu Glu Leu Asp His Asp A la Pro Pro Glu Asn His
                 85                  90                  95

Thr Ile Cys Val Lys Tyr Ile Thr Ser Phe T hr Ala Ala Phe Ser Phe
            100                 105                 110

Ser Leu Glu Thr Gln Leu Thr Ile Gly Tyr G ly Thr Met Phe Pro Ser
        115                 120                 125

Gly Asp Cys Pro Ser Ala Ile Ala Leu Leu A la Ile Gln Met Leu Leu
    130                 135                 140

Gly Leu Met Leu Glu Ala Phe Ile Thr Gly A la Phe Val Ala Lys Ile
145                 150                 155                 160

Ala Arg Pro Lys Asn Arg Ala Phe Ser Ile A rg Phe Thr Asp Thr Ala
```

```
                165                 170                 175
Val Val Ala His Met Asp Gly Lys Pro Asn L eu Ile Phe Gln Val Ala
                    180                 185                 190

Asn Thr Arg Pro Ser Pro Leu Thr Ser Val A rg Val Ser Ala Val Leu
                195                 200                 205

Tyr Gln Glu Arg Glu Asn Gly Lys Leu Tyr G ln Thr Ser Val Asp Phe
            210                 215                 220

His Leu Asp Gly Ile Ser Ser Asp Glu Cys P ro Phe Phe Ile Phe Pro
225                 230                 235                 240

Leu Thr Tyr Tyr His Ser Ile Thr Pro Ser S er Pro Leu Ala Thr Leu
                245                 250                 255

Leu Gln His Glu Asn Pro Ser His Phe Glu L eu Val Val Phe Leu Ser
            260                 265                 270

Ala Met Gln Glu Gly Thr Gly Glu Ile Cys G ln Arg Arg Thr Ser Tyr
        275                 280                 285

Leu Pro Ser Glu Ile Met Leu His His Cys P he Ala Ser Leu Leu Thr
    290                 295                 300

Arg Gly Ser Lys Gly Glu Tyr Gln Ile Lys M et Glu Asn Phe Asp Lys
305                 310                 315                 320

Thr Val Pro Glu Phe Pro Thr Pro Leu Val S er Lys Ser Pro Asn Arg
                325                 330                 335

Thr Asp Leu Asp Ile His Ile Asn Gly Gln S er Ile Asp Asn Phe Gln
            340                 345                 350

Ile Ser Glu Thr Gly Leu Thr
        355

<210> SEQ ID NO 3
<211> LENGTH: 1927
<212> TYPE: DNA
<213> ORGANISM: H. sapiens
<220> FEATURE:
<221> NAME/KEY: CDS
<222> LOCATION: (105)...(1908)
<223> OTHER INFORMATION: K+Hnov4

<400> SEQUENCE: 3 ggagcccgc  agcgcttctt  atgatcagct  cggtgtgtgt  ctcctcctac  c gcgggcgca          60 agtcggggaa  caagcctccg  tccaaaacat  gtctgaagga  ggag atg gcc aag ggc         116
                                                    Met Ala Lys Gly
                                                    1 gag gcg tcg gag aag atc atc atc aac gtg g gc ggc acg cga cat gag         164
Glu Ala Ser Glu Lys Ile Ile Ile Asn Val G ly Gly Thr Arg His Glu
 5                  10                  15                  20 acc tac cgc agc acc ctg cgc acc cta ccg g ga acc cgc ctc gcc tgg         212
Thr Tyr Arg Ser Thr Leu Arg Thr Leu Pro G ly Thr Arg Leu Ala Trp
                25                  30                  35 ctg gcc gac ccc gac ggc ggg ggc cgg ccc g ag acc gat ggc ggc ggt         260
Leu Ala Asp Pro Asp Gly Gly Gly Arg Pro G lu Thr Asp Gly Gly Gly
            40                  45                  50 gtg ggt agc agc ggc agc agc ggc ggc ggg g gc tgc gag ttc ttc ttc         308
Val Gly Ser Ser Gly Ser Ser Gly Gly Gly G ly Cys Glu Phe Phe Phe
        55                  60                  65 gac agg cac ccg ggc gtc ttc gcc tac gtg c tc aac tac tac cgc acc         356
Asp Arg His Pro Gly Val Phe Ala Tyr Val L eu Asn Tyr Tyr Arg Thr
    70                  75                  80 ggc aag ctg cac tgc ccc gca gac gtg tgc g gg ccg ctc ttc gag gag         404
Gly Lys Leu His Cys Pro Ala Asp Val Cys G ly Pro Leu Phe Glu Glu
85                  90                  95                  100
```

-continued

| | |
|---|---|
| gag ctg gcc ttc tgg ggc atc gac gag acc g ac gtg gag ccc tgc tgc<br>Glu Leu Ala Phe Trp Gly Ile Asp Glu Thr A sp Val Glu Pro Cys Cys<br>                                  105                          110                         115 | 452 |
| tgg atg acc tac cgg cag cac cgc gac gcc g ag gag gcg ctg gac atc<br>Trp Met Thr Tyr Arg Gln His Arg Asp Ala G lu Glu Ala Leu Asp Ile<br>                120                       125                      130 | 500 |
| ttc gag acc ccc gac ctc att ggc ggc gac c cc ggc gac gac gag gac<br>Phe Glu Thr Pro Asp Leu Ile Gly Gly Asp P ro Gly Asp Asp Glu Asp<br>                   135                       140                     145 | 548 |
| ctg gcg gcc aag agg ctg ggc atc gag gac g cg gcg ggg ctc ggg ggc<br>Leu Ala Ala Lys Arg Leu Gly Ile Glu Asp A la Ala Gly Leu Gly Gly<br>       150                     155                      160 | 596 |
| ccc gac ggc aaa tct ggc cgc tgg agg agg c tg cag ccc cgc atg tgg<br>Pro Asp Gly Lys Ser Gly Arg Trp Arg Arg L eu Gln Pro Arg Met Trp<br>165                     170                     175                 180 | 644 |
| gcc ctc ttc gaa gac ccc tac tcg tcc aga g cc gcc agg ttt att gct<br>Ala Leu Phe Glu Asp Pro Tyr Ser Ser Arg A la Ala Arg Phe Ile Ala<br>                185                     190                     195 | 692 |
| ttt gct tct tta ttc ttc atc ctg gtt tca a tt aca act ttt tgc ctg<br>Phe Ala Ser Leu Phe Phe Ile Leu Val Ser I le Thr Thr Phe Cys Leu<br>            200                     205                     210 | 740 |
| gaa aca cat gaa gct ttc aat att gtt aaa a ac aag aca gaa cca gtc<br>Glu Thr His Glu Ala Phe Asn Ile Val Lys A sn Lys Thr Glu Pro Val<br>                215                     220                     225 | 788 |
| atc aat ggc aca agt gtt gtt cta cag tat g aa att gaa acg gat cct<br>Ile Asn Gly Thr Ser Val Val Leu Gln Tyr G lu Ile Glu Thr Asp Pro<br>       230                     235                      240 | 836 |
| gcc ttg acg tat gta gaa gga gtg tgt gtg g tg tgg ttt act ttt gaa<br>Ala Leu Thr Tyr Val Glu Gly Val Cys Val V al Trp Phe Thr Phe Glu<br>245                     250                     255                 260 | 884 |
| ttt tta gtc cgt att gtt ttt tca ccc aat a aa ctt gaa ttc atc aaa<br>Phe Leu Val Arg Ile Val Phe Ser Pro Asn L ys Leu Glu Phe Ile Lys<br>                     265                     270                     275 | 932 |
| aat ctc ttg aat atc att gac ttt gtg gcc a tc cta cct ttc tac tta<br>Asn Leu Leu Asn Ile Ile Asp Phe Val Ala I le Leu Pro Phe Tyr Leu<br>            280                     285                     290 | 980 |
| gag gtg gga ctc agt ggg ctg tca tcc aaa g ct gct aaa gat gtg ctt<br>Glu Val Gly Leu Ser Gly Leu Ser Ser Lys A la Ala Lys Asp Val Leu<br>       295                     300                      305 | 1028 |
| ggc ttc ctc agg gtg gta agg ttt gtg agg a tc ctg aga att ttc aag<br>Gly Phe Leu Arg Val Val Arg Phe Val Arg I le Leu Arg Ile Phe Lys<br>310                     315                     320 | 1076 |
| ctc acc cgc cat ttt gta ggt ctg agg gtg c tt gga cat act ctt cga<br>Leu Thr Arg His Phe Val Gly Leu Arg Val L eu Gly His Thr Leu Arg<br>325                     330                     335                 340 | 1124 |
| gct agt act aat gaa ttt ttg ctg ctg ata a tt ttc ctg gct cta gga<br>Ala Ser Thr Asn Glu Phe Leu Leu Leu Ile I le Phe Leu Ala Leu Gly<br>                345                     350                     355 | 1172 |
| gtt ttg ata ttt gct acc atg atc tac tat g cc gag aga gtg gga gct<br>Val Leu Ile Phe Ala Thr Met Ile Tyr Tyr A la Glu Arg Val Gly Ala<br>            360                     365                     370 | 1220 |
| caa cct aac gac cct tca gct agt gag cac a ca cag ttc aaa aac att<br>Gln Pro Asn Asp Pro Ser Ala Ser Glu His T hr Gln Phe Lys Asn Ile<br>       375                     380                      385 | 1268 |
| ccc att ggg ttc tgg tgg gct gta gtg acc a tg act acc ctg ggt tat<br>Pro Ile Gly Phe Trp Trp Ala Val Val Thr M et Thr Thr Leu Gly Tyr<br>390                     395                     400 | 1316 |
| ggg gat atg tac ccc caa aca tgg tca ggc a tg ctg gtg gga gcc ctg<br>Gly Asp Met Tyr Pro Gln Thr Trp Ser Gly M et Leu Val Gly Ala Leu | 1364 |

```
                                                                          1412
tgt gct ctg gct gga gtg ctg aca ata gcc a tg cca gtg cct gtc att
Cys Ala Leu Ala Gly Val Leu Thr Ile Ala M et Pro Val Pro Val Ile
405             410             415             420
                425                 430                 435 gtc aat aat ttt gga atg tac tac tcc ttg g ca atg gca aag cag aaa    1460
Val Asn Asn Phe Gly Met Tyr Tyr Ser Leu A la Met Ala Lys Gln Lys
                440                 445                 450 ctt cca agg aaa aga aag aag cac atc cct c ct gct cct cag gca agc    1508
Leu Pro Arg Lys Arg Lys Lys His Ile Pro P ro Ala Pro Gln Ala Ser
                455                 460                 465 tca cct act ttt tgc aag aca gaa tta aat a tg gcc tgc aat agt aca    1556
Ser Pro Thr Phe Cys Lys Thr Glu Leu Asn M et Ala Cys Asn Ser Thr
                470                 475                 480 cag agt gac aca tgt ctg ggc aaa gac aat c ga ctt ctg gaa cat aac    1604
Gln Ser Asp Thr Cys Leu Gly Lys Asp Asn A rg Leu Leu Glu His Asn
485             490                 495                 500 aga tca gtg tta tca ggt gac gac agt aca g ga agt gag ccg cca cta    1652
Arg Ser Val Leu Ser Gly Asp Asp Ser Thr G ly Ser Glu Pro Pro Leu
                505                 510                 515 tca ccc cca gaa agg ctc ccc atc aga cgc t ct agt acc aga gac aaa    1700
Ser Pro Pro Glu Arg Leu Pro Ile Arg Arg S er Ser Thr Arg Asp Lys
                520                 525                 530 aac aga aga ggg gaa aca tgt ttc cta ctg a cg aca ggt gat tac acg    1748
Asn Arg Arg Gly Glu Thr Cys Phe Leu Leu T hr Thr Gly Asp Tyr Thr
                535                 540                 545 tgt gct tct gat gga ggg atc agg aaa gga t at gaa aaa tcc cga agc    1796
Cys Ala Ser Asp Gly Gly Ile Arg Lys Gly T yr Glu Lys Ser Arg Ser
550                 555                 560 tta aac aac ata gcg ggc ttg gca ggc aat g ct ctg agg ctc tct cca    1844
Leu Asn Asn Ile Ala Gly Leu Ala Gly Asn A la Leu Arg Leu Ser Pro
565                 570                 575                 580 gta aca tca ccc tac aac tct cct tgt cct c tg agg cgc tct cga tct    1892
Val Thr Ser Pro Tyr Asn Ser Pro Cys Pro L eu Arg Arg Ser Arg Ser
                585                 590                 595 ccc atc cca tct atc t tgtaaaccaa accctcgtg                          1927
Pro Ile Pro Ser Ile
                600

<210> SEQ ID NO 4
<211> LENGTH: 601
<212> TYPE: PRT
<213> ORGANISM: H. sapiens

<400> SEQUENCE: 4

Met Ala Lys Gly Glu Ala Ser Glu Lys Ile I le Ile Asn Val Gly Gly
1               5                   10                  15

Thr Arg His Glu Thr Tyr Arg Ser Thr Leu A rg Thr Leu Pro Gly Thr
                20                  25                  30

Arg Leu Ala Trp Leu Ala Asp Pro Asp Gly G ly Gly Arg Pro Glu Thr
                35                  40                  45

Asp Gly Gly Gly Val Gly Ser Ser Gly Ser S er Gly Gly Gly Gly Cys
                50                  55                  60

Glu Phe Phe Phe Asp Arg His Pro Gly Val P he Ala Tyr Val Leu Asn
65                  70                  75                  80

Tyr Tyr Arg Thr Gly Lys Leu His Cys Pro A la Asp Val Cys Gly Pro
                85                  90                  95

Leu Phe Glu Glu Glu Leu Ala Phe Trp Gly I le Asp Glu Thr Asp Val
                100                 105                 110
```

-continued

```
Glu Pro Cys Cys Trp Met Thr Tyr Arg Gln His Arg Asp Ala Glu Glu
            115                 120                 125
Ala Leu Asp Ile Phe Glu Thr Pro Asp Leu Ile Gly Gly Asp Pro Gly
        130                 135                 140
Asp Asp Glu Asp Leu Ala Ala Lys Arg Leu Gly Ile Glu Asp Ala Ala
145                 150                 155                 160
Gly Leu Gly Gly Pro Asp Gly Lys Ser Gly Arg Trp Arg Arg Leu Gln
                165                 170                 175
Pro Arg Met Trp Ala Leu Phe Glu Asp Pro Tyr Ser Ser Arg Ala Ala
            180                 185                 190
Arg Phe Ile Ala Phe Ala Ser Leu Phe Phe Ile Leu Val Ser Ile Thr
        195                 200                 205
Thr Phe Cys Leu Glu Thr His Glu Ala Phe Asn Ile Val Lys Asn Lys
    210                 215                 220
Thr Glu Pro Val Ile Asn Gly Thr Ser Val Val Leu Gln Tyr Glu Ile
225                 230                 235                 240
Glu Thr Asp Pro Ala Leu Thr Tyr Val Glu Gly Val Cys Val Val Trp
                245                 250                 255
Phe Thr Phe Glu Phe Leu Val Arg Ile Val Phe Ser Pro Asn Lys Leu
            260                 265                 270
Glu Phe Ile Lys Asn Leu Leu Asn Ile Ile Asp Phe Val Ala Ile Leu
        275                 280                 285
Pro Phe Tyr Leu Glu Val Gly Leu Ser Gly Leu Ser Ser Lys Ala Ala
    290                 295                 300
Lys Asp Val Leu Gly Phe Leu Arg Val Val Arg Phe Val Arg Ile Leu
305                 310                 315                 320
Arg Ile Phe Lys Leu Thr Arg His Phe Val Gly Leu Arg Val Leu Gly
                325                 330                 335
His Thr Leu Arg Ala Ser Thr Asn Glu Phe Leu Leu Leu Ile Ile Phe
            340                 345                 350
Leu Ala Leu Gly Val Leu Ile Phe Ala Thr Met Ile Tyr Tyr Ala Glu
        355                 360                 365
Arg Val Gly Ala Gln Pro Asn Asp Pro Ser Ala Ser Glu His Thr Gln
    370                 375                 380
Phe Lys Asn Ile Pro Ile Gly Phe Trp Trp Ala Val Val Thr Met Thr
385                 390                 395                 400
Thr Leu Gly Tyr Gly Asp Met Tyr Pro Gln Thr Trp Ser Gly Met Leu
                405                 410                 415
Val Gly Ala Leu Cys Ala Leu Ala Gly Val Leu Thr Ile Ala Met Pro
            420                 425                 430
Val Pro Val Ile Val Asn Asn Phe Gly Met Tyr Tyr Ser Leu Ala Met
        435                 440                 445
Ala Lys Gln Lys Leu Pro Arg Lys Arg Lys Lys His Ile Pro Pro Ala
    450                 455                 460
Pro Gln Ala Ser Ser Pro Thr Phe Cys Lys Thr Glu Leu Asn Met Ala
465                 470                 475                 480
Cys Asn Ser Thr Gln Ser Asp Thr Cys Leu Gly Lys Asp Asn Arg Leu
                485                 490                 495
Leu Glu His Asn Arg Ser Val Leu Ser Gly Asp Asp Ser Thr Gly Ser
            500                 505                 510
Glu Pro Pro Leu Ser Pro Pro Glu Arg Leu Pro Ile Arg Arg Ser Ser
        515                 520                 525
Thr Arg Asp Lys Asn Arg Arg Gly Glu Thr Cys Phe Leu Leu Thr Thr
```

|  |  |  | 530 |  |  |  | 535 |  |  |  | 540 |  |  |
|---|---|---|---|---|---|---|---|---|---|---|---|---|---|
| Gly | Asp | Tyr | Thr | Cys | Ala | Ser | Asp | Gly | Gly | Ile | Arg | Lys | Gly | Tyr | Glu |
| 545 |  |  |  | 550 |  |  |  | 555 |  |  |  | 560 |

Lys Ser Arg Ser Leu Asn Asn Ile Ala Gly Leu Ala Gly Asn Ala Leu
            565                 570                 575

Arg Leu Ser Pro Val Thr Ser Pro Tyr Asn Ser Pro Cys Pro Leu Arg
        580                 585                 590

Arg Ser Arg Ser Pro Ile Pro Ser Ile
        595                 600

<210> SEQ ID NO 5
<211> LENGTH: 2293
<212> TYPE: DNA
<213> ORGANISM: H. sapiens
<220> FEATURE:
<221> NAME/KEY: CDS
<222> LOCATION: (330)...(1800)
<223> OTHER INFORMATION: K+Hnov6

<400> SEQUENCE: 5

```
gggaagagcg aacccagggc ccttgctctc gtgcagcgct gcgccctggg t ggggacggc      60 gtgaggcttg cagcgcaggt gagagtgatt ttccagtgat tgctttggcc t gtacaacca     120 gagaacagga ttcttccctt cttttggcc accaaatgcc tatgtgcacc a cacattcca     180 gtgtgctgag aagggcagag cttcttggat gatgatggac gtcccaccgg g caggatgaa    240 ggcagagcgt gtggcatctc cacctcaagg gtgcagcctg atcttcctct t ctcccttgc   300 cagccagcac tctgccttct gtatccacc atg gtg ttt ggt ga g ttt ttc cat     353
                                Met Val Phe Gly Glu Phe Phe His
                                 1               5
```

```
cgc cct gga caa gac gag gaa ctt gtc aac c tg aat gtg ggg ggc ttt      401
Arg Pro Gly Gln Asp Glu Glu Leu Val Asn Leu Asn Val Gly Gly Phe
     10                  15                  20
```

```
aag cag tct gtt gac caa agc acc ctc ctg c gg ttt cct cac acc aga      449
Lys Gln Ser Val Asp Gln Ser Thr Leu Leu Arg Phe Pro His Thr Arg
 25                  30                  35                  40
```

```
ctg ggg aag ctg ctt act tgc cat tct gaa g ag gcc att ctg gag ctg      497
Leu Gly Lys Leu Leu Thr Cys His Ser Glu Glu Ala Ile Leu Glu Leu
                 45                  50                  55
```

```
tgt gat gat tac agt gtg gcc gat aag gaa t ac tac ttt gat cgg aat      545
Cys Asp Asp Tyr Ser Val Ala Asp Lys Glu Tyr Tyr Phe Asp Arg Asn
             60                  65                  70
```

```
ccc tcc ttg ttc aga tat gtt ttg aat ttt t at tac acg ggg aag ctg      593
Pro Ser Leu Phe Arg Tyr Val Leu Asn Phe Tyr Tyr Thr Gly Lys Leu
         75                  80                  85
```

```
cat gtc atg gag gag ctg tgc gta ttc tca t tc tgc cag gag atc gag      641
His Val Met Glu Glu Leu Cys Val Phe Ser Phe Cys Gln Glu Ile Glu
     90                  95                 100
```

```
tac tgg ggc atc aac gag ctc ttc att gat t ct tgc tgc agc aat cgc      689
Tyr Trp Gly Ile Asn Glu Leu Phe Ile Asp Ser Cys Cys Ser Asn Arg
105                 110                 115                 120
```

```
tac cag gaa cgc aag gag gaa aac cac gag a ag gac tgg gac cag aaa      737
Tyr Gln Glu Arg Lys Glu Glu Asn His Glu Lys Asp Trp Asp Gln Lys
                125                 130                 135
```

```
agc cat gat gtg agt acc gac tcc tcg ttt g aa gag tcg tct ctg ttt      785
Ser His Asp Val Ser Thr Asp Ser Ser Phe Glu Glu Ser Ser Leu Phe
            140                 145                 150
```

```
gag aaa gag ctg gag aag ttt gac aca ctg c ga ttt ggt cag ctc cgg      833
Glu Lys Glu Leu Glu Lys Phe Asp Thr Leu Arg Phe Gly Gln Leu Arg
        155                 160                 165
```

```
aag aaa atc tgg att aga atg gag aat cca g cg tac tgc ctg tcc gct         881
Lys Lys Ile Trp Ile Arg Met Glu Asn Pro A la Tyr Cys Leu Ser Ala
        170                 175                  180 aag ctt atc gct atc tcc tcc ttg agc gtg g tg ctg gcc tcc atc gtg         929
Lys Leu Ile Ala Ile Ser Ser Leu Ser Val V al Leu Ala Ser Ile Val
185                 190                  195                 200 gcc atg tgc gtt cac agc atg tcg gag ttc c ag aat gag gat gga gaa         977
Ala Met Cys Val His Ser Met Ser Glu Phe G ln Asn Glu Asp Gly Glu
                    205                  210                 215 gtg gat gat ccg gtg ctg gaa gga gtg gag a tc gcg tgc att gcc tgg        1025
Val Asp Asp Pro Val Leu Glu Gly Val Glu I le Ala Cys Ile Ala Trp
                220                  225                 230 ttc acc ggg gag ctt gcc gtc cgg ctg gct g cc gct cct tgt caa aag        1073
Phe Thr Gly Glu Leu Ala Val Arg Leu Ala A la Ala Pro Cys Gln Lys
            235                  240                 245 aaa ttc tgg aaa aac cct ctg aac atc att g ac ttt gtc tct att att        1121
Lys Phe Trp Lys Asn Pro Leu Asn Ile Ile A sp Phe Val Ser Ile Ile
250                 255                  260 ccc ttc tat gcc acg ttg gct gta gac acc a ag gag gaa gag agt gag        1169
Pro Phe Tyr Ala Thr Leu Ala Val Asp Thr L ys Glu Glu Glu Ser Glu
265                 270                  275                 280 gat att gag aac atg ggc aag gtg gtc cag a tc cta cgg ctt atg agg        1217
Asp Ile Glu Asn Met Gly Lys Val Val Gln I le Leu Arg Leu Met Arg
                285                  290                 295 att ttc cga att cta aag ctt gcc cgg cac t cg gta gga ctt cgg tct        1265
Ile Phe Arg Ile Leu Lys Leu Ala Arg His S er Val Gly Leu Arg Ser
                300                  305                 310 cta ggt gcc aca ctg aga cac agc tac cat g aa gtt ggg ctt ctg ctt        1313
Leu Gly Ala Thr Leu Arg His Ser Tyr His G lu Val Gly Leu Leu Leu
            315                  320                 325 ctc ttc ctc tct gtg ggc att tcc att ttc t ct gtg ctt atc tac tcc        1361
Leu Phe Leu Ser Val Gly Ile Ser Ile Phe S er Val Leu Ile Tyr Ser
330                 335                  340 gtg gag aaa gat gac cac aca tcc agc ctc a cc agc atc ccc atc tgc        1409
Val Glu Lys Asp Asp His Thr Ser Ser Leu T hr Ser Ile Pro Ile Cys
345                 350                  355                 360 tgg tgg tgg gcc acc atc agc atg aca act g tg ggc tat gga gac acc        1457
Trp Trp Trp Ala Thr Ile Ser Met Thr Thr V al Gly Tyr Gly Asp Thr
                365                  370                 375 cac ccg gtc acc ttg gcg gga aag ctc atc g cc agc aca tgc atc atc        1505
His Pro Val Thr Leu Ala Gly Lys Leu Ile A la Ser Thr Cys Ile Ile
            380                  385                 390 tgt ggc atc ttg gtg gtg gcc ctt ccc atc a cc atc atc ttc aac aag        1553
Cys Gly Ile Leu Val Val Ala Leu Pro Ile T hr Ile Ile Phe Asn Lys
            395                  400                 405 ttt tcc aag tac tac cag aag caa aag gac a tt gat gtg gac cag tgc        1601
Phe Ser Lys Tyr Tyr Gln Lys Gln Lys Asp I le Asp Val Asp Gln Cys
410                 415                  420 agt gag gat gca cca gag aag tgt cat gag c ta cct tac ttt aac att        1649
Ser Glu Asp Ala Pro Glu Lys Cys His Glu L eu Pro Tyr Phe Asn Ile
425                 430                  435                 440 agg gat ata tat gca cag cgg atg cac gcc t tc att acc agt ctc tct        1697
Arg Asp Ile Tyr Ala Gln Arg Met His Ala P he Ile Thr Ser Leu Ser
                445                  450                 455 tct gta ggc att gtg gtg agc gat cct gac t cc aca gat gct tca agc        1745
Ser Val Gly Ile Val Val Ser Asp Pro Asp S er Thr Asp Ala Ser Ser
            460                  465                 470 att gaa gac aat gag gac att tgt aac acc a cc tcc ttg gag aat tgc        1793
Ile Glu Asp Asn Glu Asp Ile Cys Asn Thr T hr Ser Leu Glu Asn Cys
```

-continued

```
                475                 480                 485
aca gca a aatgagcggg ggtgtttgtg cctgtttctc ttatcctttc  ccaacattag   1850
Thr Ala
    490 gttaacacag ctttataaac ctcagtgggt tcgttaaaat catttaattc t cagggtgta   1910 cctttcagcc atagttggac attcattgct gaattctgaa atgatagaat t gtctttatt   1970 tttctctgtg aggtcaatta aatgccttgt tctgaaattt attttttaca a gagagagtt   2030 gtgatagagt ttggaatata agataaatgg tattgggtgg ggtttgtggc t acagcttat   2090 gcatcattct gtgtttgtca tttactcaca ttgagctaac tttaaattac t gacaagtag   2150 aatcaaaggt gcagctgact gagacgacat gcatgtaaga tccacaaaat g agacaatgc   2210 atgtaaatcc atgctcatgt tctaaacatg gaaactagga gcctaataaa c ttcctaatt   2270 cagaaaaaaa aaaaaaaaaa aaa                                            2293
```

<210> SEQ ID NO 6
<211> LENGTH: 490
<212> TYPE: PRT
<213> ORGANISM: H. sapiens

<400> SEQUENCE: 6

```
Met Val Phe Gly Glu Phe Phe His Arg Pro G ly Gln Asp Glu Glu Leu
  1               5                  10                  15

Val Asn Leu Asn Val Gly Gly Phe Lys Gln S er Val Asp Gln Ser Thr
             20                  25                  30

Leu Leu Arg Phe Pro His Thr Arg Leu Gly L ys Leu Leu Thr Cys His
         35                  40                  45

Ser Glu Glu Ala Ile Leu Glu Leu Cys Asp A sp Tyr Ser Val Ala Asp
     50                  55                  60

Lys Glu Tyr Tyr Phe Asp Arg Asn Pro Ser L eu Phe Arg Tyr Val Leu
 65                  70                  75                  80

Asn Phe Tyr Tyr Thr Gly Lys Leu His Val M et Glu Glu Leu Cys Val
                 85                  90                  95

Phe Ser Phe Cys Gln Glu Ile Glu Tyr Trp G ly Ile Asn Glu Leu Phe
            100                 105                 110

Ile Asp Ser Cys Cys Ser Asn Arg Tyr Gln G lu Arg Lys Glu Glu Asn
        115                 120                 125

His Glu Lys Asp Trp Asp Gln Lys Ser His A sp Val Ser Thr Asp Ser
    130                 135                 140

Ser Phe Glu Glu Ser Ser Leu Phe Glu Lys G lu Leu Glu Lys Phe Asp
145                 150                 155                 160

Thr Leu Arg Phe Gly Gln Leu Arg Lys Lys I le Trp Ile Arg Met Glu
                165                 170                 175

Asn Pro Ala Tyr Cys Leu Ser Ala Lys Leu I le Ala Ile Ser Ser Leu
            180                 185                 190

Ser Val Leu Ala Ser Ile Val Ala Met C ys Val His Ser Met Ser
        195                 200                 205

Glu Phe Gln Asn Glu Asp Gly Glu Val Asp A sp Pro Val Leu Glu Gly
    210                 215                 220

Val Glu Ile Ala Cys Ile Ala Trp Phe Thr G ly Glu Leu Ala Val Arg
225                 230                 235                 240

Leu Ala Ala Ala Pro Cys Gln Lys Lys Phe T rp Lys Asn Pro Leu Asn
                245                 250                 255

Ile Ile Asp Phe Val Ser Ile Ile Pro Phe T yr Ala Thr Leu Ala Val
```

-continued

```
                  260                   265                   270
Asp Thr Lys Glu Glu Ser Glu Asp Ile Glu Asn Met Gly Lys Val
            275                   280                   285

Val Gln Ile Leu Arg Leu Met Arg Ile Phe Arg Ile Leu Lys Leu Ala
            290                   295                   300

Arg His Ser Val Gly Leu Arg Ser Leu Gly Ala Thr Leu Arg His Ser
305                   310                   315                   320

Tyr His Glu Val Gly Leu Leu Leu Phe Leu Ser Val Gly Ile Ser
                325                   330                   335

Ile Phe Ser Val Leu Ile Tyr Ser Val Glu Lys Asp Asp His Thr Ser
                340                   345                   350

Ser Leu Thr Ser Ile Pro Ile Cys Trp Trp Trp Ala Thr Ile Ser Met
            355                   360                   365

Thr Thr Val Gly Tyr Gly Asp Thr His Pro Val Thr Leu Ala Gly Lys
            370                   375                   380

Leu Ile Ala Ser Thr Cys Ile Ile Cys Gly Ile Leu Val Val Ala Leu
385                   390                   395                   400

Pro Ile Thr Ile Ile Phe Asn Lys Phe Ser Lys Tyr Tyr Gln Lys Gln
                405                   410                   415

Lys Asp Ile Asp Val Asp Gln Cys Ser Glu Asp Ala Pro Glu Lys Cys
                420                   425                   430

His Glu Leu Pro Tyr Phe Asn Ile Arg Asp Ile Tyr Ala Gln Arg Met
            435                   440                   445

His Ala Phe Ile Thr Ser Leu Ser Ser Val Gly Ile Val Val Ser Asp
            450                   455                   460

Pro Asp Ser Thr Asp Ala Ser Ser Ile Glu Asp Asn Glu Asp Ile Cys
465                   470                   475                   480

Asn Thr Thr Ser Leu Glu Asn Cys Thr Ala
                485                   490

<210> SEQ ID NO 7
<211> LENGTH: 3080
<212> TYPE: DNA
<213> ORGANISM: H. sapiens
<220> FEATURE:
<221> NAME/KEY: CDS
<222> LOCATION: (480)...(1977)
<223> OTHER INFORMATION: K+Hnov9

<400> SEQUENCE: 7
gtctctcctc ttcctcctcc tccgccccac atctccctcc ttcctcccttc cccaaccccc       60 tccacccacc aagtagcgag tcattcaatc tgtacacctc ctgggctggg a atcgcaatt      120 gcgaagttgg gaggcggggt gacaacgttt gggaagggcc agggcgaccg g cagtgtgca      180 cagggactgt gtcgggcttg gacctcacct gatcctctct cttagcgcga c ccttcctct     240 gctccctgtc tcctctttct gccacttgtg cgctgcttcc gcgcactccc g gctccctag    300 cggcaggagg aggaaggcgc acagcgggtg gagagggtgc gccaaggaga g gtaaccct     360 tcgggagccc gggggaatccc ggccgccacc agggccgtg ccaccgccct c gcgggacca    420 aagcttccgg cgtgtcccca actttgtggc ccctcaggc cgcggcgact g ggttagag      479 atg cct tcc agc ggc aga gcg ctg ctg gac tcg ccg ctg gac agc ggc        527
Met Pro Ser Ser Gly Arg Ala Leu Leu Asp Ser Pro Leu Asp Ser Gly
 1               5                  10                  15 tcc ctg acc tcc ctg gac tct agt gtc ttc tgc agc gag ggt gaa ggg        575
Ser Leu Thr Ser Leu Asp Ser Ser Val Phe Cys Ser Glu Gly Glu Gly
```

-continued

| | | 20 | | | 25 | | | 30 | | |
|---|---|---|---|---|---|---|---|---|---|---|

```
gag ccc ttg gcg ctc ggg gac tgc ttc acg g tc aac gtg ggc ggc agc     623
Glu Pro Leu Ala Leu Gly Asp Cys Phe Thr V al Asn Val Gly Gly Ser
         35                  40                  45 cgc ttc gtg ctc tcg cag cag gcg ctg tcc t gc ttc ccg cac acg cgc     671
Arg Phe Val Leu Ser Gln Gln Ala Leu Ser C ys Phe Pro His Thr Arg
     50                  55                  60 ctt ggc aag ctg gcc gtg gtg gtg gct tcc t ac cgc cgc ccc ggg gcc     719
Leu Gly Lys Leu Ala Val Val Val Ala Ser T yr Arg Arg Pro Gly Ala
 65                  70                  75                  80 ctg gcc gcc gtg ccc agc cct ctg gag ctt t gc gac gat gcc aac ccc     767
Leu Ala Ala Val Pro Ser Pro Leu Glu Leu C ys Asp Asp Ala Asn Pro
                 85                  90                  95 gtg gac aac gag tac ttc ttc gac cgc agc t cg cag gcg ttc cga tat     815
Val Asp Asn Glu Tyr Phe Phe Asp Arg Ser S er Gln Ala Phe Arg Tyr
             100                 105                 110 gtc ctg cac tac tac cgc acc ggc cgc ctg c at gtc atg gag cag ctg     863
Val Leu His Tyr Tyr Arg Thr Gly Arg Leu H is Val Met Glu Gln Leu
         115                 120                 125 tgc gcg ctc tcc ttc ctg cag gag atc cag t ac tgg ggc atc gat gag     911
Cys Ala Leu Ser Phe Leu Gln Glu Ile Gln T yr Trp Gly Ile Asp Glu
     130                 135                 140 ctc agc atc gat tcc tgc tgc agg gac aga t ac ttc aga agg aaa gag     959
Leu Ser Ile Asp Ser Cys Cys Arg Asp Arg T yr Phe Arg Arg Lys Glu
 145                 150                 155                 160 ctg agt gaa act tta gac ttc aag aag gac a ca gaa gac cag gaa agt    1007
Leu Ser Glu Thr Leu Asp Phe Lys Lys Asp T hr Glu Asp Gln Glu Ser
                 165                 170                 175 caa cat gag agt gaa cag gac ttc tcc caa g ga cct tgt ccc act gtt    1055
Gln His Glu Ser Glu Gln Asp Phe Ser Gln G ly Pro Cys Pro Thr Val
             180                 185                 190 cgc cag aag ctc tgg aat atc ctg gag aaa c ct gga tct tcc aca gct    1103
Arg Gln Lys Leu Trp Asn Ile Leu Glu Lys P ro Gly Ser Ser Thr Ala
         195                 200                 205 gcc cgt atc ttt ggc gtc atc tcc att atc t tc gtg gtg gtg tcc atc    1151
Ala Arg Ile Phe Gly Val Ile Ser Ile Ile P he Val Val Val Ser Ile
     210                 215                 220 att aac atg gcc ctg atg tca gct gag tta a gc tgg ctg gac ctg cag    1199
Ile Asn Met Ala Leu Met Ser Ala Glu Leu S er Trp Leu Asp Leu Gln
225                 230                 235                 240 ctg ctg gaa atc ctg gag tat gtg tgc att a gc tgg ttc acc ggg gag    1247
Leu Leu Glu Ile Leu Glu Tyr Val Cys Ile S er Trp Phe Thr Gly Glu
                 245                 250                 255 ttt gtc ctc cgc ttc ctg tgt gtg cgg gac a gg tgt cgc ttc cta aga    1295
Phe Val Leu Arg Phe Leu Cys Val Arg Asp A rg Cys Arg Phe Leu Arg
             260                 265                 270 aag gtg cca aac atc ata gac ctc ctt gcc a tc ttg ccc ttc tac atc    1343
Lys Val Pro Asn Ile Ile Asp Leu Leu Ala I le Leu Pro Phe Tyr Ile
         275                 280                 285 act ctt ctg gta gag agc cta agt ggg agc c ag acc acg cag gag ctg    1391
Thr Leu Leu Val Glu Ser Leu Ser Gly Ser G ln Thr Thr Gln Glu Leu
     290                 295                 300 gag aac gtg ggg cgc att gtc cag gtg ttg a gg ctg ctc agg gct ctg    1439
Glu Asn Val Gly Arg Ile Val Gln Val Leu A rg Leu Leu Arg Ala Leu
305                 310                 315                 320 cgc atg cta aag ctg ggc aga cat tcc aca g ga tta cgc tcc ctt ggg    1487
Arg Met Leu Lys Leu Gly Arg His Ser Thr G ly Leu Arg Ser Leu Gly
                 325                 330                 335 atg aca atc acc cag tgt tac gaa gaa gtc g gc cta ctg ctc cta ttt    1535
```

```
Met Thr Ile Thr Gln Cys Tyr Glu Glu Val G ly Leu Leu Leu Leu Phe
            340                 345                  350 cta tcc gtg gga atc tct ata ttt tca act g ta gaa tac ttt gct gag         1583
Leu Ser Val Gly Ile Ser Ile Phe Ser Thr V al Glu Tyr Phe Ala Glu
            355                 360                 365 caa agc att cct gac aca acc ttc aca agt g tc cct tgt gca tgg tgg         1631
Gln Ser Ile Pro Asp Thr Thr Phe Thr Ser V al Pro Cys Ala Trp Trp
    370                 375                 380 tgg gcc acc acc tct atg act act gtg gga t at ggg gac att aga cca         1679
Trp Ala Thr Thr Ser Met Thr Thr Val Gly T yr Gly Asp Ile Arg Pro
385                 390                 395                 400 gac acc acc aca ggc aaa atc gtg gcc ttc a tg tgt ata tta tcg gga         1727
Asp Thr Thr Thr Gly Lys Ile Val Ala Phe M et Cys Ile Leu Ser Gly
                405                 410                 415 att ctt gtc ttg gcc ttg cct att gct att a tt aac gat cgc ttc tct         1775
Ile Leu Val Leu Ala Leu Pro Ile Ala Ile I le Asn Asp Arg Phe Ser
            420                 425                 430 gct tgc tac ttc acc ttg aaa ctc aag gaa g ca gct gtt aga cag cgt         1823
Ala Cys Tyr Phe Thr Leu Lys Leu Lys Glu A la Ala Val Arg Gln Arg
            435                 440                 445 gaa gcc cta aag aag ctt acc aag aat ata g cc act gac tca tat atc         1871
Glu Ala Leu Lys Lys Leu Thr Lys Asn Ile A la Thr Asp Ser Tyr Ile
    450                 455                 460 agt gtt aac ttg aga gat gtc tat gcc cgg a gt atc atg gag atg ctg         1919
Ser Val Asn Leu Arg Asp Val Tyr Ala Arg S er Ile Met Glu Met Leu
465                 470                 475                 480 cga ctg aaa ggc aga gaa aga gca agt act a gg agc agc ggg gga gat         1967
Arg Leu Lys Gly Arg Glu Arg Ala Ser Thr A rg Ser Ser Gly Gly Asp
                485                 490                 495 gat ttc tgg t tttgaattaa ttttcaattt atttacaaaa gct atgtaca              2017
Asp Phe Trp attaactaaa atgataaagc agtgatgtgg atttctgtat tctgatgatg a gtctcttca      2077 gagtactgct catcttaatt aatttttgct gatatattgc ttcatctact a gaatatttc      2137 acatcaccta taacaactgc acagtgttct gacacatttg agtgtccaaa a tagccaatt      2197 aacacaacca aatacaactg ggccaatata aacatgtttg aattgtcaaa t ataaaataa      2257 tgttattgca atacatacaa aaaagttaaa gattttatgt atcactaaca t tagaagttt     2317 tttgcaccac taatttttta aaaatggaag gtaaactgca tagcccagag a agataagt      2377 aaatatttaa gaacatattg aacaactttg ctatttaaag atattatcca a gtacataaa     2437 ttactccgtt ctctatcagt taaagctatt gaatataata cttagcttta c aagagaaaa    2497 cccatatttg atgggcagag attatatccc tatcttcttt ttcatgtaaa c cactggtca    2557 caaatgaact gatctctgta tcccattatt actataagag gtgggaatcc c aaaactgct   2617 tagattgcag tacatgagtc tacacaaaga cttcaacaat tgcacatctt c attctccca  2677 actgagtgta gtatgtggag cataaaacag catatttctt agtatttcat g aatatcaga   2737 tggtctttaa atgtctcttt atggatgtat tgttcacatt atggctttaa a ataatgaat   2797 atgtaaaagt gaggtagtga acatcctaaa tttctacact ggaattacta a ataatctta  2857 tttcataaat gggaaatata tgttaaatga catcactgga tgaacttgaa g atcttttac  2917 ttgttaacaa aaaaatacta tggacagctt tctgattgtt ggggtaaata g caaatgttc  2977 aaactttgca ggcattttga cattcatcat aacaacacaa ttcctagaca t tgtattata  3037 taattaaagc caaaacctct aaagctaaaa aaaaaaaaaa aaa                       3080
```

```
<210> SEQ ID NO 8
<211> LENGTH: 499
<212> TYPE: PRT
<213> ORGANISM: H. sapiens

<400> SEQUENCE: 8

Met Pro Ser Ser Gly Arg Ala Leu Leu Asp Ser Pro Leu Asp Ser Gly
 1               5                  10                  15

Ser Leu Thr Ser Leu Asp Ser Val Phe Cys Ser Glu Gly Glu Gly
            20                  25                  30

Glu Pro Leu Ala Leu Gly Asp Cys Phe Thr Val Asn Val Gly Gly Ser
            35                  40                  45

Arg Phe Val Leu Ser Gln Gln Ala Leu Ser Cys Phe Pro His Thr Arg
50                  55                  60

Leu Gly Lys Leu Ala Val Val Ala Ser Tyr Arg Arg Pro Gly Ala
65                  70                  75                  80

Leu Ala Ala Val Pro Ser Pro Leu Glu Leu Cys Asp Asp Ala Asn Pro
                85                  90                  95

Val Asp Asn Glu Tyr Phe Phe Asp Arg Ser Ser Gln Ala Phe Arg Tyr
            100                 105                 110

Val Leu His Tyr Tyr Arg Thr Gly Arg Leu His Val Met Glu Gln Leu
            115                 120                 125

Cys Ala Leu Ser Phe Leu Gln Glu Ile Gln Tyr Trp Gly Ile Asp Glu
130                 135                 140

Leu Ser Ile Asp Ser Cys Cys Arg Asp Arg Tyr Phe Arg Arg Lys Glu
145                 150                 155                 160

Leu Ser Glu Thr Leu Asp Phe Lys Lys Asp Thr Glu Asp Gln Glu Ser
                165                 170                 175

Gln His Glu Ser Glu Gln Asp Phe Ser Gln Gly Pro Cys Pro Thr Val
            180                 185                 190

Arg Gln Lys Leu Trp Asn Ile Leu Glu Lys Pro Gly Ser Ser Thr Ala
            195                 200                 205

Ala Arg Ile Phe Gly Val Ile Ser Ile Ile Phe Val Val Val Ser Ile
        210                 215                 220

Ile Asn Met Ala Leu Met Ser Ala Glu Leu Ser Trp Leu Asp Leu Gln
225                 230                 235                 240

Leu Leu Glu Ile Leu Glu Tyr Val Cys Ile Ser Trp Phe Thr Gly Glu
                245                 250                 255

Phe Val Leu Arg Phe Leu Cys Val Arg Asp Arg Cys Arg Phe Leu Arg
            260                 265                 270

Lys Val Pro Asn Ile Ile Asp Leu Leu Ala Ile Leu Pro Phe Tyr Ile
        275                 280                 285

Thr Leu Leu Val Glu Ser Leu Ser Gly Ser Gln Thr Thr Gln Glu Leu
    290                 295                 300

Glu Asn Val Gly Arg Ile Val Gln Val Leu Arg Leu Leu Arg Ala Leu
305                 310                 315                 320

Arg Met Leu Lys Leu Gly Arg His Ser Thr Gly Leu Arg Ser Leu Gly
                325                 330                 335

Met Thr Ile Thr Gln Cys Tyr Glu Glu Val Gly Leu Leu Leu Leu Phe
            340                 345                 350

Leu Ser Val Gly Ile Ser Ile Phe Ser Thr Val Glu Tyr Phe Ala Glu
        355                 360                 365

Gln Ser Ile Pro Asp Thr Thr Phe Thr Ser Val Pro Cys Ala Trp Trp
370                 375                 380
```

```
Trp Ala Thr Thr Ser Met Thr Thr Val Gly Tyr Gly Asp Ile Arg Pro
385                 390                 395                 400

Asp Thr Thr Thr Gly Lys Ile Val Ala Phe Met Cys Ile Leu Ser Gly
                405                 410                 415

Ile Leu Val Leu Ala Leu Pro Ile Ala Ile Ile Asn Asp Arg Phe Ser
            420                 425                 430

Ala Cys Tyr Phe Thr Leu Lys Leu Lys Glu Ala Ala Val Arg Gln Arg
        435                 440                 445

Glu Ala Leu Lys Lys Leu Thr Lys Asn Ile Ala Thr Asp Ser Tyr Ile
    450                 455                 460

Ser Val Asn Leu Arg Asp Val Tyr Ala Arg Ser Ile Met Glu Met Leu
465                 470                 475                 480

Arg Leu Lys Gly Arg Glu Arg Ala Ser Thr Arg Ser Ser Gly Gly Asp
                485                 490                 495

Asp Phe Trp

<210> SEQ ID NO 9
<211> LENGTH: 3424
<212> TYPE: DNA
<213> ORGANISM: H. sapiens
<220> FEATURE:
<221> NAME/KEY: CDS
<222> LOCATION: (257)...(2195)
<223> OTHER INFORMATION: K+Hnov12

<400> SEQUENCE: 9
ctcttctcca tgtccccaag gcccttctca gtccctcaga acattgccca g gcccctcct      60 aggttctgta aatgtccccc agactccttc ccatctcttt agttcttcct c tggttcct     120 cttggcctct ctagacaccc ccagtttcct tgtttgggtg gctcaaggtg t ctccaagcc    180 cccaccatcc tggagacagc cacattctcc taaacgccac cctcactaag t ctccctggg   240 cttggggagt ggcacg atg gcg gca ggc ctg gcc acg tgg ctg cct ttt gct    292
              Met Ala Ala Gly Leu Ala Thr Trp Leu Pro Phe Ala
                1               5                   10 cgg gca gca gca gtg ggc tgg ctg ccc ccg g cc cag caa ccc ctg ccc    340
Arg Ala Ala Ala Val Gly Trp Leu Pro Pro Ala Gln Gln Pro Leu Pro
        15                  20                  25 ccg gca ccg ggg gtg aag gca tct cga gga g at grg gtt ctg gtg gtg    388
Pro Ala Pro Gly Val Lys Ala Ser Arg Gly Asp Xaa Val Leu Val Val
    30                  35                  40 aac gtg agc gga cgg cgc ttt gag act tgg a ag aat acg ctg gac cgc    436
Asn Val Ser Gly Arg Arg Phe Glu Thr Trp Lys Asn Thr Leu Asp Arg
45                  50                  55                  60 tac cca gac acc ttg ctg ggc agc tcg gag a ag gaa ttc ttc tac gat    484
Tyr Pro Asp Thr Leu Leu Gly Ser Ser Glu Lys Glu Phe Phe Tyr Asp
                65                  70                  75 gct gac tca ggc gag tac ttc ttc gat cgc g ac cct gac atg ttc cgc    532
Ala Asp Ser Gly Glu Tyr Phe Phe Asp Arg Asp Pro Asp Met Phe Arg
            80                  85                  90 cat gtg ctg aac ttc tac cga acg ggc cgg c tg cat tgc cca cgg cag    580
His Val Leu Asn Phe Tyr Arg Thr Gly Arg Leu His Cys Pro Arg Gln
        95                  100                 105 gag tgc atc cag gcc ttc gac gaa gag ctg g ct ttc tac ggc ctg gtt    628
Glu Cys Ile Gln Ala Phe Asp Glu Glu Leu Ala Phe Tyr Gly Leu Val
    110                 115                 120 ccc gag cta gtc ggt gac tgc tgc ctt gaa g ag tat cgg gac cga aag    676
Pro Glu Leu Val Gly Asp Cys Cys Leu Glu Glu Tyr Arg Asp Arg Lys
125                 130                 135                 140
```

```
aag gag aat gcc gag cgc ctg gca gag gat g ag gag gca gag cag gcc      724
Lys Glu Asn Ala Glu Arg Leu Ala Glu Asp G lu Glu Ala Glu Gln Ala
                145                 150                 155 ggg gac ggc cca gcc ctg cca gca ggc agc t cc ctg cgg cag cgg ctc      772
Gly Asp Gly Pro Ala Leu Pro Ala Gly Ser S er Leu Arg Gln Arg Leu
            160                 165                 170 tgg cgg gcc ttc gag aat cca cac acg agc a cc gca gcc ctc gtt ttc      820
Trp Arg Ala Phe Glu Asn Pro His Thr Ser T hr Ala Ala Leu Val Phe
        175                 180                 185 tac tat gtg acc ggc ttc ttc atc gcc gtg t cg gtc atc gcc aat gtg      868
Tyr Tyr Val Thr Gly Phe Phe Ile Ala Val S er Val Ile Ala Asn Val
    190                 195                 200 gtg gag acc atc cca tgc cgc ggc tct gca c gc agg tcc tca agg gag      916
Val Glu Thr Ile Pro Cys Arg Gly Ser Ala A rg Arg Ser Ser Arg Glu
205                 210                 215                 220 cag ccc tgt ggc gaa cgc ttc cca cag gcc t tt ttc tgc atg gac aca      964
Gln Pro Cys Gly Glu Arg Phe Pro Gln Ala P he Phe Cys Met Asp Thr
                225                 230                 235 gcc tgt gta ctc ata ttc aca ggt gaa tac c tc ctg cgg ctg ttt gcc     1012
Ala Cys Val Leu Ile Phe Thr Gly Glu Tyr L eu Leu Arg Leu Phe Ala
            240                 245                 250 gcc ccc agc cgt tgc cgc ttc ctg cgg agt g tc atg agc ctc atc gac     1060
Ala Pro Ser Arg Cys Arg Phe Leu Arg Ser V al Met Ser Leu Ile Asp
        255                 260                 265 gtg gtg gcc atc ctg ccc tac tac att ggg c tt ttg gtg ccc aag aac     1108
Val Val Ala Ile Leu Pro Tyr Tyr Ile Gly L eu Leu Val Pro Lys Asn
    270                 275                 280 gac gat gtc tct ggc gcc ttt gtc acc ctg c gt gtg ttc cgg gtg ttt     1156
Asp Asp Val Ser Gly Ala Phe Val Thr Leu A rg Val Phe Arg Val Phe
285                 290                 295                 300 cgc atc ttc aag ttc tcc agg cac tca cag g gc ttg agg att ctg ggc     1204
Arg Ile Phe Lys Phe Ser Arg His Ser Gln G ly Leu Arg Ile Leu Gly
                305                 310                 315 tac aca ctc aag agc tgt gcc tct gag ctg g gc ttt ctc ctc ttt tcc     1252
Tyr Thr Leu Lys Ser Cys Ala Ser Glu Leu G ly Phe Leu Leu Phe Ser
            320                 325                 330 cta acc atg gcc atc atc atc ttt gcc act g tc atg ttt tat gct gag     1300
Leu Thr Met Ala Ile Ile Ile Phe Ala Thr V al Met Phe Tyr Ala Glu
        335                 340                 345 aag ggc aca aac aag acc aac ttt aca agc a tc cct gcg gcc ttc tgg     1348
Lys Gly Thr Asn Lys Thr Asn Phe Thr Ser I le Pro Ala Ala Phe Trp
    350                 355                 360 tat acc att gtc acc atg acc acg ctt ggc t ac gga gac atg gtg ccc     1396
Tyr Thr Ile Val Thr Met Thr Thr Leu Gly T yr Gly Asp Met Val Pro
365                 370                 375                 380 agc acc att gct ggc aag att ttc ggg tcc a tc tgc tca ctc agt ggc     1444
Ser Thr Ile Ala Gly Lys Ile Phe Gly Ser I le Cys Ser Leu Ser Gly
                385                 390                 395 gtc ttg gtc att gcc ctg cct gtg cca gtc a tt gtg tcc aac ttt agc     1492
Val Leu Val Ile Ala Leu Pro Val Pro Val I le Val Ser Asn Phe Ser
            400                 405                 410 cgc atc tac cac cag aac cag cgg gct gac a ag cgc cga gca cag cag     1540
Arg Ile Tyr His Gln Asn Gln Arg Ala Asp L ys Arg Arg Ala Gln Gln
        415                 420                 425 aag gtg cgc ttg gca agg atc cga ttg gca a ag agt ggt acc acc aat     1588
Lys Val Arg Leu Ala Arg Ile Arg Leu Ala L ys Ser Gly Thr Thr Asn
    430                 435                 440 gcc ttc ctg cag tac aag cag aat ggg ggc c tt gag gac agc ggc agt     1636
Ala Phe Leu Gln Tyr Lys Gln Asn Gly Gly L eu Glu Asp Ser Gly Ser
445                 450                 455                 460
```

```
ggc gag gaa cag gct ctt tgt gtc agg aac c gt tct gcc ttt gaa cag      1684
Gly Glu Glu Gln Ala Leu Cys Val Arg Asn A rg Ser Ala Phe Glu Gln
                465                 470                 475 caa cat cac cac ttg ctg cac tgt cta gag a ag aca acg tgc cat gag      1732
Gln His His His Leu Leu His Cys Leu Glu L ys Thr Thr Cys His Glu
                480                 485                 490 ttc aca gat gag ctc acc ttc agt gaa gcc c tg gga gcc gtc tcg ccg      1780
Phe Thr Asp Glu Leu Thr Phe Ser Glu Ala L eu Gly Ala Val Ser Pro
            495                 500                 505 ggt ggc cgc acc agc cgt agc acc tct gtg t ct tcc cag cca gtg gga      1828
Gly Gly Arg Thr Ser Arg Ser Thr Ser Val S er Ser Gln Pro Val Gly
510                 515                 520 ccc gga agc ctg ctg tct tct tgc tgc cct c gc agg gcc aag cgc cgc      1876
Pro Gly Ser Leu Leu Ser Ser Cys Cys Pro A rg Arg Ala Lys Arg Arg
525                 530                 535                 540 gcc atc cgc ctt gcc aac tcc act gcc tca g tc agc cgt ggc agc atg      1924
Ala Ile Arg Leu Ala Asn Ser Thr Ala Ser V al Ser Arg Gly Ser Met
                545                 550                 555 cag gag ctg gac atg ctg gca ggg ctg cgc a gg agc cat gcc cct cag      1972
Gln Glu Leu Asp Met Leu Ala Gly Leu Arg A rg Ser His Ala Pro Gln
                560                 565                 570 agc cgc tcc agc ctc aat gcc aag ccc cat g ac agc ctt gac ctg aac      2020
Ser Arg Ser Ser Leu Asn Ala Lys Pro His A sp Ser Leu Asp Leu Asn
                575                 580                 585 tgc gac agc cgg gac ttc gtg gct gcc att a tc agc atc cct acc cct      2068
Cys Asp Ser Arg Asp Phe Val Ala Ala Ile I le Ser Ile Pro Thr Pro
            590                 595                 600 cct gcc aac acc cca gat gag agc caa cct t cc tcc cct ggc ggc ggt      2116
Pro Ala Asn Thr Pro Asp Glu Ser Gln Pro S er Ser Pro Gly Gly Gly
605                 610                 615                 620 ggc agg gcc ggc agc acc ctc agg aac tcc a gc ctg ggt acc cct tgc      2164
Gly Arg Ala Gly Ser Thr Leu Arg Asn Ser S er Leu Gly Thr Pro Cys
                625                 630                 635 ctc ttc ccc gag act gtc aag atc tca tcc c    tgtgagggt aggcctgctg    2215
Leu Phe Pro Glu Thr Val Lys Ile Ser Ser
                640                 645 attcagaggg tcctcttcat ttttgggaac tcctttccaa agccatattt t tgggaggca    2275 gagaggggca ggcttgggca cccctttctgc ccccccact gagaactatg c aatggagtt   2335 tcatgaaatg gtccacatag tgggaagta gccaggaaat gagaaacttc c tcccacccc   2395 agacatttt cctggtggga gctgaagcac tgggcttcca caggcccctg g cctccttgc   2455 cctagcacac tgggactggc cccactctcc cagctggact cctgcatgct c ctcccttg   2515 ggctctcaga tgaaggcaaa gctttgatcc gacatctgag ctctagccta a gaaggagag  2575 ttgagatttc ctcctccctc tggctgggat atggagcttt ggaggttcag a gaagagaac  2635 cctcacctct gatctggcct ctacgagagg tcctcatctc catctggccc a caattccc   2695 agattctgaa gcttggaatg caaacacagg cttcatgggc tgtggcctct g cagcgacct  2755 gccatcccca ggccttgcct gagggtcag gctgcctctc ccaacacaca c tcagatagc   2815 acaaattcta ccatcccctt ccctggctgc tggaaatgga ccccgcaacc c tgtcctctg  2875 ctgggccccc agcaaactct agcaatagca gctgctgccg tgtcattatg c aaagcctct  2935 gaccagtttg ctgcagcatt tacatctgcc ctaatcagag gggccacctc t aactcctcc  2995 tcctcctctc ttctcctctg gttgcgtcc ttcctgggtt gggctggagt c tggactggc   3055 tgagataaga gcctggcaac cagcaagagc tgggctgtat ttggagatca t gggctgatt  3115
```

-continued

```
ccatgttctt gggcaacagt ccagaagcat caggggctcc ggcctgggat g tttctgaac       3175 tttgggagtt ataggagaca ggaggaactt ctcctcctcc tcctccccta c aattcctt       3235 tcacatattc ctttcttctc cctcttgggt gaccttccaa aactctgctc t caggctgaa       3295 atctggcatc atctcaggtt ccctgtcccc agcactgtcc ccatggagct g gtggctgac       3355 aaagatgtag tttccatcag tcaataaaac ctgagaggag agatgaggaa a aaaaaaaaa       3415 aaaaaaaaa                                                                3424
```

<210> SEQ ID NO 10
<211> LENGTH: 646
<212> TYPE: PRT
<213> ORGANISM: H. sapiens
<220> FEATURE:
<221> NAME/KEY: VARIANT
<222> LOCATION: (1)...(646)
<223> OTHER INFORMATION: Xaa = Any Amino Acid

<400> SEQUENCE: 10

```
Met Ala Ala Gly Leu Ala Thr Trp Leu Pro Phe Ala Arg Ala Ala Ala
  1               5                  10                  15

Val Gly Trp Leu Pro Pro Ala Gln Gln Pro Leu Pro Pro Ala Pro Gly
             20                  25                  30

Val Lys Ala Ser Arg Gly Asp Xaa Val Leu Val Val Asn Val Ser Gly
         35                  40                  45

Arg Arg Phe Glu Thr Trp Lys Asn Thr Leu Asp Arg Tyr Pro Asp Thr
     50                  55                  60

Leu Leu Gly Ser Ser Glu Lys Glu Phe Phe Tyr Asp Ala Asp Ser Gly
 65                  70                  75                  80

Glu Tyr Phe Phe Asp Arg Asp Pro Asp Met Phe Arg His Val Leu Asn
                 85                  90                  95

Phe Tyr Arg Thr Gly Arg Leu His Cys Pro Arg Gln Glu Cys Ile Gln
            100                 105                 110

Ala Phe Asp Glu Glu Leu Ala Phe Tyr Gly Leu Val Pro Glu Leu Val
        115                 120                 125

Gly Asp Cys Cys Leu Glu Glu Tyr Arg Asp Arg Lys Lys Glu Asn Ala
    130                 135                 140

Glu Arg Leu Ala Glu Asp Glu Glu Ala Glu Gln Ala Gly Asp Gly Pro
145                 150                 155                 160

Ala Leu Pro Ala Gly Ser Ser Leu Arg Gln Arg Leu Trp Arg Ala Phe
                165                 170                 175

Glu Asn Pro His Thr Ser Thr Ala Ala Leu Val Phe Tyr Tyr Val Thr
            180                 185                 190

Gly Phe Phe Ile Ala Val Ser Val Ile Ala Asn Val Val Glu Thr Ile
        195                 200                 205

Pro Cys Arg Gly Ser Ala Arg Arg Ser Ser Arg Glu Gln Pro Cys Gly
    210                 215                 220

Glu Arg Phe Pro Gln Ala Phe Phe Cys Met Asp Thr Ala Cys Val Leu
225                 230                 235                 240

Ile Phe Thr Gly Glu Tyr Leu Leu Arg Leu Phe Ala Ala Pro Ser Arg
                245                 250                 255

Cys Arg Phe Leu Arg Ser Val Met Ser Leu Ile Asp Val Val Ala Ile
            260                 265                 270

Leu Pro Tyr Tyr Ile Gly Leu Leu Val Pro Lys Asn Asp Asp Val Ser
        275                 280                 285

Gly Ala Phe Val Thr Leu Arg Val Phe Arg Val Phe Arg Ile Phe Lys
```

```
                    290                 295                 300
Phe Ser Arg His Ser Gln Gly Leu Arg Ile L eu Gly Tyr Thr Leu Lys
305                 310                 315                 320

Ser Cys Ala Ser Glu Leu Gly Phe Leu Leu P he Ser Leu Thr Met Ala
                325                 330                 335

Ile Ile Ile Phe Ala Thr Val Met Phe Tyr A la Glu Lys Gly Thr Asn
                340                 345                 350

Lys Thr Asn Phe Thr Ser Ile Pro Ala Ala P he Trp Tyr Thr Ile Val
                355                 360                 365

Thr Met Thr Thr Leu Gly Tyr Gly Asp Met V al Pro Ser Thr Ile Ala
370                 375                 380

Gly Lys Ile Phe Gly Ser Ile Cys Ser Leu S er Gly Val Leu Val Ile
385                 390                 395                 400

Ala Leu Pro Val Pro Val Ile Val Ser Asn P he Ser Arg Ile Tyr His
                405                 410                 415

Gln Asn Gln Arg Ala Asp Lys Arg Ala G ln Gln Lys Val Arg Leu
                420                 425                 430

Ala Arg Ile Arg Leu Ala Lys Ser Gly Thr T hr Asn Ala Phe Leu Gln
                435                 440                 445

Tyr Lys Gln Asn Gly Gly Leu Glu Asp Ser G ly Ser Gly Glu Glu Gln
450                 455                 460

Ala Leu Cys Val Arg Asn Arg Ser Ala Phe G lu Gln Gln His His His
465                 470                 475                 480

Leu Leu His Cys Leu Glu Lys Thr Thr Cys H is Glu Phe Thr Asp Glu
                485                 490                 495

Leu Thr Phe Ser Glu Ala Leu Gly Ala Val S er Pro Gly Gly Arg Thr
                500                 505                 510

Ser Arg Ser Thr Ser Val Ser Ser Gln Pro V al Gly Pro Gly Ser Leu
                515                 520                 525

Leu Ser Ser Cys Cys Pro Arg Arg Ala Lys A rg Arg Ala Ile Arg Leu
530                 535                 540

Ala Asn Ser Thr Ala Ser Val Ser Arg Gly S er Met Gln Glu Leu Asp
545                 550                 555                 560

Met Leu Ala Gly Leu Arg Arg Ser His Ala P ro Gln Ser Arg Ser Ser
                565                 570                 575

Leu Asn Ala Lys Pro His Asp Ser Leu Asp L eu Asn Cys Asp Ser Arg
                580                 585                 590

Asp Phe Val Ala Ala Ile Ile Ser Ile Pro T hr Pro Pro Ala Asn Thr
                595                 600                 605

Pro Asp Glu Ser Gln Pro Ser Pro Gly G ly Gly Gly Arg Ala Gly
                610                 615                 620

Ser Thr Leu Arg Asn Ser Ser Leu Gly Thr P ro Cys Leu Phe Pro Glu
625                 630                 635                 640

Thr Val Lys Ile Ser Ser
                645

<210> SEQ ID NO 11
<211> LENGTH: 1862
<212> TYPE: DNA
<213> ORGANISM: H. sapiens
<220> FEATURE:
<221> NAME/KEY: CDS
<222> LOCATION: (383)...(1157)
<223> OTHER INFORMATION: K+Hnov15

<400> SEQUENCE: 11
```

```
cagctgaatg tggaggcctt taagagaact tccagctcct gtaaaaaccc a gaccagagg        60 actactgacc aacatttcag gctgatcctc cagacctcga agttactctc c ttactctcc      120 tgactcttaa ttacatcaca cctgtgtcga cactctctgg gaaaagactg a agaaataat      180 cttttcaaga agcagaaagc tcctgcatac ataggctgat acgccaccta c tgcaaaacc      240 gagctgacag cgcaggcgat gctgccagcg tttccattcc atcaccaggc t ggggctgaa      300 taaaggcgtg cttgtgtggt agtgtctctt tttaaaaaat ctcaaagcca a aagaacaa       360 gctgaaatag catcttcaaa aa atg gag cgt aaa ata aa c aga aga gaa aaa      412
              Met Glu Arg Lys Ile Asn A rg Arg Glu Lys
                   1               5                  10 gaa aag gag tat gaa ggg aaa cac aac agc c tg gaa gat act gat caa        460
Glu Lys Glu Tyr Glu Gly Lys His Asn Ser L eu Glu Asp Thr Asp Gln
            15                  20                       25 gga aag aac tgc aaa tcc aca ctg atg acc c tc aac gtt ggt gga tat        508
Gly Lys Asn Cys Lys Ser Thr Leu Met Thr L eu Asn Val Gly Gly Tyr
                30                  35                  40 tta tac att act caa aaa caa aca ctg acc a ag tac cca gac act ttc        556
Leu Tyr Ile Thr Gln Lys Gln Thr Leu Thr L ys Tyr Pro Asp Thr Phe
            45                  50                       55 ctt gaa ggt ata gta aat gga aaa atc ctc t gc ccg ttt gat gct gat        604
Leu Glu Gly Ile Val Asn Gly Lys Ile Leu C ys Pro Phe Asp Ala Asp
        60                  65                    70 ggt cat tat ttc ata gac agg gat ggt ctc c tc ttc agg cat gtc cta        652
Gly His Tyr Phe Ile Asp Arg Asp Gly Leu L eu Phe Arg His Val Leu
 75                  80                   85                    90 aac ttc cta cga aat gga gaa ctt cta ttg c cc gaa ggg ttt cga gaa        700
Asn Phe Leu Arg Asn Gly Glu Leu Leu Leu P ro Glu Gly Phe Arg Glu
                95                  100                  105 aat caa ctt ctt gca caa gaa gca gaa ttc t tt cag ctc aag gga ctg        748
Asn Gln Leu Leu Ala Gln Glu Ala Glu Phe P he Gln Leu Lys Gly Leu
            110                  115                     120 gca gag gaa gtg aaa tcc agg tgg gag aaa g aa cag cta aca ccc aga        796
Ala Glu Glu Val Lys Ser Arg Trp Glu Lys G lu Gln Leu Thr Pro Arg
            125                  130                     135 gag act act ttc ttg gaa ata aca gat aac c ac gat cgt tca caa gga        844
Glu Thr Thr Phe Leu Glu Ile Thr Asp Asn H is Asp Arg Ser Gln Gly
        140                  145                   150 tta aga atc ttc tgt aat gct cct gat ttc a ta tca aaa ata aag tct        892
Leu Arg Ile Phe Cys Asn Ala Pro Asp Phe I le Ser Lys Ile Lys Ser
155                  160                  165                   170 cgc att gtt ctg gtg tcc aaa agc agg ctg g at gga ttt cca gag gag        940
Arg Ile Val Leu Val Ser Lys Ser Arg Leu A sp Gly Phe Pro Glu Glu
                175                  180                  185 ttt tca ata tcg tca aat atc atc caa ttt a aa tac ttc ata aag tct        988
Phe Ser Ile Ser Ser Asn Ile Ile Gln Phe L ys Tyr Phe Ile Lys Ser
            190                  195                     200 gaa aat ggc act cga ctt gta cta aag gaa g ac aac acc ttt gtc tgt       1036
Glu Asn Gly Thr Arg Leu Val Leu Lys Glu A sp Asn Thr Phe Val Cys
            205                  210                     215 acc ttg gaa act ctt aag ttt gag gct atc a tg atg gct tta aag tgt       1084
Thr Leu Glu Thr Leu Lys Phe Glu Ala Ile M et Met Ala Leu Lys Cys
        220                  225                   230 ggc ttt aga ctg ctg acc agc ctg gat tgt t cc aaa ggg tca att gtt       1132
Gly Phe Arg Leu Leu Thr Ser Leu Asp Cys S er Lys Gly Ser Ile Val
235                  240                  245                   250 cac agc gat gca ctt cat ttt atc a agtaattacc tgtgtcacga              1177
His Ser Asp Ala Leu His Phe Ile
```

```
acaaaggcaa caagcatgca gccagcaagc ttcggaaaac cacagcatca a agacatccc   1237 aaataacatg cccagctagc tctgtactac agagccctgc tactaatcaa t tactgtgag   1297 ctaacggtat gtaaattcta tcgctaaaga tgtccttcct ctggggtgtt c ctactgatc   1357 agactcttcc acctaaaatg aaaacagtaa ccttctatat actgtaaata a agactgaaa   1417 gcttttgcta tttatttgtc cttaagctgt ctttcaattc agattgtctt g ggtatttgc   1477 acaaaaagaa gcatgtacat tatctatcgt tcatttaagt aaatggtaat a aaatatttt   1537 aagggctat taatatttaa aatccttttc tactatggca aaaatctaca g agaaactga   1597 actggcaaaa ttaactacct ggagcaaaac agatgtgcag atctaactaa a acagagcta   1657 tagtgaaaca aaatgagatt gtaagaagac attaaagcta ttgatttgat t tttccatag   1717 caagcaccaa aagcttatat tcacagttcc tgtgtttcat attagactta t agctgaatt   1777 ggtattttgc tgaaaattcc tagaaaactg cttgatgaca ataaaagta a ataaaagca   1837 ctgctacctt caaaaaaaaa aaaaa                                          1862
```

<210> SEQ ID NO 12
<211> LENGTH: 258
<212> TYPE: PRT
<213> ORGANISM: H. sapiens

<400> SEQUENCE: 12

```
Met Glu Arg Lys Ile Asn Arg Arg Glu Lys G lu Lys Glu Tyr Glu Gly
 1               5                  10                  15

Lys His Asn Ser Leu Glu Asp Thr Asp Gln G ly Lys Asn Cys Lys Ser
            20                  25                  30

Thr Leu Met Thr Leu Asn Val Gly Gly Tyr L eu Tyr Ile Thr Gln Lys
        35                  40                  45

Gln Thr Leu Thr Lys Tyr Pro Asp Thr Phe L eu Glu Gly Ile Val Asn
    50                  55                  60

Gly Lys Ile Leu Cys Pro Phe Asp Ala Asp G ly His Tyr Phe Ile Asp
65                  70                  75                  80

Arg Asp Gly Leu Leu Phe Arg His Val Leu A sn Phe Leu Arg Asn Gly
                85                  90                  95

Glu Leu Leu Leu Pro Glu Gly Phe Arg Glu A sn Gln Leu Leu Ala Gln
            100                 105                 110

Glu Ala Glu Phe Phe Gln Leu Lys Gly Leu A la Glu Val Lys Ser
            115                 120                 125

Arg Trp Glu Lys Glu Gln Leu Thr Pro Arg G lu Thr Thr Phe Leu Glu
        130                 135                 140

Ile Thr Asp Asn His Asp Arg Ser Gln Gly L eu Arg Ile Phe Cys Asn
145                 150                 155                 160

Ala Pro Asp Phe Ile Ser Lys Ile Lys Ser A rg Ile Val Leu Val Ser
                165                 170                 175

Lys Ser Arg Leu Asp Gly Phe Pro Glu Glu P he Ser Ile Ser Ser Asn
            180                 185                 190

Ile Ile Gln Phe Lys Tyr Phe Ile Lys Ser G lu Asn Gly Thr Arg Leu
        195                 200                 205

Val Leu Lys Glu Asp Asn Thr Phe Val Cys T hr Leu Glu Thr Leu Lys
    210                 215                 220

Phe Glu Ala Ile Met Met Ala Leu Lys Cys G ly Phe Arg Leu Leu Thr
225                 230                 235                 240
```

-continued

```
Ser Leu Asp Cys Ser Lys Gly Ser Ile Val His Ser Asp Ala Leu His
                245                 250                 255

Phe Ile

<210> SEQ ID NO 13
<211> LENGTH: 1877
<212> TYPE: DNA
<213> ORGANISM: H. sapiens
<220> FEATURE:
<221> NAME/KEY: CDS
<222> LOCATION: (322)...(1090)
<223> OTHER INFORMATION: K+Hnov27

<400> SEQUENCE: 13
caccaccgcc cccagccgcc ctcgctgggg aacacttaca tcctcccaa a gacagccag        60 gtcgggcccg acgtgaaatc cgaggctgcg cccaagcgcg ccctgtacga g tctgtgttc      120 gggtcggggg aaatctgcgg ccccacttcc cccaaaagac tttgtatccg c ccctcggag     180 cctgtggatg cggtggtggt ggtttccgtg aaacacgacc ccctgcctct t cttccagaa    240 gccaatgggc acagaagcac caattctccc acaatagttt cacctgctat t gtttccccc   300 acccaggaca gtcggcccaa t atg tca aga cct ctg atc act aga tcc cct       351
                        Met Ser Arg Pro Leu Ile Thr Arg Ser Pro
                         1               5                  10 gca tct cca ctg awc aac caa ggc atc cct a ct cca gca caa ctc aca     399
Ala Ser Pro Leu Xaa Asn Gln Gly Ile Pro T hr Pro Ala Gln Leu Thr
             15                  20                  25 aaa tcc aat gcg cct gtc cac att gat gtg g gc ggc cac atg tac acc    447
Lys Ser Asn Ala Pro Val His Ile Asp Val G ly Gly His Met Tyr Thr
         30                  35                  40 agc agc ctg gcc acc ctc acc aaa tac cct g aa tcc aga atc gga aga    495
Ser Ser Leu Ala Thr Leu Thr Lys Tyr Pro G lu Ser Arg Ile Gly Arg
     45                  50                  55 ctt ttt gat ggt aca gag ccc att gtt ttg g ac agt ctc aaa cag cac    543
Leu Phe Asp Gly Thr Glu Pro Ile Val Leu A sp Ser Leu Lys Gln His
 60                  65                  70 tat ttc att gac aga gat gga cag atg ttc a ga tat atc ttg aat ttt    591
Tyr Phe Ile Asp Arg Asp Gly Gln Met Phe A rg Tyr Ile Leu Asn Phe
 75              80                  85                  90 cta cga aca tcc aaa ctc ctc att cct gat g at ttc aag gac tac act    639
Leu Arg Thr Ser Lys Leu Leu Ile Pro Asp A sp Phe Lys Asp Tyr Thr
             95                  100                 105 ttg tta tat gaa gag gca aaa tat ttt cag c tt cag ccc atg ttg ttg    687
Leu Leu Tyr Glu Glu Ala Lys Tyr Phe Gln L eu Gln Pro Met Leu Leu
         110                 115                 120 gag atg gaa aga tgg aag cag gac aga gaa a ct ggt cga ttt tca agg    735
Glu Met Glu Arg Trp Lys Gln Asp Arg Glu T hr Gly Arg Phe Ser Arg
     125                 130                 135 ccc tgt gag tgc ctc gtc gtg cgt gtg gcc c ca gac ctc gga gaa agg    783
Pro Cys Glu Cys Leu Val Val Arg Val Ala P ro Asp Leu Gly Glu Arg
 140                 145                 150 atc acg cta agc ggt gac aaa tcc ttg ata g aa gaa gta ttt cca gag    831
Ile Thr Leu Ser Gly Asp Lys Ser Leu Ile G lu Glu Val Phe Pro Glu
155                 160                 165                 170 atc ggc gac gtg atg tgt aac tct gtc aat g ca ggc tgg aat cac gac    879
Ile Gly Asp Val Met Cys Asn Ser Val Asn A la Gly Trp Asn His Asp
                 175                 180                 185 tcg acg cac gtc atc agg ttt cca cta aat g gc tac tgt cac ctc aac    927
Ser Thr His Val Ile Arg Phe Pro Leu Asn G ly Tyr Cys His Leu Asn
             190                 195                 200
```

-continued

```
tca gtc cag gtc ctc gag agg ttg cag caa a ga gga ttt gaa atc gtg        975
Ser Val Gln Val Leu Glu Arg Leu Gln Gln A rg Gly Phe Glu Ile Val
        205                 210                 215 ggc tcc tgt ggg gga gga gta gac tcg tcc c ag ttc agc gaa tac gtc       1023
Gly Ser Cys Gly Gly Gly Val Asp Ser Ser G ln Phe Ser Glu Tyr Val
220                 225                 230 ctt cgg cgg gaa ctg agg cgg acg ccc cgt g ta ccc tcc gtc atc cgg       1071
Leu Arg Arg Glu Leu Arg Arg Thr Pro Arg V al Pro Ser Val Ile Arg
235                 240                 245                 250 ata aag caa gag cct ctg g actaaatgga catatttctt  atgcaaaaag            1120
Ile Lys Gln Glu Pro Leu
                255 gaaacacac acaaccaata actcaaacaa aaaagggaca tttatgtgca g ttgggacag      1180 caaaccaagt cctggacgta aaattgaata aaagacacat ttatatccaa t agagaccac     1240 acctgtattc atatgggaac aattggaata gtgatatcct caaggtgtaa a aaatatata    1300 aatatatata tatatgtcaa aaggtaggaa atgcaaaaaa gaaaaaaaaa a aaggtgaca    1360 gccgcagttg gtgctgtgat ggccgtgaag tgtcctgggc ctcccgaggc c tctgacaaa    1420 taaacaagcc atgagtggtg aggacacagt ctccttacag tttccattgc c aacaacagc    1480 catccatatt tcttttttcc tttgtctttc ttttttcctt ttttttaaaa a aacaaaaca    1540 aacaaaacac cttgaatcaa gtttgtttgt atatggaggt tccacgtctt t ctttaggca    1600 gggaccaggc aggacttcag aaaaaccctc atgagcacat tgcaaagatg t tagacatga   1660 aattttaaat gtagtttgta cagaagtcac actttttttgt ccacctcaca g atgtgaact  1720 ttactttgtt ttaaaactga tcagttttgc caaggggcca gaattattcc t tgttagaat   1780 tgctccagtt caagtctgct gctttcctac aattttttcaa attttataat g tattaaata  1840 caataaactc tgtttaaaaa ataaaaaaaa aaaaaaa                              1877
```

<210> SEQ ID NO 14
<211> LENGTH: 256
<212> TYPE: PRT
<213> ORGANISM: H. sapiens
<220> FEATURE:
<221> NAME/KEY: VARIANT
<222> LOCATION: (1)...(256)
<223> OTHER INFORMATION: Xaa = Any Amino Acid

<400> SEQUENCE: 14

```
Met Ser Arg Pro Leu Ile Thr Arg Ser Pro A la Ser Pro Leu Xaa Asn
1               5                   10                  15

Gln Gly Ile Pro Thr Pro Ala Gln Leu Thr L ys Ser Asn Ala Pro Val
            20                  25                  30

His Ile Asp Val Gly Gly His Met Tyr Thr S er Ser Leu Ala Thr Leu
        35                  40                  45

Thr Lys Tyr Pro Glu Ser Arg Ile Gly Arg L eu Phe Asp Gly Thr Glu
    50                  55                  60

Pro Ile Val Leu Asp Ser Leu Lys Gln His T yr Phe Ile Asp Arg Asp
65                  70                  75                  80

Gly Gln Met Phe Arg Tyr Ile Leu Asn Phe L eu Arg Thr Ser Lys Leu
                85                  90                  95

Leu Ile Pro Asp Asp Phe Lys Asp Tyr Thr L eu Leu Tyr Glu Glu Ala
            100                 105                 110

Lys Tyr Phe Gln Leu Gln Pro Met Leu Leu G lu Met Glu Arg Trp Lys
        115                 120                 125

Gln Asp Arg Glu Thr Gly Arg Phe Ser Arg P ro Cys Glu Cys Leu Val
```

```
                130              135              140
Val Arg Val Ala Pro Asp Leu Gly Glu Arg Ile Thr Leu Ser Gly Asp
145                 150                 155                 160

Lys Ser Leu Ile Glu Glu Val Phe Pro Glu Ile Gly Asp Val Met Cys
                165                 170                 175

Asn Ser Val Asn Ala Gly Trp Asn His Asp Ser Thr His Val Ile Arg
                180                 185                 190

Phe Pro Leu Asn Gly Tyr Cys His Leu Asn Ser Val Gln Val Leu Glu
            195                 200                 205

Arg Leu Gln Gln Arg Gly Phe Glu Ile Val Gly Ser Cys Gly Gly Gly
        210                 215                 220

Val Asp Ser Ser Gln Phe Ser Glu Tyr Val Leu Arg Arg Glu Leu Arg
225                 230                 235                 240

Arg Thr Pro Arg Val Pro Ser Val Ile Arg Ile Lys Gln Glu Pro Leu
                245                 250                 255

<210> SEQ ID NO 15
<211> LENGTH: 923
<212> TYPE: DNA
<213> ORGANISM: H. sapiens
<220> FEATURE:
<221> NAME/KEY: CDS
<222> LOCATION: (165)...(756)
<223> OTHER INFORMATION: K+Hnov2

<400> SEQUENCE: 15
gcgtggtggc aggtgcctgt agccccagct acttgggagg ctgaggcagg a gaatagctt      60 gaacccgggc ggcgaaggtt gagtgagccg agattgcacc actgcactcc a gcctgggcg    120 acagagcgag actccatctc aaaaaaaaga gtagttatgg ccac atg gcc cca cta      176
                                                 Met Ala Pro Leu
                                                   1 tcg cca ggc gga aag gcc ttc tgc atg gtc t at gca gcc ctg ggg ctg      224
Ser Pro Gly Gly Lys Ala Phe Cys Met Val Tyr Ala Ala Leu Gly Leu
  5                  10                  15                  20 cca gcc tcc tta gct ctc gtg gcc acc ctg c gc cat tgc ctg ctg cct      272
Pro Ala Ser Leu Ala Leu Val Ala Thr Leu Arg His Cys Leu Leu Pro
                 25                  30                  35 gtg ctc agc cgc cca cgt gcc tgg gta gcg g tc cac tgg cag ctg tca      320
Val Leu Ser Arg Pro Arg Ala Trp Val Ala Val His Trp Gln Leu Ser
             40                  45                  50 ccg gcc agg gct gcg ctg ctg cag gca gtt g ca ctg gga ctg ctg gtg      368
Pro Ala Arg Ala Ala Leu Leu Gln Ala Val Ala Leu Gly Leu Leu Val
         55                  60                  65 gcc agc agc ttt gtg ctg ctg cca gcg ctg g tg ctg tgg ggc ctt cag      416
Ala Ser Ser Phe Val Leu Leu Pro Ala Leu Val Leu Trp Gly Leu Gln
     70                  75                  80 ggc gac tgc agc ctg ctg ggg gcc gtc tac t tc tgc ttc agc tcg ctc      464
Gly Asp Cys Ser Leu Leu Gly Ala Val Tyr Phe Cys Phe Ser Ser Leu
 85                  90                  95                 100 agc acc att ggc ctg gag gac ttg ctg ccc g gc cgc ggc cgc agc ctg      512
Ser Thr Ile Gly Leu Glu Asp Leu Leu Pro Gly Arg Gly Arg Ser Leu
                105                 110                 115 cac ccc gtg att tac cac ctg ggc cag ctc g ca ctt ctt ggt tac ttg      560
His Pro Val Ile Tyr His Leu Gly Gln Leu Ala Leu Leu Gly Tyr Leu
            120                 125                 130 ctt cta gga ctc ttg gcc atg ctg ctg gca g tg gag acc ttc tct gag      608
Leu Leu Gly Leu Leu Ala Met Leu Leu Ala Val Glu Thr Phe Ser Glu
        135                 140                 145
```

```
ctg ccg cag gtc cgt gcc atg ggg aag ttc t tc aga ccc agt ggt cct    656
Leu Pro Gln Val Arg Ala Met Gly Lys Phe P he Arg Pro Ser Gly Pro
    150                 155                 160 gtg act gct gag gac caa ggt ggc atc cta g gg cag gat gaa ctg gct    704
Val Thr Ala Glu Asp Gln Gly Gly Ile Leu G ly Gln Asp Glu Leu Ala
165                 170                 175                 180 ctg agc acc ctg ccg ccc gcg gcc cca gct t ca gga caa gcc cct gct    752
Leu Ser Thr Leu Pro Pro Ala Pro Ala S er Gly Gln Ala Pro Ala
                185                 190                 195 tgc t gaagcgtcag gtgaccgagt tcagctccgt aaggtggcgg cac ctgagga       806
Cys ggaagcagcc aggagtggct ggggaagaat ctggagatgg agccgcggtg a gggtgggcg  866 ggaggcctca gggatactg ttaatcataa aaaaaaaaa aaaaaaaaaa a aaaaa        923
```

<210> SEQ ID NO 16
<211> LENGTH: 197
<212> TYPE: PRT
<213> ORGANISM: H. sapiens

<400> SEQUENCE: 16

```
Met Ala Pro Leu Ser Pro Gly Gly Lys Ala P he Cys Met Val Tyr Ala
1               5                   10                  15

Ala Leu Gly Leu Pro Ala Ser Leu Ala Leu V al Ala Thr Leu Arg His
            20                  25                  30

Cys Leu Leu Pro Val Leu Ser Arg Pro Arg A la Trp Val Ala Val His
        35                  40                  45

Trp Gln Leu Ser Pro Ala Arg Ala Ala Leu L eu Gln Ala Val Ala Leu
    50                  55                  60

Gly Leu Leu Val Ala Ser Ser Phe Val Leu L eu Pro Ala Leu Val Leu
65                  70                  75                  80

Trp Gly Leu Gln Gly Asp Cys Ser Leu Leu G ly Ala Val Tyr Phe Cys
                85                  90                  95

Phe Ser Ser Leu Ser Thr Ile Gly Leu Glu A sp Leu Leu Pro Gly Arg
            100                 105                 110

Gly Arg Ser Leu His Pro Val Ile Tyr His L eu Gly Gln Leu Ala Leu
        115                 120                 125

Leu Gly Tyr Leu Leu Leu Gly Leu Leu Ala M et Leu Leu Ala Val Glu
    130                 135                 140

Thr Phe Ser Glu Leu Pro Gln Val Arg Ala M et Gly Lys Phe Phe Arg
145                 150                 155                 160

Pro Ser Gly Pro Val Thr Ala Glu Asp Gln G ly Gly Ile Leu Gly Gln
                165                 170                 175

Asp Glu Leu Ala Leu Ser Thr Leu Pro Pro A la Ala Pro Ala Ser Gly
            180                 185                 190

Gln Ala Pro Ala Cys
        195
```

<210> SEQ ID NO 17
<211> LENGTH: 3102
<212> TYPE: DNA
<213> ORGANISM: H. sapiens
<220> FEATURE:
<221> NAME/KEY: CDS
<222> LOCATION: (274)...(1705)
<223> OTHER INFORMATION: K+Hnov11

<400> SEQUENCE: 17

```
gcacgcgcaa agcgcccacc gagacccctg gggtggagct tgtgttaata g aaacatacc   60
```

```
cacccccagc ctttcctggg aggggatcag acccctcaaa ctcttgcccc a gcccagccc      120 ttcagcaccc aagacccacc aggaggcctg ggcccgccag taatgggtag g gagaggggg      180 ccccgccagg gcgcacggcg ctctcgccga cgctgttccc tccgcttcca g gtgtagcgc      240 ccccgcgcgg cgcgggcggc cggcgcctcc agc atg acc ggc c ag agc ctg tgg      294
                                    Met Thr Gly Gln Ser Leu Trp
                                     1               5 gac gtg tcg gag gct aac gtc gag gac ggg g ag atc cgc atc aat gtg      342
Asp Val Ser Glu Ala Asn Val Glu Asp Gly G lu Ile Arg Ile Asn Val
         10                  15                  20 ggc ggc ttc aag agg agg ctg cgc tcg cac a cg ctg ctg cgc ttc ccc      390
Gly Gly Phe Lys Arg Arg Leu Arg Ser His T hr Leu Leu Arg Phe Pro
     25                  30                  35 gag acg cgc ctg ggc cgc ttg ctg ctc tgc c ac tcg cgc gag gcc att      438
Glu Thr Arg Leu Gly Arg Leu Leu Leu Cys H is Ser Arg Glu Ala Ile
 40                  45                  50                  55 ctg gag ctc tgc gat gac tac gac gac gtc c ag cgg gag ttc tac ttc      486
Leu Glu Leu Cys Asp Asp Tyr Asp Asp Val G ln Arg Glu Phe Tyr Phe
                 60                  65                  70 gac cgc aac cct gag ctc ttc ccc tac gtg c tg cat ttc tat cac acc      534
Asp Arg Asn Pro Glu Leu Phe Pro Tyr Val L eu His Phe Tyr His Thr
             75                  80                  85 ggc aag ctt cac gtc atg gct gag cta tgt g tc ttc tcc ttc agc cag      582
Gly Lys Leu His Val Met Ala Glu Leu Cys V al Phe Ser Phe Ser Gln
         90                  95                 100 gag atc gag tac tgg ggc atc aac gag ttc t tc att gac tcc tgc tgc      630
Glu Ile Glu Tyr Trp Gly Ile Asn Glu Phe P he Ile Asp Ser Cys Cys
    105                 110                 115 agc tac agc tac cat ggc cgc aaa gta gag c cc gag cag gag aag tgg      678
Ser Tyr Ser Tyr His Gly Arg Lys Val Glu P ro Glu Gln Glu Lys Trp
120                 125                 130                 135 gac gag cag agt gac cag gag agc acc acg t ct tcc ttc gat gag atc      726
Asp Glu Gln Ser Asp Gln Glu Ser Thr Thr S er Ser Phe Asp Glu Ile
                140                 145                 150 ctt gcc ttc tac aac gac gcc tcc aag ttc g at ggg cag ccc ctc ggc      774
Leu Ala Phe Tyr Asn Asp Ala Ser Lys Phe A sp Gly Gln Pro Leu Gly
            155                 160                 165 aac ttc cgc agg cag ctg tgg ctg gcg ctg g ac aac ccc ggc tac tca      822
Asn Phe Arg Arg Gln Leu Trp Leu Ala Leu A sp Asn Pro Gly Tyr Ser
        170                 175                 180 gtg ctg agc agg gtc ttc agc atc ctg tcc a tc ctg gtg gtg atg ggg      870
Val Leu Ser Arg Val Phe Ser Ile Leu Ser I le Leu Val Val Met Gly
    185                 190                 195 tcc atc atc acc atg tgc ctc aat agc ctg c cc gat ttc caa atc cct      918
Ser Ile Ile Thr Met Cys Leu Asn Ser Leu P ro Asp Phe Gln Ile Pro
200                 205                 210                 215 gac agc cag ggc aac cct ggc gag gac cct a gg ttc gaa atc gtg gag      966
Asp Ser Gln Gly Asn Pro Gly Glu Asp Pro A rg Phe Glu Ile Val Glu
                220                 225                 230 cac ttt ggc att gcc tgg ttc aca ttt gag c tg gtg gcc agg ttt gct     1014
His Phe Gly Ile Ala Trp Phe Thr Phe Glu L eu Val Ala Arg Phe Ala
            235                 240                 245 gtg gcc cct gac ttc ctc aag ttc ttc aag a at gcc cta aac ctt att     1062
Val Ala Pro Asp Phe Leu Lys Phe Phe Lys A sn Ala Leu Asn Leu Ile
        250                 255                 260 gac ctc atg tcc atc gtc ccc ttt tac atc a ct ctg gtg gtg aac ctg     1110
Asp Leu Met Ser Ile Val Pro Phe Tyr Ile T hr Leu Val Val Asn Leu
    265                 270                 275
```

-continued

| | |
|---|---|
| gtg gtg gag agc aca cct act tta gcc aac t tg ggc agg gtg gcc cag<br>Val Val Glu Ser Thr Pro Thr Leu Ala Asn L eu Gly Arg Val Ala Gln<br>280               285               290               295 | 1158 |
| gtc ctg agg ctg atg cgg atc ttc cgc atc t ta aag ctg gcc agg cac<br>Val Leu Arg Leu Met Arg Ile Phe Arg Ile L eu Lys Leu Ala Arg His<br>300                      305               310 | 1206 |
| tcc act ggc ctc cgc tcc ctg ggg gcc act t tg aaa tac agc tac aaa<br>Ser Thr Gly Leu Arg Ser Leu Gly Ala Thr L eu Lys Tyr Ser Tyr Lys<br>315                 320               325 | 1254 |
| gaa gta ggg ctg ctc ttg ctc tac ctc tcc g tg ggg att tcc atc ttc<br>Glu Val Gly Leu Leu Leu Leu Tyr Leu Ser V al Gly Ile Ser Ile Phe<br>330                     335               340 | 1302 |
| tcc gtg gtg gcc tac acc att gaa aag gag g ag aac gag ggc ctg gcc<br>Ser Val Val Ala Tyr Thr Ile Glu Lys Glu G lu Asn Glu Gly Leu Ala<br>345               350               355 | 1350 |
| acc atc cct gcc tgc tgg tgg tgg gct acc g tc agt atg acc aca gtg<br>Thr Ile Pro Ala Cys Trp Trp Trp Ala Thr V al Ser Met Thr Thr Val<br>360                     365               370               375 | 1398 |
| ggg tac ggg gat gtg gtc cca ggg acc acg g ca gga aag ctg act gcc<br>Gly Tyr Gly Asp Val Val Pro Gly Thr Thr A la Gly Lys Leu Thr Ala<br>380               385               390 | 1446 |
| tct gcc tgc atc ttg gca ggc atc ctc gtg g tg gtc ctg ccc atc acc<br>Ser Ala Cys Ile Leu Ala Gly Ile Leu Val V al Val Leu Pro Ile Thr<br>395                     400               405 | 1494 |
| ttg atc ttc aat aag ttc tcc cac ttt tac c gg cgc caa aag caa ctt<br>Leu Ile Phe Asn Lys Phe Ser His Phe Tyr A rg Arg Gln Lys Gln Leu<br>410                     415               420 | 1542 |
| gag agt gcc atg cgc agc tgt gac ttt gga g at gga atg aag gag gtc<br>Glu Ser Ala Met Arg Ser Cys Asp Phe Gly A sp Gly Met Lys Glu Val<br>425                     430               435 | 1590 |
| cct tcg gtc aat tta agg gac tat tat gcc c at aaa gtt aaa tcc ctt<br>Pro Ser Val Asn Leu Arg Asp Tyr Tyr Ala H is Lys Val Lys Ser Leu<br>440                     445               450               455 | 1638 |
| atg gca agc ctg acg aac atg agc agg agc t ca cca agt gaa ctc agt<br>Met Ala Ser Leu Thr Asn Met Ser Arg Ser S er Pro Ser Glu Leu Ser<br>460                     465               470 | 1686 |
| tta aat gat tcc cta cgt t agccgggagg acttgtcacc ctccaccccA<br>Leu Asn Asp Ser Leu Arg<br>475 | 1735 |
| cattgctgag ctgcctcttg tgcctctggc acagcccagg caccttatgg t tatggtgta | 1795 |
| aggagtatgc ccagcccctg aggggagaga tgcatgggat atgcacccag g tttcttta | 1855 |
| cagttttag aatcgttttt agagggtggt gtgtctgaca ccatgccttt g cacctttcc | 1915 |
| atgaaatgac actcactggt ctttgcatcg tgggcataaa atgttcacct t ttttccaga | 1975 |
| tgagtacacc cagaatgcta attttctgt ccatcgtgta cgctattcta g tgcttgtgg | 2035 |
| cccagtactg tctatgagtt gtcgtgctcc tgtttctgag gttgtcgtgt g agttctgta | 2095 |
| caaaaagccc ccacaagtcg tccagtagaa atgcatctat gaggtcagca a ggatatgat | 2155 |
| gagattttgc tcacagtcat gtgaaaacaa aatcttcagct ctttatccat t gctttcact | 2215 |
| tagttttagt accaaaacaa agagaatgca aagttaagca gacttgacca a tgcaagtct | 2275 |
| ctaagttgtt tttataaatg atctgtagtt ccgtggcttg catgggtgca c caatcatct | 2335 |
| ttagaacgat gtacactgat gttcatctca taaatgtcac tctttagaga a tgttactta | 2395 |
| gttaaacatg cagtgaagat cgaatttttt tcccaagaac agatgtgtta g ggagagggg | 2455 |
| cttcagctaa atagtccaaa ccctagggtg cttaaagcca agttagtgca g gctgagccc | 2515 |
| cttggttcac agtcaagcct ccttgtttcc tagggtgact gtagagaaat g tatttccgg | 2575 |

-continued

```
atgaggtttc tgatctaggc catttgacca aactttgctg tgtctaagat a ttagcatgt    2635 ttttgaaata tttattttt aagatgttta ggagtaaggt cgtgttgtct t cctcaacta    2695 aaaagaagtt tactgttgta tcgtctccct gaggtgaacg ttgttgggtt g ctagcaagg   2755 cagtagctta atactttgt tgcctactct gaaagctcat caatgagagc c cttttattt    2815 ccaagcagaa tttagtcaga taattttgct tctaggatat agtatgttgt a tatgatgct   2875 gtgattgccc tggagttcct gcccatgact ggaaacctgg tggtatggaa g catgtactc   2935 aaaatataga cgtgcacgat ggtggtgtgg cttacccagg atggaaacac t gcagttctt   2995 acttgcattc ccactgcctt tcatgggggg tgactgggta gaggccagga g aaaggaaag   3055 agttgtaaaa taaaaaactg ctagttcata aaaaaaaaa aaaaaaa                   3102
```

<210> SEQ ID NO 18
<211> LENGTH: 477
<212> TYPE: PRT
<213> ORGANISM: H. sapiens

<400> SEQUENCE: 18

Met Thr Gly Gln Ser Leu Trp Asp Val Ser G lu Ala Asn Val Glu Asp
 1               5                  10                  15

Gly Glu Ile Arg Ile Asn Val Gly Gly Phe L ys Arg Arg Leu Arg Ser
             20                  25                  30

His Thr Leu Leu Arg Phe Pro Glu Thr Arg L eu Gly Arg Leu Leu Leu
         35                  40                  45

Cys His Ser Arg Glu Ala Ile Leu Glu Leu C ys Asp Asp Tyr Asp Asp
     50                  55                  60

Val Gln Arg Glu Phe Tyr Phe Asp Arg Asn P ro Glu Leu Phe Pro Tyr
 65                  70                  75                  80

Val Leu His Phe Tyr His Thr Gly Lys Leu H is Val Met Ala Glu Leu
                 85                  90                  95

Cys Val Phe Ser Phe Ser Gln Glu Ile Glu T yr Trp Gly Ile Asn Glu
            100                 105                 110

Phe Phe Ile Asp Ser Cys Cys Ser Tyr Ser T yr His Gly Arg Lys Val
        115                 120                 125

Glu Pro Glu Gln Glu Lys Trp Asp Glu Gln S er Asp Gln Glu Ser Thr
    130                 135                 140

Thr Ser Ser Phe Asp Glu Ile Leu Ala Phe T yr Asn Asp Ala Ser Lys
145                 150                 155                 160

Phe Asp Gly Gln Pro Leu Gly Asn Phe Arg A rg Gln Leu Trp Leu Ala
                165                 170                 175

Leu Asp Asn Pro Gly Tyr Ser Val Leu Ser A rg Val Phe Ser Ile Leu
            180                 185                 190

Ser Ile Leu Val Val Met Gly Ser Ile Ile T hr Met Cys Leu Asn Ser
        195                 200                 205

Leu Pro Asp Phe Gln Ile Pro Asp Ser Gln G ly Asn Pro Gly Glu Asp
    210                 215                 220

Pro Arg Phe Glu Ile Val Glu His Phe Gly I le Ala Trp Phe Thr Phe
225                 230                 235                 240

Glu Leu Val Ala Arg Phe Ala Val Ala Pro A sp Phe Leu Lys Phe Phe
                245                 250                 255

Lys Asn Ala Leu Asn Leu Ile Asp Leu Met S er Ile Val Pro Phe Tyr
            260                 265                 270

Ile Thr Leu Val Val Asn Leu Val Val Glu S er Thr Pro Thr Leu Ala

```
                275                 280                 285
Asn Leu Gly Arg Val Ala Gln Val Leu Arg Leu Met Arg Ile Phe Arg
    290                 295                 300
Ile Leu Lys Leu Ala Arg His Ser Thr Gly Leu Arg Ser Leu Gly Ala
305                 310                 315                 320
Thr Leu Lys Tyr Ser Tyr Lys Glu Val Gly Leu Leu Leu Tyr Leu
                325                 330                 335
Ser Val Gly Ile Ser Ile Phe Ser Val Ala Tyr Thr Ile Glu Lys
            340                 345                 350
Glu Glu Asn Glu Gly Leu Ala Thr Ile Pro Ala Cys Trp Trp Ala
            355                 360                 365
Thr Val Ser Met Thr Thr Val Gly Tyr Gly Asp Val Val Pro Gly Thr
    370                 375                 380
Thr Ala Gly Lys Leu Thr Ala Ser Ala Cys Ile Leu Ala Gly Ile Leu
385                 390                 395                 400
Val Val Val Leu Pro Ile Thr Leu Ile Phe Asn Lys Phe Ser His Phe
                405                 410                 415
Tyr Arg Gln Lys Gln Leu Glu Ser Ala Met Arg Ser Cys Asp Phe
            420                 425                 430
Gly Asp Gly Met Lys Glu Val Pro Ser Val Asn Leu Arg Asp Tyr Tyr
            435                 440                 445
Ala His Lys Val Lys Ser Leu Met Ala Ser Leu Thr Asn Met Ser Arg
    450                 455                 460
Ser Ser Pro Ser Glu Leu Ser Leu Asn Asp Ser Leu Arg
465                 470                 475

<210> SEQ ID NO 19
<211> LENGTH: 3857
<212> TYPE: DNA
<213> ORGANISM: H. sapiens
<220> FEATURE:
<221> NAME/KEY: CDS
<222> LOCATION: (249)...(3495)
<223> OTHER INFORMATION: K+Hnov14

<400> SEQUENCE: 19
gggctggtag cagggatttg tgggcggcga gggcgcgagg ggccgcgcgc c atgctccgg      60 gccccgacgg cgcggacgcc ccctcgcgcg ccagctccgg cgcgaccccg g atcccggtc    120 tgcgcattgc ccccgacgg ctgcgctagg agcgcgggc ccggcggggg c ggccgagct     180 gggcgccctc ccccggcgcg gagtccccgc accccggagg atgggcggg c agccgcggg   240 cgcctaag atg ccg gcc atg cgg ggc ctc ctg gcg ccg cag aac acc ttc     290
         Met Pro Ala Met Arg Gly Leu Leu Ala Pro Gln Asn Thr Phe
          1               5                  10 ctg gac acc atc gct acg cgc ttc gac ggc acg cac agt aac ttc gtg      338
Leu Asp Thr Ile Ala Thr Arg Phe Asp Gly Thr His Ser Asn Phe Val
 15                  20                  25                  30 ctg ggc aac gcc agt ggc ggg gct ctt ccc gtg gtc tac tgc tct gat      386
Leu Gly Asn Ala Ser Gly Gly Ala Leu Pro Val Val Tyr Cys Ser Asp
                 35                  40                  45 ggc ttc tgt gac ctc acg ggc ttc tcc cgg gct gag gtc atg cag cgg      434
Gly Phe Cys Asp Leu Thr Gly Phe Ser Arg Ala Glu Val Met Gln Arg
         50                  55                  60 ggc tgt gcc tgc tcc ttc ctt tat ggg cca gac acc agt gag ctc gtc     482
Gly Cys Ala Cys Ser Phe Leu Tyr Gly Pro Asp Thr Ser Glu Leu Val
         65                  70                  75 cgc caa cag atc cgc aag gcc ctg gac gag cac aag gag ttc aag gct     530
```

```
                 Arg Gln Gln Ile Arg Lys Ala Leu Asp Glu H is Lys Glu Phe Lys Ala
                      80                  85                  90 gag ctg atc ctg tac cgg aag agc ggg ctc c cg ttc tgg tgt ctc ctg        578
Glu Leu Ile Leu Tyr Arg Lys Ser Gly Leu P ro Phe Trp Cys Leu Leu
 95                 100                 105                 110 gat gtg ata ccc ata aag aat gag aaa ggg g ag gtg gct ctc ttc cta        626
Asp Val Ile Pro Ile Lys Asn Glu Lys Gly G lu Val Ala Leu Phe Leu
                    115                 120                 125 gtc tct cac aag gac atc agc gaa acc aag a ac cga ggg ggc ccc gac        674
Val Ser His Lys Asp Ile Ser Glu Thr Lys A sn Arg Gly Gly Pro Asp
                130                 135                 140 aga tgg aaa gag aca ggt ggt ggc cgg cgc c ga tat ggc cgg gca cga        722
Arg Trp Lys Glu Thr Gly Gly Gly Arg Arg A rg Tyr Gly Arg Ala Arg
            145                 150                 155 tcc aaa ggc ttc aat gcc aac cgg cgg cgg a gc cgg gcc gtg ctc tac        770
Ser Lys Gly Phe Asn Ala Asn Arg Arg Arg S er Arg Ala Val Leu Tyr
        160                 165                 170 cac ctg tcc ggg cac ctg cag aag cag ccc a ag ggc aag cac aag ctc        818
His Leu Ser Gly His Leu Gln Lys Gln Pro L ys Gly Lys His Lys Leu
175                 180                 185                 190 aat aag ggg gtg ttt ggg gag aaa cca aac t tg cct gag tac aaa gta        866
Asn Lys Gly Val Phe Gly Glu Lys Pro Asn L eu Pro Glu Tyr Lys Val
                    195                 200                 205 gcc gcc atc cgg aag tcg ccc ttc atc ctg t tg cac tgt ggg gca ctg        914
Ala Ala Ile Arg Lys Ser Pro Phe Ile Leu L eu His Cys Gly Ala Leu
                210                 215                 220 aga gcc acc tgg gat ggc ttc atc ctg ctc g cc aca ctc tat gtg gct        962
Arg Ala Thr Trp Asp Gly Phe Ile Leu Leu A la Thr Leu Tyr Val Ala
            225                 230                 235 gtc act gtg ccc tac agc gtg tgt gtg agc a ca gca cgg gag ccc agt       1010
Val Thr Val Pro Tyr Ser Val Cys Val Ser T hr Ala Arg Glu Pro Ser
        240                 245                 250 gcc gcc cgc ggc ccg ccc agc gtc tgt gac c tg gcc gtg gag gtc ctc       1058
Ala Ala Arg Gly Pro Pro Ser Val Cys Asp L eu Ala Val Glu Val Leu
255                 260                 265                 270 ttc atc ctt gac att gtg ctg aat ttc cgt a cc aca ttc gtg tcc aag       1106
Phe Ile Leu Asp Ile Val Leu Asn Phe Arg T hr Thr Phe Val Ser Lys
                    275                 280                 285 tcg ggc cag gtg gtg ttt gcc cca aag tcc a tt tgc ctc cac tac gtc       1154
Ser Gly Gln Val Val Phe Ala Pro Lys Ser I le Cys Leu His Tyr Val
                290                 295                 300 acc acc tgg ttc ctg ctg gat gtc atc gca g cg ctg ccc ttt gac ctg       1202
Thr Thr Trp Phe Leu Leu Asp Val Ile Ala A la Leu Pro Phe Asp Leu
            305                 310                 315 cta cat gcc ttc aag gtc aac gtg tac ttc g gg gcc cat ctg ctg aag       1250
Leu His Ala Phe Lys Val Asn Val Tyr Phe G ly Ala His Leu Leu Lys
        320                 325                 330 acg gtg cgc ctg ctg cgc ctg ctg cgc ctg c tt ccg cgg ctg gac cgg       1298
Thr Val Arg Leu Leu Arg Leu Leu Arg Leu L eu Pro Arg Leu Asp Arg
335                 340                 345                 350 tac tcg cag tac agc gcc gtg gtg ctg aca c tg ctc atg gcc gtg ttc       1346
Tyr Ser Gln Tyr Ser Ala Val Val Leu Thr L eu Leu Met Ala Val Phe
                    355                 360                 365 gcc ctg ctc gcg cac tgg gtc gcc tgc gtc t gg ttt tac att ggc cag       1394
Ala Leu Leu Ala His Trp Val Ala Cys Val T rp Phe Tyr Ile Gly Gln
                370                 375                 380 cgg gag atc gag agc agc gaa tcc gag ctg c ct gag att ggc tgg ctg       1442
Arg Glu Ile Glu Ser Ser Glu Ser Glu Leu P ro Glu Ile Gly Trp Leu
            385                 390                 395
```

```
cag gag ctg gcc cgc cga ctg gag act ccc t ac tac ctg gtg ggc cgg      1490
Gln Glu Leu Ala Arg Arg Leu Glu Thr Pro T yr Tyr Leu Val Gly Arg
        400                 405                 410 agg cca gct gga ggg aac agc tcc ggc cag a gt gac aac tgc agc agc      1538
Arg Pro Ala Gly Gly Asn Ser Ser Gly Gln S er Asp Asn Cys Ser Ser
415                 420                 425                 430 agc agc gag gcc aac ggg acg ggg ctg gag c tg ctg ggc ggc ccg tcg      1586
Ser Ser Glu Ala Asn Gly Thr Gly Leu Glu L eu Leu Gly Gly Pro Ser
                435                 440                 445 ctg cgc agc gcc tac atc acc tcc ctc tac t tc gca ctc agc agc ctc      1634
Leu Arg Ser Ala Tyr Ile Thr Ser Leu Tyr P he Ala Leu Ser Ser Leu
        450                 455                 460 acc agc gtg ggc ttc ggc aac gtg tcc gcc a ac acg gac acc gag aag      1682
Thr Ser Val Gly Phe Gly Asn Val Ser Ala A sn Thr Asp Thr Glu Lys
                465                 470                 475 atc ttc tcc atc tgc acc atg ctc atc ggc g cc ctg atg cac gcg gtg      1730
Ile Phe Ser Ile Cys Thr Met Leu Ile Gly A la Leu Met His Ala Val
        480                 485                 490 gtg ttt ggg aac gtg acg gcc atc atc cag c gc atg tac gcc cgc cgc      1778
Val Phe Gly Asn Val Thr Ala Ile Ile Gln A rg Met Tyr Ala Arg Arg
495                 500                 505                 510 ttt ctg tac cac agc cgc acg cgc gac cag c gc gac tac atc cgc atc      1826
Phe Leu Tyr His Ser Arg Thr Arg Asp Gln A rg Asp Tyr Ile Arg Ile
                515                 520                 525 cac cgt atc ccc aag ccc ctc aag cag cgc a tg ctg gag tac ttc cag      1874
His Arg Ile Pro Lys Pro Leu Lys Gln Arg M et Leu Glu Tyr Phe Gln
        530                 535                 540 gcc acc tgg gcg gtg aac aat ggc atc gac a cc acc gag ctg ctg cag      1922
Ala Thr Trp Ala Val Asn Asn Gly Ile Asp T hr Thr Glu Leu Leu Gln
                545                 550                 555 agc ctc cct gac gag ctg cgc gca gac atc g cc atg cac ctg cac aag      1970
Ser Leu Pro Asp Glu Leu Arg Ala Asp Ile A la Met His Leu His Lys
        560                 565                 570 gag gtc ctg cag ctg cca ctg ttt gag gcg g cc agc cgc ggc tgc ctg      2018
Glu Val Leu Gln Leu Pro Leu Phe Glu Ala A la Ser Arg Gly Cys Leu
575                 580                 585                 590 cgg gca ctg tct ctg gcc ctg cgg ccc gcc t tc tgc acg ccg ggc gag      2066
Arg Ala Leu Ser Leu Ala Leu Arg Pro Ala P he Cys Thr Pro Gly Glu
                595                 600                 605 tac ctc atc cac caa ggc gat gcc ctg cag g cc ctc tac ttt gtc tgc      2114
Tyr Leu Ile His Gln Gly Asp Ala Leu Gln A la Leu Tyr Phe Val Cys
        610                 615                 620 tct ggc tcc atg gag gtg ctc aag ggt ggc a cc gtg ctc gcc atc cta      2162
Ser Gly Ser Met Glu Val Leu Lys Gly Gly T hr Val Leu Ala Ile Leu
                625                 630                 635 ggg aag ggc gac ctg atc ggc tgt gag ctg c cc cgg cgg gag cag gtg      2210
Gly Lys Gly Asp Leu Ile Gly Cys Glu Leu P ro Arg Arg Glu Gln Val
        640                 645                 650 gta aag gcc aat gcc gac gtg aag ggg ctg a cg tac tgc gtc ctg cag      2258
Val Lys Ala Asn Ala Asp Val Lys Gly Leu T hr Tyr Cys Val Leu Gln
655                 660                 665                 670 tgt ctg cag ctg gct ggc ctg cac gac agc c tt gcg ctg tac ccc gag      2306
Cys Leu Gln Leu Ala Gly Leu His Asp Ser L eu Ala Leu Tyr Pro Glu
                675                 680                 685 ttt gcc ccg cgc ttc agt cgt ggc ctc cga g gg gag ctc agc tac aac      2354
Phe Ala Pro Arg Phe Ser Arg Gly Leu Arg G ly Glu Leu Ser Tyr Asn
        690                 695                 700 ctg ggt gct ggg gga ggc tct gca gag gtg g ac acc agc tcc ctg agc      2402
Leu Gly Ala Gly Gly Gly Ser Ala Glu Val A sp Thr Ser Ser Leu Ser
                705                 710                 715
```

```
ggc gac aat acc ctt atg tcc acg ctg gag g ag aag gag aca gat ggg    2450
Gly Asp Asn Thr Leu Met Ser Thr Leu Glu G lu Lys Glu Thr Asp Gly
        720                 725                 730 gag cag ggc ccc acg gtc tcc cca gcc cca g ct gat gag ccc tcc agc    2498
Glu Gln Gly Pro Thr Val Ser Pro Ala Pro A la Asp Glu Pro Ser Ser
735                 740                 745                 750 ccc ctg ctg tcc cct ggc tgc acc tcc tca t cc tca gct gcc aag ctg    2546
Pro Leu Leu Ser Pro Gly Cys Thr Ser Ser S er Ser Ala Ala Lys Leu
                755                 760                 765 cta tcc cca cgt cga aca gca ccc cgg cct c gt cta ggt ggc aga ggg    2594
Leu Ser Pro Arg Arg Thr Ala Pro Arg Pro A rg Leu Gly Gly Arg Gly
            770                 775                 780 agg cca ggc agg gca ggg gct ttg aag gct g ag gct ggc ccc tct gct    2642
Arg Pro Gly Arg Ala Gly Ala Leu Lys Ala G lu Ala Gly Pro Ser Ala
        785                 790                 795 ccc cca cgg gcc cta gag ggg cta cgg ctg c cc ccc atg cca tgg aat    2690
Pro Pro Arg Ala Leu Glu Gly Leu Arg Leu P ro Pro Met Pro Trp Asn
800                 805                 810 gtg ccc cca gat ctg agc ccc agg gta gta g at ggc att gaa gac ggc    2738
Val Pro Pro Asp Leu Ser Pro Arg Val Val A sp Gly Ile Glu Asp Gly
815                 820                 825                 830 tgt ggc tcg gac cag ccc aag ttc tct ttc c gc gtg ggc cag tct ggc    2786
Cys Gly Ser Asp Gln Pro Lys Phe Ser Phe A rg Val Gly Gln Ser Gly
                835                 840                 845 ccg gaa tgt agc agc agc ccc tcc cct gga c ca gag agc ggc ctg ctc    2834
Pro Glu Cys Ser Ser Ser Pro Ser Pro Gly P ro Glu Ser Gly Leu Leu
            850                 855                 860 act gtt ccc cat ggg ccc agc gag gca agg a ac aca gac aca ctg gac    2882
Thr Val Pro His Gly Pro Ser Glu Ala Arg A sn Thr Asp Thr Leu Asp
        865                 870                 875 aag ctt cgg cag gcg gtg aca gag ctg tca g ag cag gtg ctg cag atg    2930
Lys Leu Arg Gln Ala Val Thr Glu Leu Ser G lu Gln Val Leu Gln Met
880                 885                 890 cgg gaa gga ctg cag tca ctt cgc cag gct g tg cag ctt gtc ctg gcg    2978
Arg Glu Gly Leu Gln Ser Leu Arg Gln Ala V al Gln Leu Val Leu Ala
895                 900                 905                 910 ccc cac agg gag ggt ccg tgc cct cgg gca t cg gga gag ggg ccg tgc    3026
Pro His Arg Glu Gly Pro Cys Pro Arg Ala S er Gly Glu Gly Pro Cys
                915                 920                 925 cca gcc agc acc tcc ggg ctt ctg cag cct c tg tgt gtg gac act ggg    3074
Pro Ala Ser Thr Ser Gly Leu Leu Gln Pro L eu Cys Val Asp Thr Gly
            930                 935                 940 gca tcc tcc tac tgc ctg cag ccc cca gct g gc tct gtc ttg agt ggg    3122
Ala Ser Ser Tyr Cys Leu Gln Pro Pro Ala G ly Ser Val Leu Ser Gly
        945                 950                 955 act tgg ccc cac cct cgt ccg ggg cct cct c cc ctc atg gca ccc cgg    3170
Thr Trp Pro His Pro Arg Pro Gly Pro Pro P ro Leu Met Ala Pro Arg
960                 965                 970 ccc tgg ggt ccc cca gcg tct cag agc tcc c cc tgg cct cga gcc aca    3218
Pro Trp Gly Pro Pro Ala Ser Gln Ser Ser P ro Trp Pro Arg Ala Thr
975                 980                 985                 990 gct ttc tgg acc tcc acc tca gac tca gag c cc cct gcc tca gga gac    3266
Ala Phe Trp Thr Ser Thr Ser Asp Ser Glu P ro Pro Ala Ser Gly Asp
                995                 1000                1005 ctc tgc tct gag ccc agc acc cct gcc tcc c ct cct cct tct gag gaa    3314
Leu Cys Ser Glu Pro Ser Thr Pro Ala Ser P ro Pro Pro Ser Glu Glu
            1010                1015                1020 ggg gct agg act ggg ccc gca gag cct gtg a gc cag gct gag gct acc    3362
Gly Ala Arg Thr Gly Pro Ala Glu Pro Val S er Gln Ala Glu Ala Thr
```

-continued

```
              1025                1030               1035
agc act gga gag ccc cca cca ggg tca ggg g gc ctg gcc ttg ccc tgg        3410
Ser Thr Gly Glu Pro Pro Pro Gly Ser Gly G ly Leu Ala Leu Pro Trp
            1040                1045              1050 gac ccc cac agc ctg gag atg gtg ctt att g gc tgc cat ggc tct ggc        3458
Asp Pro His Ser Leu Glu Met Val Leu Ile G ly Cys His Gly Ser Gly
1055                106 0                1065                1070 aca gtc cag tgg acc cag gaa gaa ggc aca g gg gtc t gagtaccagc           3505
Thr Val Gln Trp Thr Gln Glu Glu Gly Thr G ly Val
                1075                1080 cctagaactc agcgttgcca ggtgtgctgc catctgctgt tcggcccaac c tcagagtga      3565 aggcagggtg gcagcctccc cacggactcc atgcggcccg ctggctcagg g cagggagcc     3625 tggaagcaaa ggaggacctg gctcctgact ctcagagagg ataggctgga t ccctggggc     3685 aggcctctcc tcggcctgct cctctgacct cccggtctcc ctctgcaggc t ggggcaga     3745 ggcctgagga caaggaagag ctttgccatc ccctgcatgt gcccctgcct c tacctgtcc    3805 ccaaattttt atattaaaaa aaaaaataaa ataaactaaa aaaaaaaaaa a a             3857

<210> SEQ ID NO 20

<211> LENGTH: 1082
<212> TYPE: PRT
<213> ORGANISM: H. sapiens

<400> SEQUENCE: 20

Met Pro Ala Met Arg Gly Leu Leu Ala Pro G ln Asn Thr Phe Leu Asp
 1               5                  10                  15

Thr Ile Ala Thr Arg Phe Asp Gly Thr His S er Asn Phe Val Leu Gly
                20                  25                  30

Asn Ala Ser Gly Gly Ala Leu Pro Val Val T yr Cys Ser Asp Gly Phe
            35                  40                  45

Cys Asp Leu Thr Gly Phe Ser Arg Ala Glu V al Met Gln Arg Gly Cys
        50                  55                  60

Ala Cys Ser Phe Leu Tyr Gly Pro Asp Thr S er Glu Leu Val Arg Gln
65                  70                  75                  80

Gln Ile Arg Lys Ala Leu Asp Glu His Lys G lu Phe Lys Ala Glu Leu
                85                  90                  95

Ile Leu Tyr Arg Lys Ser Gly Leu Pro Phe T rp Cys Leu Leu Asp Val
                100                 105                 110

Ile Pro Ile Lys Asn Glu Lys Gly Glu Val A la Leu Phe Leu Val Ser
            115                 120                 125

His Lys Asp Ile Ser Glu Thr Lys Asn Arg G ly Gly Pro Asp Arg Trp
        130                 135                 140

Lys Glu Thr Gly Gly Gly Arg Arg Arg Tyr G ly Arg Ala Arg Ser Lys
145                 150                 155                 160

Gly Phe Asn Ala Asn Arg Arg Arg Ser Arg A la Val Leu Tyr His Leu
                165                 170                 175

Ser Gly His Leu Gln Lys Gln Pro Lys Gly L ys His Lys Leu Asn Lys
            180                 185                 190

Gly Val Phe Gly Glu Lys Pro Asn Leu Pro G lu Tyr Lys Val Ala Ala
        195                 200                 205

Ile Arg Lys Ser Pro Phe Ile Leu Leu His C ys Gly Ala Leu Arg Ala
    210                 215                 220

Thr Trp Asp Gly Phe Ile Leu Leu Ala Thr L eu Tyr Val Ala Val Thr
```

```
                225                 230                 235                 240
Val Pro Tyr Ser Val Cys Val Ser Thr Ala Arg Glu Pro Ser Ala Ala
                    245                 250                 255
Arg Gly Pro Pro Ser Val Cys Asp Leu Ala Val Glu Val Leu Phe Ile
                260                 265                 270
Leu Asp Ile Val Leu Asn Phe Arg Thr Thr Phe Val Ser Lys Ser Gly
            275                 280                 285
Gln Val Val Phe Ala Pro Lys Ser Ile Cys Leu His Tyr Val Thr Thr
        290                 295                 300
Trp Phe Leu Leu Asp Val Ile Ala Ala Leu Pro Phe Asp Leu Leu His
305                 310                 315                 320
Ala Phe Lys Val Asn Val Tyr Phe Gly Ala His Leu Leu Lys Thr Val
                325                 330                 335
Arg Leu Leu Arg Leu Leu Arg Leu Leu Pro Arg Leu Asp Arg Tyr Ser
                340                 345                 350
Gln Tyr Ser Ala Val Val Leu Thr Leu Leu Met Ala Val Phe Ala Leu
        355                 360                 365
Leu Ala His Trp Val Ala Cys Val Trp Phe Tyr Ile Gly Gln Arg Glu
    370                 375                 380
Ile Glu Ser Ser Glu Ser Glu Leu Pro Glu Ile Gly Trp Leu Gln Glu
385                 390                 395                 400
Leu Ala Arg Arg Leu Glu Thr Pro Tyr Tyr Leu Val Gly Arg Arg Pro
                405                 410                 415
Ala Gly Gly Asn Ser Ser Gly Gln Ser Asp Asn Cys Ser Ser Ser Ser
                420                 425                 430
Glu Ala Asn Gly Thr Gly Leu Glu Leu Leu Gly Gly Pro Ser Leu Arg
            435                 440                 445
Ser Ala Tyr Ile Thr Ser Leu Tyr Phe Ala Leu Ser Ser Leu Thr Ser
        450                 455                 460
Val Gly Phe Gly Asn Val Ser Ala Asn Thr Asp Thr Glu Lys Ile Phe
465                 470                 475                 480
Ser Ile Cys Thr Met Leu Ile Gly Ala Leu Met His Ala Val Val Phe
                485                 490                 495
Gly Asn Val Thr Ala Ile Ile Gln Arg Met Tyr Ala Arg Arg Phe Leu
                500                 505                 510
Tyr His Ser Arg Thr Arg Asp Gln Arg Asp Tyr Ile Arg Ile His Arg
            515                 520                 525
Ile Pro Lys Pro Leu Lys Gln Arg Met Leu Glu Tyr Phe Gln Ala Thr
        530                 535                 540
Trp Ala Val Asn Asn Gly Ile Asp Thr Thr Glu Leu Leu Gln Ser Leu
545                 550                 555                 560
Pro Asp Glu Leu Arg Ala Asp Ile Ala Met His Leu His Lys Glu Val
                565                 570                 575
Leu Gln Leu Pro Leu Phe Glu Ala Ala Ser Arg Gly Cys Leu Arg Ala
                580                 585                 590
Leu Ser Leu Ala Leu Arg Pro Ala Phe Cys Thr Pro Gly Glu Tyr Leu
            595                 600                 605
Ile His Gln Gly Asp Ala Leu Gln Ala Leu Tyr Phe Val Cys Ser Gly
        610                 615                 620
Ser Met Glu Val Leu Lys Gly Gly Thr Val Leu Ala Ile Leu Gly Lys
625                 630                 635                 640
Gly Asp Leu Ile Gly Cys Glu Leu Pro Arg Arg Glu Gln Val Val Lys
                645                 650                 655
```

-continued

```
Ala Asn Ala Asp Val Lys Gly Leu Thr Tyr Cys Val Leu Gln Cys Leu
            660                 665                 670

Gln Leu Ala Gly Leu His Asp Ser Leu Ala Leu Tyr Pro Glu Phe Ala
        675                 680                 685

Pro Arg Phe Ser Arg Gly Leu Arg Gly Glu Leu Ser Tyr Asn Leu Gly
    690                 695                 700

Ala Gly Gly Gly Ser Ala Glu Val Asp Thr Ser Ser Leu Ser Gly Asp
705                 710                 715                 720

Asn Thr Leu Met Ser Thr Leu Glu Glu Lys Glu Thr Asp Gly Glu Gln
                725                 730                 735

Gly Pro Thr Val Ser Pro Ala Pro Ala Asp Glu Pro Ser Ser Pro Leu
            740                 745                 750

Leu Ser Pro Gly Cys Thr Ser Ser Ser Ala Ala Lys Leu Leu Ser
        755                 760                 765

Pro Arg Arg Thr Ala Pro Arg Pro Arg Leu Gly Gly Arg Gly Arg Pro
    770                 775                 780

Gly Arg Ala Gly Ala Leu Lys Ala Glu Ala Gly Pro Ser Ala Pro Pro
785                 790                 795                 800

Arg Ala Leu Glu Gly Leu Arg Leu Pro Pro Met Pro Trp Asn Val Pro
                805                 810                 815

Pro Asp Leu Ser Pro Arg Val Val Asp Gly Ile Glu Asp Gly Cys Gly
            820                 825                 830

Ser Asp Gln Pro Lys Phe Ser Phe Arg Val Gly Ser Gly Pro Glu
        835                 840                 845

Cys Ser Ser Ser Pro Ser Pro Gly Pro Glu Ser Gly Leu Leu Thr Val
850                 855                 860

Pro His Gly Pro Ser Glu Ala Arg Asn Thr Asp Thr Leu Asp Lys Leu
865                 870                 875                 880

Arg Gln Ala Val Thr Glu Leu Ser Glu Gln Val Leu Gln Met Arg Glu
                885                 890                 895

Gly Leu Gln Ser Leu Arg Gln Ala Val Gln Leu Val Leu Ala Pro His
            900                 905                 910

Arg Glu Gly Pro Cys Pro Arg Ala Ser Gly Glu Gly Pro Cys Pro Ala
        915                 920                 925

Ser Thr Ser Gly Leu Leu Gln Pro Leu Cys Val Asp Thr Gly Ala Ser
930                 935                 940

Ser Tyr Cys Leu Gln Pro Pro Ala Gly Ser Val Leu Ser Gly Thr Trp
945                 950                 955                 960

Pro His Pro Arg Pro Gly Pro Pro Leu Met Ala Pro Arg Pro Trp
                965                 970                 975

Gly Pro Pro Ala Ser Gln Ser Ser Pro Trp Pro Arg Ala Thr Ala Phe
            980                 985                 990

Trp Thr Ser Thr Ser Asp Ser Glu Pro Pro Ala Ser Gly Asp Leu Cys
        995                 1000                1005

Ser Glu Pro Ser Thr Pro Ala Ser Pro Pro Ser Glu Glu Gly Ala
1010                1015                1020

Arg Thr Gly Pro Ala Glu Pro Val Ser Gln Ala Glu Ala Thr Ser Thr
1025                1030                1035                1040

Gly Glu Pro Pro Pro Gly Ser Gly Leu Ala Leu Pro Trp Asp Pro
                1045                1050                1055

His Ser Leu Glu Met Val Leu Ile Gly Cys His Gly Ser Gly Thr Val
            1060                1065                1070
```

```
Gln Trp Thr Gln Glu Glu Gly Thr Gly Val
        1075                1080

<210> SEQ ID NO 21
<211> LENGTH: 1800
<212> TYPE: DNA
<213> ORGANISM: H. sapiens
<220> FEATURE:
<221> NAME/KEY: CDS
<222> LOCATION: (346)...(1057)
<223> OTHER INFORMATION: K+Hnov28, splice 1

<400> SEQUENCE: 21
atttgaatga ctgggttact tcctagactc ttcctccttc tcttaagtac a gtatagttc      60 tttctctgaa aatcttcagt ctcttagttc cagatgggtt ctctatggta g gaatacagg    120 acatgtagaa ggccctaggg gaatgctttc ttccccagat ctttgccctg t agtaggttt   180 cagctgagca aggacgagta gttttttctgg tgtttggcct cctctgttgg g tggaaaaag  240 actttcttct ctattttcct agttatatat gctatcatat gtctgttttt c tcctcttga   300 agtttccctg aaacctgggc tcttgaagac gcatcactgg agcag atg gat aat gga    357
                                                    Met Asp Asn Gly
                                                     1
```

| | | | | | | | | | | | | | | | |
|---|---|---|---|---|---|---|---|---|---|---|---|---|---|---|---|
| gac | tgg | ggc | tat | atg | atg | act | gac | cca | gtc | a ca | tta | aat | gta | ggt | gga | 405 |
| Asp | Trp | Gly | Tyr | Met | Met | Thr | Asp | Pro | Val | T hr | Leu | Asn | Val | Gly | Gly | |
| 5 | | | | 10 | | | | | 15 | | | | | 20 | | |

```
cac ttg tat aca acg tct ctc acc aca ttg a cg cgt tac ccg gat tcc     453
His Leu Tyr Thr Thr Ser Leu Thr Thr Leu T hr Arg Tyr Pro Asp Ser
            25                      30                      35 atg ctt gga gct atg ttt ggg ggg gac ttc c cc aca gct cga gac cct    501
Met Leu Gly Ala Met Phe Gly Gly Asp Phe P ro Thr Ala Arg Asp Pro
            40                      45                      50 caa ggc aat tac ttt att gat cga gat gga c ct ctt ttc cga tat gtc    549
Gln Gly Asn Tyr Phe Ile Asp Arg Asp Gly P ro Leu Phe Arg Tyr Val
            55                      60                      65 ctc aac ttc tta aga act tca gaa ttg acc t ta ccg ttg gat ttt aag    597
Leu Asn Phe Leu Arg Thr Ser Glu Leu Thr L eu Pro Leu Asp Phe Lys
        70                      75                      80 gaa ttt gat ctg ctt cgg aaa gaa gca gat t tt tac cag att gag ccc    645
Glu Phe Asp Leu Leu Arg Lys Glu Ala Asp P he Tyr Gln Ile Glu Pro
85                      90                      95                     100 ttg att cag tgt ctc aat gat cct aag cct t tg tat ccc atg gat act    693
Leu Ile Gln Cys Leu Asn Asp Pro Lys Pro L eu Tyr Pro Met Asp Thr
                    105                     110                     115 ttt gaa gaa gtt gtg gag ctg tct agt act c gg aag ctt tct aag tac    741
Phe Glu Glu Val Val Glu Leu Ser Ser Thr A rg Lys Leu Ser Lys Tyr
                    120                     125                     130 tcc aac cca gtg gct gtc atc ata acg caa c ta acc atc acc act aag    789
Ser Asn Pro Val Ala Val Ile Ile Thr Gln L eu Thr Ile Thr Thr Lys
                    135                     140                     145 gtc cat tcc tta cta gaa ggc atc tca aat t at ttt acc aag tgg aat    837
Val His Ser Leu Leu Glu Gly Ile Ser Asn T yr Phe Thr Lys Trp Asn
            150                     155                     160 aag cac atg atg gac acc aga gac tgc cag g tt tcc ttt act ttt gga    885
Lys His Met Met Asp Thr Arg Asp Cys Gln V al Ser Phe Thr Phe Gly
165                     170                     175                     180 ccc tgt gat tat cac cag gaa gtt tct ctt a gg gtc cac ctg atg gaa    933
Pro Cys Asp Tyr His Gln Glu Val Ser Leu A rg Val His Leu Met Glu
                    185                     190                     195 tac att aca aaa caa ggt ttc acg atc cgc a ac acc cgg gtg cat cac    981
Tyr Ile Thr Lys Gln Gly Phe Thr Ile Arg A sn Thr Arg Val His His
```

-continued

|  |  |  |  |
|---|---|---|---|
| | 200 | 205 | 210 |
| atg agt gag cgg gcc aat gaa aac aca gtg g ag cac aac tgg act ttc<br>Met Ser Glu Arg Ala Asn Glu Asn Thr Val G lu His Asn Trp Thr Phe<br>215 220 225 | | | 1029 |
| tgt agg cta gcc cgg aag aca gac gac t gat ctccgac cctgccacag<br>Cys Arg Leu Ala Arg Lys Thr Asp Asp<br>230 235 | | | 1077 |
| gttcctggaa agactctcca ggaaatggaa gatactgatt ttttttttta atcacagtg | | | 1137 |
| tgagatattt ttttctttt aaatagttgt atttatttga aggcagtgag g accagaagg | | | 1197 |
| aagttttgtg ctttggcaga ctcctccatg ttttgttccc ttcccctga g tatgcatgt | | | 1257 |
| gcctgttcag agtctccaga tacctttttt ataaaaagaa gtctgaaaat c attatggta | | | 1317 |
| tataatctac ccttaacaga gcttttctta ttacagtgct aaaatgattt c tgataaaat | | | 1377 |
| ggtccctaac tcaactagaa ggctaaaaat acaagaatga aagaataagc a gagtactca | | | 1437 |
| tgatgccttt gagaaaaatc aaaacatcat gtagggtgac ctagtttcca a accaataaa | | | 1497 |
| taagtagtat tgtaatatta aaggaaaact gttccaatca tttaaaagta c ttattaagt | | | 1557 |
| actgcttttt acagttatga caactgtttc tttctatgca tataaatcaa g gaaccaaat | | | 1617 |
| atctgtagcc atggaaatgt ctgactagaa atatttatat tgaattctga a tacaaaatg | | | 1677 |
| tccctgtggt agaaaactta ctctttatgc ctggtgcagt ataattccca a gtgtactgt | | | 1737 |
| ctaccagaaa aaaaaaacaa aactaataaa aaatgaaata tgaaaaaaaa a aaaaaaaa | | | 1797 |
| aaa | | | 1800 |

<210> SEQ ID NO 22
<211> LENGTH: 1836
<212> TYPE: DNA
<213> ORGANISM: H. sapiens
<220> FEATURE:
<221> NAME/KEY: CDS
<222> LOCATION: (382)...(1093)
<223> OTHER INFORMATION: K+Hnov28 splice 2

<400> SEQUENCE: 22

|  |  |
|---|---|
| gaggaatgtt atgattttgt gactatttgt gacagctttt taatattagg t cacttttaa | 60 |
| acctatagct tctctcttct agaccacatg gttgggaaag gagaaagaga a aatgattac | 120 |
| ttgtagagaa aaatccattt ctgcagtggt atggttaagg ataatctaac c ataatcaca | 180 |
| ttatccttgt atgcctggct acttgtgctg gcctgtatgt gaatgttaac c ccaaagact | 240 |
| cctttagatg tcgctgaact agttactata aaaagtattt cgctttcaaa c tcccacatt | 300 |
| tcaagaagag caaaactcaa tacaaggcaa ttttgaagtt tccctgaaac c tgggctctt | 360 |
| gaagacgcat cactggagca g atg gat aat gga gac tgg ggc tat atg atg<br>Met Asp Asn Gly Asp Trp Gly Tyr Met Met<br>1 5 10 | 411 |
| act gac cca gtc aca tta aat gta ggt gga c ac ttg tat aca acg tct<br>Thr Asp Pro Val Thr Leu Asn Val Gly Gly H is Leu Tyr Thr Thr Ser<br>15 20 25 | 459 |
| ctc acc aca ttg acg cgt tac ccg gat tcc a tg ctt gga gct atg ttt<br>Leu Thr Thr Leu Thr Arg Tyr Pro Asp Ser M et Leu Gly Ala Met Phe<br>30 35 40 | 507 |
| ggg ggg gac ttc ccc aca gct cga gac cct c aa ggc aat tac ttt att<br>Gly Gly Asp Phe Pro Thr Ala Arg Asp Pro G ln Gly Asn Tyr Phe Ile<br>45 50 55 | 555 |
| gat cga gat gga cct ctt ttc cga tat gtc c tc aac ttc tta aga act<br>Asp Arg Asp Gly Pro Leu Phe Arg Tyr Val L eu Asn Phe Leu Arg Thr<br>60 65 70 | 603 |

| | | | | | | | | | | | | | | | |
|---|---|---|---|---|---|---|---|---|---|---|---|---|---|---|---|
| tca | gaa | ttg | acc | tta | ccg | ttg | gat | ttt | aag | g aa | ttt | gat | ctg | ctt | cgg | 651 |
| Ser | Glu | Leu | Thr | Leu | Pro | Leu | Asp | Phe | Lys | G lu | Phe | Asp | Leu | Leu | Arg |
| 75 | | | | 80 | | | | | 85 | | | | | 90 |

```
tca gaa ttg acc tta ccg ttg gat ttt aag g aa ttt gat ctg ctt cgg      651
Ser Glu Leu Thr Leu Pro Leu Asp Phe Lys G lu Phe Asp Leu Leu Arg
 75              80                  85                  90 aaa gaa gca gat ttt tac cag att gag ccc t tg att cag tgt ctc aat      699
Lys Glu Ala Asp Phe Tyr Gln Ile Glu Pro L eu Ile Gln Cys Leu Asn
                95                 100                 105 gat cct aag cct ttg tat ccc atg gat act t tt gaa gaa gtt gtg gag      747
Asp Pro Lys Pro Leu Tyr Pro Met Asp Thr P he Glu Glu Val Val Glu
            110                 115                 120 ctg tct agt act cgg aag ctt tct aag tac t cc aac cca gtg gct gtc      795
Leu Ser Ser Thr Arg Lys Leu Ser Lys Tyr S er Asn Pro Val Ala Val
        125                 130                 135 atc ata acg caa cta acc atc acc act aag g tc cat tcc tta cta gaa      843
Ile Ile Thr Gln Leu Thr Ile Thr Thr Lys V al His Ser Leu Leu Glu
    140                 145                 150 ggc atc tca aat tat ttt acc aag tgg aat a ag cac atg atg gac acc      891
Gly Ile Ser Asn Tyr Phe Thr Lys Trp Asn L ys His Met Met Asp Thr
155                 160                 165                 170 aga gac tgc cag gtt tcc ttt act ttt gga c cc tgt gat tat cac cag      939
Arg Asp Cys Gln Val Ser Phe Thr Phe Gly P ro Cys Asp Tyr His Gln
                175                 180                 185 gaa gtt tct ctt agg gtc cac ctg atg gaa t ac att aca aaa caa ggt      987
Glu Val Ser Leu Arg Val His Leu Met Glu T yr Ile Thr Lys Gln Gly
            190                 195                 200 ttc acg atc cgc aac acc cgg gtg cat cac a tg agt gag cgg gcc aat     1035
Phe Thr Ile Arg Asn Thr Arg Val His His M et Ser Glu Arg Ala Asn
        205                 210                 215 gaa aac aca gtg gag cac aac tgg act ttc t gt agg cta gcc cgg aag     1083
Glu Asn Thr Val Glu His Asn Trp Thr Phe C ys Arg Leu Ala Arg Lys
    220                 225                 230 aca gac gac t gatctccgac cctgccacag gttcctggaa aga ctctcca           1133
Thr Asp Asp
235 ggaaatggaa gatactgatt ttttttttta aatcacagtg tgagatattt t ttttctttt   1193 aaatagttgt atttatttga aggcagtgag gaccagaagg aagttttgtg c tttggcaga   1253 ctcctccatg ttttgttccc ttcccccctga gtatgcatgt gcctgttcag a gtctccaga  1313 tacctttttt ataaaaagaa gtctgaaaat cattatggta tataatctac c cttaacaga   1373 gcttttctta ttacagtgct aaaatgattt ctgataaaat ggtccctaac t caactagaa   1433 ggctaaaaat acaagaatga aagaataagc agagtactca tgatgccttt g agaaaaatc   1493 aaaacatcat gtagggtgac ctagtttcca aaccaataaa taagtagtat t gtaatatta   1553 aaggaaaact gttccaatca tttaaaagta cttattaagt actgcttttt a cagttatga   1613 caactgtttc tttctatgca tataaatcaa ggaaccaaat atctgtagcc a tggaaatgt   1673 ctgactagaa atatttatat tgaattctga atacaaaatg tccctgtggt a gaaaactta  1733 ctctttatgc ctggtgcagt ataattccca agtgtactgt ctaccagaaa a aaaaaacaa  1793 aactaataaa aaatgaaata tgaaaaaaaa aaaaaaaaa aaa                       1836
```

<210> SEQ ID NO 23
<211> LENGTH: 1751
<212> TYPE: DNA
<213> ORGANISM: H. sapiens
<220> FEATURE:
<221> NAME/KEY: CDS
<222> LOCATION: (297)...(1008)
<223> OTHER INFORMATION: K+Hnov28 splice 3

```
<400> SEQUENCE: 23
ccatgtttct taccatgtct tgccagagct ttagaaattt gctctgcagt t tgctttaca      60 ggttgatttg ggattgaagt gtgtgagagg gaactgactc aggcagttca g tagctggga    120 aactgtttgt ttaaatgctt ttgaattgta gataaaaata aattcacatt g gcatcatta    180 gtatctgagc atttctcagt gtcttaaggc tggctctcca tgagtgctgg c tgattgact    240 ctcatctata tcgtttccct gaaacctggg ctcttgaaga cgcatcactg g agcag atg    299
                                                                 Met
                                                                  1 gat aat gga gac tgg ggc tat atg atg act g ac cca gtc aca tta aat    347
Asp Asn Gly Asp Trp Gly Tyr Met Met Thr A sp Pro Val Thr Leu Asn
            5                  10                 15 gta ggt gga cac ttg tat aca acg tct ctc a cc aca ttg acg cgt tac    395
Val Gly Gly His Leu Tyr Thr Thr Ser Leu T hr Thr Leu Thr Arg Tyr
         20                  25                  30 ccg gat tcc atg ctt gga gct atg ttt ggg g gg gac ttc ccc aca gct    443
Pro Asp Ser Met Leu Gly Ala Met Phe Gly G ly Asp Phe Pro Thr Ala
     35                  40                  45 cga gac cct caa ggc aat tac ttt att gat c ga gat gga cct ctt ttc    491
Arg Asp Pro Gln Gly Asn Tyr Phe Ile Asp A rg Asp Gly Pro Leu Phe
 50                  55                  60                  65 cga tat gtc ctc aac ttc tta aga act tca g aa ttg acc tta ccg ttg    539
Arg Tyr Val Leu Asn Phe Leu Arg Thr Ser G lu Leu Thr Leu Pro Leu
                 70                  75                  80 gat ttt aag gaa ttt gat ctg ctt cgg aaa g aa gca gat ttt tac cag    587
Asp Phe Lys Glu Phe Asp Leu Leu Arg Lys G lu Ala Asp Phe Tyr Gln
             85                  90                  95 att gag ccc ttg att cag tgt ctc aat gat c ct aag cct ttg tat ccc    635
Ile Glu Pro Leu Ile Gln Cys Leu Asn Asp P ro Lys Pro Leu Tyr Pro
        100                 105                 110 atg gat act ttt gaa gaa gtt gtg gag ctg t ct agt act cgg aag ctt    683
Met Asp Thr Phe Glu Glu Val Val Glu Leu S er Ser Thr Arg Lys Leu
    115                 120                 125 tct aag tac tcc aac cca gtg gct gtc atc a ta acg caa cta acc atc    731
Ser Lys Tyr Ser Asn Pro Val Ala Val Ile I le Thr Gln Leu Thr Ile
130                 135                 140                 145 acc act aag gtc cat tcc tta cta gaa ggc a tc tca aat tat ttt acc    779
Thr Thr Lys Val His Ser Leu Leu Glu Gly I le Ser Asn Tyr Phe Thr
                150                 155                 160 aag tgg aat aag cac atg atg gac acc aga g ac tgc cag gtt tcc ttt    827
Lys Trp Asn Lys His Met Met Asp Thr Arg A sp Cys Gln Val Ser Phe
            165                 170                 175 act ttt gga ccc tgt gat tat cac cag gaa g tt tct ctt agg gtc cac    875
Thr Phe Gly Pro Cys Asp Tyr His Gln Glu V al Ser Leu Arg Val His
        180                 185                 190 ctg atg gaa tac att aca aaa caa ggt ttc a cg atc cgc aac acc cgg    923
Leu Met Glu Tyr Ile Thr Lys Gln Gly Phe T hr Ile Arg Asn Thr Arg
    195                 200                 205 gtg cat cac atg agt gag cgg gcc aat gaa a ac aca gtg gag cac aac    971
Val His His Met Ser Glu Arg Ala Asn Glu A sn Thr Val Glu His Asn
210                 215                 220                 225 tgg act ttc tgt agg cta gcc cgg aag aca g ac gac t gatctccgac      1018
Trp Thr Phe Cys Arg Leu Ala Arg Lys Thr A sp Asp
                230                 235 cctgccacag gttcctggaa agactctcca ggaaatggaa gatactgatt t tttttttta  1078 aatcacagtg tgagatattt ttttctttt aaatagttgt atttatttga a ggcagtgag   1138 gaccagaagg aagttttgtg ctttggcaga ctcctccatg ttttgttccc t tcccctga   1198
```

-continued

```
gtatgcatgt gcctgttcag agtctccaga tacctttttt ataaaaagaa g tctgaaaat    1258 cattatggta tataatctac ccttaacaga gcttttctta ttacagtgct a aaatgattt    1318 ctgataaaat ggtccctaac tcaactagaa ggctaaaaat acaagaatga a agaataagc    1378 agagtactca tgatgccttt gagaaaaatc aaaacatcat gtagggtgac c tagtttcca    1438 aaccaataaa taagtagtat tgtaatatta aaggaaaact gttccaatca t ttaaaagta    1498 cttattaagt actgcttttt acagttatga caactgtttc tttctatgca t ataaatcaa    1558 ggaaccaaat atctgtagcc atggaaatgt ctgactagaa atatttatat t gaattctga    1618 atacaaaatg tccctgtggt agaaaactta ctctttatgc ctggtgcagt a taattccca    1678 agtgtactgt ctaccagaaa aaaaaaacaa aactaataaa aaatgaaata t gaaaaaaaa    1738 aaaaaaaaaa aaa                                                        1751

<210> SEQ ID NO 24
<211> LENGTH: 1542
<212> TYPE: DNA
<213> ORGANISM: H. sapiens
<220> FEATURE:
<221> NAME/KEY: CDS
<222> LOCATION: (88)...(799)
<223> OTHER INFORMATION: K+Hnov28, splice 4

<400> SEQUENCE: 24
cgggcatctc ccggcccggc cgcagcagcc gccgccgccg cgcatttccc t gaaacctgg    60 gctcttgaag acgcatcact ggagcag atg gat aat gga gac tgg ggc tat atg    114
                              Met Asp Asn Gl y Asp Trp Gly Tyr Met
                                1               5 atg act gac cca gtc aca tta aat gta ggt g ga cac ttg tat aca acg    162
Met Thr Asp Pro Val Thr Leu Asn Val Gly G ly His Leu Tyr Thr Thr
 10              15                  20                 25 tct ctc acc aca ttg acg cgt tac ccg gat t cc atg ctt gga gct atg    210
Ser Leu Thr Thr Leu Thr Arg Tyr Pro Asp S er Met Leu Gly Ala Met
             30                  35                  40 ttt ggg ggg gac ttc ccc aca gct cga gac c ct caa ggc aat tac ttt    258
Phe Gly Gly Asp Phe Pro Thr Ala Arg Asp P ro Gln Gly Asn Tyr Phe
         45                  50                  55 att gat cga gat gga cct ctt ttc cga tat g tc ctc aac ttc tta aga    306
Ile Asp Arg Asp Gly Pro Leu Phe Arg Tyr V al Leu Asn Phe Leu Arg
     60                  65                  70 act tca gaa ttg acc tta ccg ttg gat ttt a ag gaa ttt gat ctg ctt    354
Thr Ser Glu Leu Thr Leu Pro Leu Asp Phe L ys Glu Phe Asp Leu Leu
 75                  80                  85 cgg aaa gaa gca gat ttt tac cag att gag c cc ttg att cag tgt ctc    402
Arg Lys Glu Ala Asp Phe Tyr Gln Ile Glu P ro Leu Ile Gln Cys Leu
 90                  95                 100                 105 aat gat cct aag cct ttg tat ccc atg gat a ct ttt gaa gaa gtt gtg    450
Asn Asp Pro Lys Pro Leu Tyr Pro Met Asp T hr Phe Glu Glu Val Val
             110                 115                 120 gag ctg tct agt act cgg aag ctt tct aag t ac tcc aac cca gtg gct    498
Glu Leu Ser Ser Thr Arg Lys Leu Ser Lys T yr Ser Asn Pro Val Ala
         125                 130                 135 gtc atc ata acg caa cta acc atc acc act a ag gtc cat tcc tta cta    546
Val Ile Ile Thr Gln Leu Thr Ile Thr Thr L ys Val His Ser Leu Leu
     140                 145                 150 gaa ggc atc tca aat tat ttt acc aag tgg a at aag cac atg atg gac    594
Glu Gly Ile Ser Asn Tyr Phe Thr Lys Trp A sn Lys His Met Met Asp
 155                 160                 165
```

```
acc aga gac tgc cag gtt tcc ttt act ttt g ga ccc tgt gat tat cac       642
Thr Arg Asp Cys Gln Val Ser Phe Thr Phe G ly Pro Cys Asp Tyr His
170                     175                 180                 185 cag gaa gtt tct ctt agg gtc cac ctg atg g aa tac att aca aaa caa       690
Gln Glu Val Ser Leu Arg Val His Leu Met G lu Tyr Ile Thr Lys Gln
            190                 195                 200 ggt ttc acg atc cgc aac acc cgg gtg cat c ac atg agt gag cgg gcc       738
Gly Phe Thr Ile Arg Asn Thr Arg Val His H is Met Ser Glu Arg Ala
        205                 210                 215 aat gaa aac aca gtg gag cac aac tgg act t tc tgt agg cta gcc cgg       786
Asn Glu Asn Thr Val Glu His Asn Trp Thr P he Cys Arg Leu Ala Arg
            220                 225                 230 aag aca gac gac t gatctccgac cctgccacag gttcctggaa   agactctcca        839
Lys Thr Asp Asp
        235 ggaaatggaa gatactgatt tttttttta aatcacagtg tgagatattt t ttttctttt      899 aaatagttgt atttatttga aggcagtgag gaccagaagg aagttttgtg c tttggcaga     959 ctcctccatg ttttgttccc ttccccctga gtatgcatgt gcctgttcag a gtctccaga   1019 taccttttt ataaaagaa gtctgaaaat cattatggta tataatctac c cttaacaga    1079 gcttttctta ttacagtgct aaaatgattt ctgataaaat ggtccctaac t caactagaa   1139 ggctaaaaat acaagaatga agaataagc agagtactca tgatgccttt g agaaaatc    1199 aaaacatcat gtagggtgac ctagtttcca aaccaataaa taagtagtat t gtaatatta   1259 aaggaaaact gttccaatca tttaaaagta cttattaagt actgctttt a cagttatga    1319 caactgtttc tttctatgca tataaatcaa ggaaccaaat atctgtagcc a tggaaatgt   1379 ctgactagaa atatttatat tgaattctga atacaaaatg tccctgtggt a gaaaactta  1439 ctctttatgc ctggtgcagt ataattccca agtgtactgt ctaccagaaa a aaaaaacaa   1499 aactaataaa aaatgaaata tgaaaaaaaa aaaaaaaaa aaa                         1542

<210> SEQ ID NO 25
<211> LENGTH: 237
<212> TYPE: PRT
<213> ORGANISM: H. sapiens

<400> SEQUENCE: 25

Met Asp Asn Gly Asp Trp Gly Tyr Met Met T hr Asp Pro Val Thr Leu
1               5                   10                  15

Asn Val Gly Gly His Leu Tyr Thr Thr Ser L eu Thr Thr Leu Thr Arg
            20                  25                  30

Tyr Pro Asp Ser Met Leu Gly Ala Met Phe G ly Gly Asp Phe Pro Thr
        35                  40                  45

Ala Arg Asp Pro Gln Gly Asn Tyr Phe Ile A sp Arg Asp Gly Pro Leu
    50                  55                  60

Phe Arg Tyr Val Leu Asn Phe Leu Arg Thr S er Glu Leu Thr Leu Pro
65                  70                  75                  80

Leu Asp Phe Lys Glu Phe Asp Leu Leu Arg L ys Glu Ala Asp Phe Tyr
                85                  90                  95

Gln Ile Glu Pro Leu Ile Gln Cys Leu Asn A sp Pro Lys Pro Leu Tyr
            100                 105                 110

Pro Met Asp Thr Phe Glu Glu Val Val Glu L eu Ser Ser Thr Arg Lys
        115                 120                 125

Leu Ser Lys Tyr Ser Asn Pro Val Ala Val I le Ile Thr Gln Leu Thr
    130                 135                 140
```

```
Ile Thr Thr Lys Val His Ser Leu Leu Glu G ly Ile Ser Asn Tyr Phe
145                 150                 155                 160

Thr Lys Trp Asn Lys His Met Met Asp Thr A rg Asp Cys Gln Val Ser
                165                 170                 175

Phe Thr Phe Gly Pro Cys Asp Tyr His Gln G lu Val Ser Leu Arg Val
            180                 185                 190

His Leu Met Glu Tyr Ile Thr Lys Gln Gly P he Thr Ile Arg Asn Thr
        195                 200                 205

Arg Val His His Met Ser Glu Arg Ala Asn G lu Asn Thr Val Glu His
    210                 215                 220

Asn Trp Thr Phe Cys Arg Leu Ala Arg Lys T hr Asp Asp
225                 230                 235

<210> SEQ ID NO 26
<211> LENGTH: 3204
<212> TYPE: DNA
<213> ORGANISM: H. sapiens
<220> FEATURE:
<221> NAME/KEY: CDS
<222> LOCATION: (182)...(1349)
<223> OTHER INFORMATION: K+Hnov42

<400> SEQUENCE: 26
cggccgaacc ttgggtgtgg gacagagtgc gtgcgtgtgg tgtgtcccca a gggcaggaa      60 ggtggcgaag ggaggcgaat ccgagtgggt ggagggaggg gaaggcgggg a ggagaaaaa    120 ggtgggagga ggaccaggtg ggaggtggc ggctcactca ggacccagcg g gggcagcgc     180 g atg agg cgg gtg acc ctg ttc ctg aac ggc  agc ccc aag aac gga aag    229
  Met Arg Arg Val Thr Leu Phe Leu Asn Gly  Ser Pro Lys Asn Gly Lys
  1               5                   10                  15 gtg gtt gct gta tat gga act tta tct gat t tg ctt tct gtg gcc agc      277
Val Val Ala Val Tyr Gly Thr Leu Ser Asp L eu Leu Ser Val Ala Ser
                20                  25                  30 agt aaa ctc ggc ata aaa gcc acc agt gtg t at aat ggg aaa ggt gga      325
Ser Lys Leu Gly Ile Lys Ala Thr Ser Val T yr Asn Gly Lys Gly Gly
            35                  40                  45 ctg att gat gat att gct ttg atc agg gat g at gat gtt ttg ttt gtt      373
Leu Ile Asp Asp Ile Ala Leu Ile Arg Asp A sp Asp Val Leu Phe Val
        50                  55                  60 tgt gaa gga gag cca ttt att gat cct cag a ca gat tct aag cct cct      421
Cys Glu Gly Glu Pro Phe Ile Asp Pro Gln T hr Asp Ser Lys Pro Pro
65                  70                  75                  80 gag gga ttg tta gga ttc cac aca gac tgg c tg aca tta aat gtt gga      469
Glu Gly Leu Leu Gly Phe His Thr Asp Trp L eu Thr Leu Asn Val Gly
                85                  90                  95 ggg cgg tac ttt aca act aca cgg agc act t ta gtg aat aaa gaa cct      517
Gly Arg Tyr Phe Thr Thr Thr Arg Ser Thr L eu Val Asn Lys Glu Pro
                100                 105                 110 gac agt atg ctg gcc cac atg ttt aag gac a aa ggt gtc tgg gga aat      565
Asp Ser Met Leu Ala His Met Phe Lys Asp L ys Gly Val Trp Gly Asn
            115                 120                 125 aag caa gat cat aga gga gct ttc tta att g ac cga agt cct gag tac      613
Lys Gln Asp His Arg Gly Ala Phe Leu Ile A sp Arg Ser Pro Glu Tyr
        130                 135                 140 ttc gaa ccc att ttg aac tac ttg cgt cat g ga cag ctc att gta aat      661
Phe Glu Pro Ile Leu Asn Tyr Leu Arg His G ly Gln Leu Ile Val Asn
145                 150                 155                 160 gat ggc att aat tta ttg ggt gtg tta gaa g aa gca aga ttt ttt ggt      709
Asp Gly Ile Asn Leu Leu Gly Val Leu Glu G lu Ala Arg Phe Phe Gly
                165                 170                 175
```

```
att gac tca ttg att gaa cac cta gaa gtg g ca ata aag aat tct caa         757
Ile Asp Ser Leu Ile Glu His Leu Glu Val A la Ile Lys Asn Ser Gln
            180                 185                 190 cca ccg gag gat cat tca cca ata tcc cga a ag gaa ttt gtc cga ttt         805
Pro Pro Glu Asp His Ser Pro Ile Ser Arg L ys Glu Phe Val Arg Phe
            195                 200                 205 ttg cta gca act cca acc aag tca gaa ctg c ga tgc cag ggt ttg aac         853
Leu Leu Ala Thr Pro Thr Lys Ser Glu Leu A rg Cys Gln Gly Leu Asn
            210                 215                 220 ttc agt ggt gct gat ctt tct cgt ttg gac c tt cga tac att aac ttc         901
Phe Ser Gly Ala Asp Leu Ser Arg Leu Asp L eu Arg Tyr Ile Asn Phe
225                 230                 235                 240 aaa atg gcc aat tta agc cgc tgt aat ctt g ca cat gca aat ctt tgc         949
Lys Met Ala Asn Leu Ser Arg Cys Asn Leu A la His Ala Asn Leu Cys
            245                 250                 255 tgt gca aat ctt gaa cga gct gat ctc tct g ga tca gtg ctt gac tgt         997
Cys Ala Asn Leu Glu Arg Ala Asp Leu Ser G ly Ser Val Leu Asp Cys
            260                 265                 270 gcg aat ctc cag gga gtc aag atg ctc tgt t ct aat gca gaa gga gca        1045
Ala Asn Leu Gln Gly Val Lys Met Leu Cys S er Asn Ala Glu Gly Ala
            275                 280                 285 tcc ctg aaa ctg tgt aat ttt gag gat cct t ct ggt ctt aaa gcc aat        1093
Ser Leu Lys Leu Cys Asn Phe Glu Asp Pro S er Gly Leu Lys Ala Asn
            290                 295                 300 tta gaa ggt gct aat ctg aaa ggt gtg gat a tg gaa gga agt cag atg        1141
Leu Glu Gly Ala Asn Leu Lys Gly Val Asp M et Glu Gly Ser Gln Met
305                 310                 315                 320 aca gga att aac ctg aga gtg gct acc tta a aa aat gca aag ttg aag        1189
Thr Gly Ile Asn Leu Arg Val Ala Thr Leu L ys Asn Ala Lys Leu Lys
            325                 330                 335 aac tgt aac ctc aga gga gca act ctg gca g ga act gat tta gag aat        1237
Asn Cys Asn Leu Arg Gly Ala Thr Leu Ala G ly Thr Asp Leu Glu Asn
            340                 345                 350 tgt gat ctg tct ggg tgt gat ctt caa gaa g cc aac ctg aga ggg tcc        1285
Cys Asp Leu Ser Gly Cys Asp Leu Gln Glu A la Asn Leu Arg Gly Ser
            355                 360                 365 aac gtg aag gga gct ata ttt gaa gag atg c tg aca cca cta cac atg        1333
Asn Val Lys Gly Ala Ile Phe Glu Glu Met L eu Thr Pro Leu His Met
            370                 375                 380 tca caa agt gtc aga t gagaatttta ggggctggag aa gatgtaa aagatgaaaa      1389
Ser Gln Ser Val Arg
385 tgttttcctt atcacttttc tttctccacc cactcagttg tctagaagaa a taacactgt      1449 aaggaaattt taaaaaaaaa catttagagg attatgcttg ttttgagtgg t gcataaggg      1509 aaaaaactga cttttttttcc atattctgat ttttaacaga aaagcactca t ttaatagat    1569 gtagggaaac tagatattgc tgcctttttga atgggggtagg ggggtttacc t tggttttatg  1629 accaggcata gtatctatta tatttgcttt taaataggca tgatgtggaa a taccatctt     1689 ggtttgagat gcatttgagg attttaattt atggaaagca caacatatgc a attatattt     1749 attgaattcc tagatgcagt atggatattt aaattgttaa aactttatga a aacttggaa     1809 aaggttgttc aggtttataa atagctttag tgatgcctcc cctctttaaa t acctgtcac     1869 accgtatgaa tatggtgaga tcagactccc taagactctt ttcaggttca t ttttataat    1929 gtttactttt taggacagaa cagtagctaa attaaagtaa tatccagttc t tactgattg    1989 agacagagtg gaaagaaaga catcattgta catcactgtc attccaaagg t acagtgtaa   2049
```

-continued

```
ctctggatgg aggaataact tacctatcac tacaacactt acaaatgaga a tttctcaga    2109 atttcattct aggcaagttc cactcaacac cagatcaagc aattctatct a tttacacta    2169 ttagcctagt tttctcatac agtcatcaca agcataggaa gatacttcaa a accaaaaaa    2229 accaaggtgc atcattaata ttcatttaat tcaaatacca aatagtttac a tagggccag    2289 cttagaaata gatactaaat ccagagctac tgcaatcaaa gcttatatga g tgaatatgg    2349 tagagttgcc tgctaaaagg caatgtaata taattgcagc tagaacccta c agtggggaa    2409 tgaggaattt taaacacaca tttgattaca gccaccaaaa aaatagacgt a aaaataaag    2469 gcatttggct ggtccaagat gtaattttca atcagtcagc acctgtgatt c ttttactta    2529 ttttttttgtg gttttttttt tttaaacaaa tttagcccaa attttcttga g tcattctct    2589 ctctgcagca gcagaggaag ggcctgtacc tccctaccaa tgacttggtg t ccttatttt    2649 ctaccccaag agcagggata ttagctgtgt ccaaatgggt tctgaattct a cagactcat    2709 caacatgagg caaggaatca ttgaaaacca cctgtgtctc ctttgggaga a tgacatatc    2769 tttagtattt acgtagctta ttcttctata tctacatatg caaagctttc c ttaacagta    2829 aagggtacat atgcatagtg ggaggagatc agacctttac aagtgaagga a agcaacttc    2889 agaaatgaat tattttcttt gctttattat ttttaccaag acagaagt a ttgtattga     2949 gagataatct attttcataa tcaatatgtg cctaaattat atttaaatca t ttcactctg    3009 tactatattt tcaggaatta cagaatgtgg tattcattca cttaaaggta c ctctgtaga    3069 aataacctaa aactgcagaa ggatctgaaa gatctaaaca tggtgtgctt a gaaactgca    3129 gattttagat ctaatgtata ctgcattaat aaatgatata agtgtttgt t gaaaaaaaa    3189 aaaaaaaaaa aaaaa                                                      3204
```

<210> SEQ ID NO 27
<211> LENGTH: 389
<212> TYPE: PRT
<213> ORGANISM: H. sapiens

<400> SEQUENCE: 27

```
Met Arg Arg Val Thr Leu Phe Leu Asn Gly S er Pro Lys Asn Gly Lys
 1               5                  10                  15

Val Val Ala Val Tyr Gly Thr Leu Ser Asp L eu Leu Ser Val Ala Ser
            20                  25                  30

Ser Lys Leu Gly Ile Lys Ala Thr Ser Val T yr Asn Gly Lys Gly Gly
        35                  40                  45

Leu Ile Asp Asp Ile Ala Leu Ile Arg Asp A sp Asp Val Leu Phe Val
    50                  55                  60

Cys Glu Gly Glu Pro Phe Ile Asp Pro Gln T hr Asp Ser Lys Pro Pro
65                  70                  75                  80

Glu Gly Leu Leu Gly Phe His Thr Asp Trp L eu Thr Leu Asn Val Gly
                85                  90                  95

Gly Arg Tyr Phe Thr Thr Thr Arg Ser Thr L eu Val Asn Lys Glu Pro
            100                 105                 110

Asp Ser Met Leu Ala His Met Phe Lys Asp L ys Gly Val Trp Gly Asn
        115                 120                 125

Lys Gln Asp His Arg Gly Ala Phe Leu Ile A sp Arg Ser Pro Glu Tyr
    130                 135                 140

Phe Glu Pro Ile Leu Asn Tyr Leu Arg His G ly Gln Leu Ile Val Asn
145                 150                 155                 160

Asp Gly Ile Asn Leu Leu Gly Val Leu Glu G lu Ala Arg Phe Phe Gly
```

-continued

```
                    165                 170                 175
    Ile Asp Ser Leu Ile Glu His Leu Glu Val A la Ile Lys Asn Ser Gln
                180                 185                 190

Pro Pro Glu Asp His Ser Pro Ile Ser Arg L ys Glu Phe Val Arg Phe
            195                 200                 205

Leu Leu Ala Thr Pro Thr Lys Ser Glu Leu A rg Cys Gln Gly Leu Asn
        210                 215                 220

Phe Ser Gly Ala Asp Leu Ser Arg Leu Asp L eu Arg Tyr Ile Asn Phe
    225                 230                 235                 240

Lys Met Ala Asn Leu Ser Arg Cys Asn Leu A la His Ala Asn Leu Cys
                    245                 250                 255

Cys Ala Asn Leu Glu Arg Ala Asp Leu Ser G ly Ser Val Leu Asp Cys
                260                 265                 270

Ala Asn Leu Gln Gly Val Lys Met Leu Cys S er Asn Ala Glu Gly Ala
            275                 280                 285

Ser Leu Lys Leu Cys Asn Phe Glu Asp Pro S er Gly Leu Lys Ala Asn
        290                 295                 300

Leu Glu Gly Ala Asn Leu Lys Gly Val Asp M et Glu Gly Ser Gln Met
    305                 310                 315                 320

Thr Gly Ile Asn Leu Arg Val Ala Thr Leu L ys Asn Ala Lys Leu Lys
                    325                 330                 335

Asn Cys Asn Leu Arg Gly Ala Thr Leu Ala G ly Thr Asp Leu Glu Asn
                340                 345                 350

Cys Asp Leu Ser Gly Cys Asp Leu Gln Glu A la Asn Leu Arg Gly Ser
            355                 360                 365

Asn Val Lys Gly Ala Ile Phe Glu Glu Met L eu Thr Pro Leu His Met
        370                 375                 380

Ser Gln Ser Val Arg
    385

<210> SEQ ID NO 28
<211> LENGTH: 1246
<212> TYPE: DNA
<213> ORGANISM: H. sapiens
<220> FEATURE:
<221> NAME/KEY: CDS
<222> LOCATION: (432)...(1092)
<223> OTHER INFORMATION: K+Hnov44, splice 1

<400> SEQUENCE: 28
cagaaaacca cgcaggtcct tcttgatcat ctagaactga ccgctccgcc t tgccaggag      60 tctgcagaac cacgtggcta gcctgcctga agttctcacc tctccaggaa g gcgggggc     120 ttctaatggc tgcagctgcg ctgggggctg gggctcccg ctgggactcc a cttccgtgg     180 atgtctaagc ttcacctttc ttgcgcccgc aggggcatga ctcaggtgaa a gggagccat    240 tttctcagac ccctggcctc atgcagccct tcagcatccc cgtgcaaatc a cacttcagg   300 gcagccggag cgccaggggg aggacagcct ttcctgcctc agggaagaag a gagagacag   360 actacagtga tggagaccca ctagatgtgc acaagaggct gccatccagt g ctggagagg   420 accgagccgt g atg ctg ggg ttt gcc atg atg ggc  ttc tca gtc cta atg       470
              Met Leu Gly Phe Ala Met Met Gly   Phe Ser Val Leu Met
               1                5                            10 ttc ttc ttg ctc gga aca acc att cta aag c ct ttt atg ctc agc att      518
Phe Phe Leu Leu Gly Thr Thr Ile Leu Lys P ro Phe Met Leu Ser Ile
 15                  20                  25 cag aga gaa gaa tcg acc tgc act gcc atc c ac aca gat atc atg gac     566
```

-continued

```
                  Gln Arg Glu Glu Ser Thr Cys Thr Ala Ile H is Thr Asp Ile Met Asp
                   30                  35                  40                  45 gac tgg ctg gac tgt gcc ttc acc tgt ggt g tg cac tgc cac ggt cag           614
Asp Trp Leu Asp Cys Ala Phe Thr Cys Gly V al His Cys His Gly Gln
                 50                  55                  60 ggg aag tac ccg tgt ctt cag gtg ttt gtg a ac ctc agc cat cca ggt           662
Gly Lys Tyr Pro Cys Leu Gln Val Phe Val A sn Leu Ser His Pro Gly
             65                  70                  75 cag aaa gct ctc cta cat tat aat gaa gag g ct gtc cag ata aat ccc           710
Gln Lys Ala Leu Leu His Tyr Asn Glu Glu A la Val Gln Ile Asn Pro
         80                  85                  90 aag tgc ttt tac aca cct aag tgc cac caa g at aga aat gat ttg ctc           758
Lys Cys Phe Tyr Thr Pro Lys Cys His Gln A sp Arg Asn Asp Leu Leu
     95                 100                 105 aac agt gct ctg gac ata aaa gaa ttc ttc g at cac aaa aat gga act           806
Asn Ser Ala Leu Asp Ile Lys Glu Phe Phe A sp His Lys Asn Gly Thr
110                 115                 120                 125 ccc ttt tca tgc ttc tac agt cca gcc agc c aa tct gaa gat gtc att           854
Pro Phe Ser Cys Phe Tyr Ser Pro Ala Ser G ln Ser Glu Asp Val Ile
                130                 135                 140 ctt ata aaa aag tat gac caa atg gct atc t tc cac tgt tta ttt tgg          902
Leu Ile Lys Lys Tyr Asp Gln Met Ala Ile P he His Cys Leu Phe Trp
            145                 150                 155 cct tca ctg act ctg cta ggt ggt gcc ctg a tt gtt ggc atg gtg aga          950
Pro Ser Leu Thr Leu Leu Gly Gly Ala Leu I le Val Gly Met Val Arg
        160                 165                 170 tta aca caa cac ctg tcc tta ctg tgt gaa a aa tat agc act gta gtc          998
Leu Thr Gln His Leu Ser Leu Leu Cys Glu L ys Tyr Ser Thr Val Val
    175                 180                 185 aga gat gag gta ggt gga aaa gta cct tat a ta gaa cag cat cag ttc         1046
Arg Asp Glu Val Gly Gly Lys Val Pro Tyr I le Glu Gln His Gln Phe
190                 195                 200                 205 aaa ctg tgc att atg agg agg agc aaa gga a ga gca gag aaa tct t           1092
Lys Leu Cys Ile Met Arg Arg Ser Lys Gly A rg Ala Glu Lys Ser
                210                 215                 220 aagacggtgg ccaaattaaa gtgctggcct tcagatgtct gtgatttctg c aactgagga       1152 cctaattatg cctgtctgca aactaataat gtaaaggta ataattaaag t atcatattt        1212 tcatgtggga aaaaaaaaaa aaaaaaaaaa aaaa                                    1246
```

<210> SEQ ID NO 29
<211> LENGTH: 1111
<212> TYPE: DNA
<213> ORGANISM: H. sapiens
<220> FEATURE:
<221> NAME/KEY: CDS
<222> LOCATION: (297)...(957)
<223> OTHER INFORMATION: K+Hnov44, splice 2

<400> SEQUENCE: 29

```
aaaaccatg acttgtggca ccagaagaga gccggggact tcaatccaag a aagcagaga         60 agataccaaa gaaggaccga gaagggcaaa gcaaagaaga ctgtaccatg t cctaagctg       120 aggcaggcgg caggcgtggt gcacaagaag tctgagtgtg aggggctctt t tctctccac      180 tgccaatgac agccttttcct gcctcaggga agaagagaga gacagactac a gtgatggag     240 acccactaga tgtgcacaag aggctgccat ccagtgctgg agaggaccga g ccgtg atg       299
                                                                  Met
                                                                   1 ctg ggg ttt gcc atg atg ggc ttc tca gtc c ta atg ttc ttc ttg ctc         347
Leu Gly Phe Ala Met Met Gly Phe Ser Val L eu Met Phe Phe Leu Leu
```

```
                  5                    10                   15
gga aca acc att cta aag cct ttt atg ctc a gc att cag aga gaa gaa      395
Gly Thr Thr Ile Leu Lys Pro Phe Met Leu S er Ile Gln Arg Glu Glu
         20                  25                  30 tcg acc tgc act gcc atc cac aca gat atc a tg gac gac tgg ctg gac      443
Ser Thr Cys Thr Ala Ile His Thr Asp Ile M et Asp Asp Trp Leu Asp
     35                  40                  45 tgt gcc ttc acc tgt ggt gtg cac tgc cac g gt cag ggg aag tac ccg      491
Cys Ala Phe Thr Cys Gly Val His Cys His G ly Gln Gly Lys Tyr Pro
 50                  55                  60                      65 tgt ctt cag gtg ttt gtg aac ctc agc cat c ca ggt cag aaa gct ctc      539
Cys Leu Gln Val Phe Val Asn Leu Ser His P ro Gly Gln Lys Ala Leu
                 70                  75                  80 cta cat tat aat gaa gag gct gtc cag ata a at ccc aag tgc ttt tac      587
Leu His Tyr Asn Glu Glu Ala Val Gln Ile A sn Pro Lys Cys Phe Tyr
             85                  90                  95 aca cct aag tgc cac caa gat aga aat gat t tg ctc aac agt gct ctg      635
Thr Pro Lys Cys His Gln Asp Arg Asn Asp L eu Leu Asn Ser Ala Leu
        100                 105                 110 gac ata aaa gaa ttc ttc gat cac aaa aat g ga act ccc ttt tca tgc      683
Asp Ile Lys Glu Phe Phe Asp His Lys Asn G ly Thr Pro Phe Ser Cys
    115                 120                 125 ttc tac agt cca gcc agc caa tct gaa gat g tc att ctt ata aaa aag      731
Phe Tyr Ser Pro Ala Ser Gln Ser Glu Asp V al Ile Leu Ile Lys Lys
130                 135                 140                 145 tat gac caa atg gct atc ttc cac tgt tta t tt tgg cct tca ctg act      779
Tyr Asp Gln Met Ala Ile Phe His Cys Leu P he Trp Pro Ser Leu Thr
                150                 155                 160 ctg cta ggt ggt gcc ctg att gtt ggc atg g tg aga tta aca caa cac      827
Leu Leu Gly Gly Ala Leu Ile Val Gly Met V al Arg Leu Thr Gln His
            165                 170                 175 ctg tcc tta ctg tgt gaa aaa tat agc act g ta gtc aga gat gag gta      875
Leu Ser Leu Leu Cys Glu Lys Tyr Ser Thr V al Val Arg Asp Glu Val
        180                 185                 190 ggt gga aaa gta cct tat ata gaa cag cat c ag ttc aaa ctg tgc att      923
Gly Gly Lys Val Pro Tyr Ile Glu Gln His G ln Phe Lys Leu Cys Ile
    195                 200                 205 atg agg agg agc aaa gga aga gca gag aaa t ct t aagacggtgg             967
Met Arg Arg Ser Lys Gly Arg Ala Glu Lys S er
210                 215                 220 ccaaattaaa gtgctggcct tcagatgtct gtgatttctg caactgagga c ctaattatg   1027 cctgtctgca aactaataat gtaaaggta ataattaaag tatcatattt t catgtggga    1087 aaaaaaaaaa aaaaaaaaaa aaaa                                          1111

<210> SEQ ID NO 30
<211> LENGTH: 220
<212> TYPE: PRT
<213> ORGANISM: H. sapiens

<400> SEQUENCE: 30

Met Leu Gly Phe Ala Met Met Gly Phe Ser V al Leu Met Phe Phe Leu
 1               5                   10                  15

Leu Gly Thr Thr Ile Leu Lys Pro Phe Met L eu Ser Ile Gln Arg Glu
            20                  25                  30

Glu Ser Thr Cys Thr Ala Ile His Thr Asp I le Met Asp Asp Trp Leu
        35                  40                  45

Asp Cys Ala Phe Thr Cys Gly Val His Cys H is Gly Gln Gly Lys Tyr
    50                  55                  60
```

Pro Cys Leu Gln Val Phe Val Asn Leu Ser His Pro Gly Gln Lys Ala
 65                  70                  75                  80

Leu Leu His Tyr Asn Glu Glu Ala Val Gln Ile Asn Pro Lys Cys Phe
                 85                  90                  95

Tyr Thr Pro Lys Cys His Gln Asp Arg Asn Asp Leu Leu Asn Ser Ala
            100                 105                 110

Leu Asp Ile Lys Glu Phe Phe Asp His Lys Asn Gly Thr Pro Phe Ser
        115                 120                 125

Cys Phe Tyr Ser Pro Ala Ser Gln Ser Glu Asp Val Ile Leu Ile Lys
    130                 135                 140

Lys Tyr Asp Gln Met Ala Ile Phe His Cys Leu Phe Trp Pro Ser Leu
145                 150                 155                 160

Thr Leu Leu Gly Gly Ala Leu Ile Val Gly Met Val Arg Leu Thr Gln
                165                 170                 175

His Leu Ser Leu Leu Cys Glu Lys Tyr Ser Thr Val Val Arg Asp Glu
            180                 185                 190

Val Gly Gly Lys Val Pro Tyr Ile Glu Gln His Gln Phe Lys Leu Cys
        195                 200                 205

Ile Met Arg Arg Ser Lys Gly Arg Ala Glu Lys Ser
    210                 215                 220

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
tatccacatc aatggacaaa gc                                             22

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tgcataactg gctgggtgta                                                20

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
tgacatcact ggatgaactt ga                                             22

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tgcctgcaaa gtttgaacat                                                20

```
<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tgacatcact ggatgaactt ga                                              22

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
tgcctgcaaa gtttgaacat                                                 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
acctggtggt atggaagcat                                                 20

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
tttctcctgg cctctaccc                                                  19

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
tccctcttgg gtgaccttc                                                  19

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
atctttgtca gccaccagct                                                 20

<210> SEQ ID NO 41
<211> LENGTH: 24
<212> TYPE: DNA
<213> ORGANISM: Artificial Sequence
<220> FEATURE:
<223> OTHER INFORMATION: Primer
```

```
<400> SEQUENCE: 41
aggtgtgctg ccatctgctg ttcg                                          24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
agcctatcct ctctgagagt cagg                                          24

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
aagcagagta ctcatgatgc c                                             21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tctggtagac agtacagtgg                                               20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
catttggctg gtccaagatg                                               20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
agtcattggt agggaggtac                                               20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
catgcttcta cagtccagcc                                               20

<210> SEQ ID NO 48
```

```
<211> LENGTH: 20
<212> TYPE: DNA
<213> ORGANISM: Artificial Sequence
<220> FEATURE:
<223> OTHER INFORMATION: Primer

<400> SEQUENCE: 48
ggtcctcagt tgcagaaatc                                              20

<210> SEQ ID NO 49
<211> LENGTH: 45
<212> TYPE: DNA
<213> ORGANISM: Artificial Sequence
<220> FEATURE:
<223> OTHER INFORMATION: Primer

<400> SEQUENCE: 49
tggtgggctg tggtgaccat gacaactgtg ggctatgggg acatg                  45

<210> SEQ ID NO 50
<211> LENGTH: 45
<212> TYPE: DNA
<213> ORGANISM: Artificial Sequence
<220> FEATURE:
<223> OTHER INFORMATION: Primer

<400> SEQUENCE: 50
tggtgggcag tggtcaccat gaccactgtg ggctacgggg acatg                  45

<210> SEQ ID NO 51
<211> LENGTH: 45
<212> TYPE: DNA
<213> ORGANISM: Artificial Sequence
<220> FEATURE:
<223> OTHER INFORMATION: Primer

<400> SEQUENCE: 51
tggtgggcag tcgtctccat gacaactgta ggctatggag acatg                  45

<210> SEQ ID NO 52
<211> LENGTH: 45
<212> TYPE: DNA
<213> ORGANISM: Artificial Sequence
<220> FEATURE:
<223> OTHER INFORMATION: Primer

<400> SEQUENCE: 52
tggtgggcag tggtaaccat gacaacagtg ggttacggcg atatg                  45

<210> SEQ ID NO 53
<211> LENGTH: 45
<212> TYPE: DNA
<213> ORGANISM: Artificial Sequence
<220> FEATURE:
<223> OTHER INFORMATION: Primer

<400> SEQUENCE: 53
tggtgggctg tggtcaccat gacgaccctg ggctatggag acatg                  45

<210> SEQ ID NO 54
<211> LENGTH: 45
<212> TYPE: DNA
<213> ORGANISM: Artificial Sequence
<220> FEATURE:
<223> OTHER INFORMATION: Primer

<400> SEQUENCE: 54
```
tggtgggggg tggtcacagt caccaccatc ggctatgggg acaag       45

<210> SEQ ID NO 55
<211> LENGTH: 45
<212> TYPE: DNA
<213> ORGANISM: Artificial Sequence
<220> FEATURE:
<223> OTHER INFORMATION: Primer

<400> SEQUENCE: 55
tggtgggcag tggtcaccat gaccacggtt ggctatgggg acatg       45

<210> SEQ ID NO 56
<211> LENGTH: 45
<212> TYPE: DNA
<213> ORGANISM: Artificial Sequence
<220> FEATURE:
<223> OTHER INFORMATION: Primer

<400> SEQUENCE: 56
tggtgggccg tggtcaccat gacgaccctg ggctatggag acatg       45

<210> SEQ ID NO 57
<211> LENGTH: 45
<212> TYPE: DNA
<213> ORGANISM: Artificial Sequence
<220> FEATURE:
<223> OTHER INFORMATION: Primer

<400> SEQUENCE: 57
tggtgggctg tggtcaccat gacgacactg ggctacggag acatg       45

<210> SEQ ID NO 58
<211> LENGTH: 45
<212> TYPE: DNA
<213> ORGANISM: Artificial Sequence
<220> FEATURE:
<223> OTHER INFORMATION: Primer

<400> SEQUENCE: 58
tggtgggctg tggtgaccat gacaactgtg ggctatgggg acatg       45

<210> SEQ ID NO 59
<211> LENGTH: 47
<212> TYPE: DNA
<213> ORGANISM: Artificial Sequence
<220> FEATURE:
<223> OTHER INFORMATION: Primer

<400> SEQUENCE: 59
ttcctgttct ccattgagac cgaaacaacc attgggtatg gcttccg     47

<210> SEQ ID NO 60
<211> LENGTH: 47
<212> TYPE: DNA
<213> ORGANISM: Artificial Sequence
<220> FEATURE:
<223> OTHER INFORMATION: Primer

<400> SEQUENCE: 60
tttttattct caatagagac agaaaccacc attggttatg gctaccg     47

<210> SEQ ID NO 61
<211> LENGTH: 47
<212> TYPE: DNA

<213> ORGANISM: Artificial Sequence
<220> FEATURE:
<223> OTHER INFORMATION: Primer

<400> SEQUENCE: 61
ttcctcttct ccattgagac ccagacaacc ataggctatg gtttcag         47

<210> SEQ ID NO 62
<211> LENGTH: 47
<212> TYPE: DNA
<213> ORGANISM: Artificial Sequence
<220> FEATURE:
<223> OTHER INFORMATION: Primer

<400> SEQUENCE: 62
ttcctgttct cggtggagac gcagacgacc atcggctatg ggttccg         47

<210> SEQ ID NO 63
<211> LENGTH: 47
<212> TYPE: DNA
<213> ORGANISM: Artificial Sequence
<220> FEATURE:
<223> OTHER INFORMATION: Primer

<400> SEQUENCE: 63
ttcctcttct cccttgaatc ccaaaccacc attggctatg gcttccg         47

<210> SEQ ID NO 64
<211> LENGTH: 47
<212> TYPE: DNA
<213> ORGANISM: Artificial Sequence
<220> FEATURE:
<223> OTHER INFORMATION: Primer

<400> SEQUENCE: 64
tttctctttt ccctggaatc ccagacaacc attggctatg gagtccg         47

<210> SEQ ID NO 65
<211> LENGTH: 47
<212> TYPE: DNA
<213> ORGANISM: Artificial Sequence
<220> FEATURE:
<223> OTHER INFORMATION: Primer

<400> SEQUENCE: 65
ttccttttct ccattgaggt ccaagtgact attggctttg gggggcg         47

<210> SEQ ID NO 66
<211> LENGTH: 47
<212> TYPE: DNA
<213> ORGANISM: Artificial Sequence
<220> FEATURE:
<223> OTHER INFORMATION: Primer

<400> SEQUENCE: 66
tttctcttct ccattgaagt tcaagttacc attgggtttg gagggag         47

<210> SEQ ID NO 67
<211> LENGTH: 50
<212> TYPE: DNA
<213> ORGANISM: Artificial Sequence
<220> FEATURE:
<223> OTHER INFORMATION: Primer

<400> SEQUENCE: 67
gcgctctact tcaccttcag cagcctcacc agtgtgggct tcggcaacgt         50

<210> SEQ ID NO 68
<211> LENGTH: 15
<212> TYPE: PRT
<213> ORGANISM: Artificial Sequence
<220> FEATURE:
<223> OTHER INFORMATION: consensus sequences

<400> SEQUENCE: 68

Trp Trp Ala Val Val Ser Met Thr Thr Val Gly Tyr Gly Asp Met
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Primer

<400> SEQUENCE: 69

Trp Trp Ala Val Val Thr Met Thr Thr Leu Gly Tyr Gly Asp Met
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Primer

<400> SEQUENCE: 70

Trp Trp Gly Val Val Thr Val Thr Thr Ile Gly Tyr Gly Asp Lys
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Primer

<400> SEQUENCE: 71

Trp Trp Ala Val Val Thr Met Thr Thr Val Gly Tyr Gly Asp Met
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Primer

<400> SEQUENCE: 72

Phe Leu Phe Ser Ile Glu Val Gln Val Thr Ile Gly Phe Gly Gly
 1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Primer

<400> SEQUENCE: 73

Phe Leu Phe Ser Leu Glu Ser Gln Thr Thr Ile Gly Tyr Gly Val
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: Primer

<400> SEQUENCE: 74

Phe Leu Phe Ser Ile Glu Thr Glu Thr Thr Ile Gly Tyr Gly Tyr
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Primer

<400> SEQUENCE: 75

Phe Leu Phe Ser Ile Glu Thr Gln Thr Thr Ile Gly Tyr Gly Phe
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: Primer

<400> SEQUENCE: 76

Phe Leu Phe Ser Val Glu Thr Gln Thr Thr Ile Gly Tyr Gly Phe
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Primer

<400> SEQUENCE: 77

Phe Leu Phe Ser Leu Glu Ser Gln Thr Thr Ile Gly Tyr Gly Phe
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Primer

<400> SEQUENCE: 78

Phe Leu Phe Ser Ile Glu Thr Glu Thr Thr Ile Gly Tyr Gly Phe
 1               5                  10                  15

<210> SEQ ID NO 79
<211> LENGTH: 16
<212> TYPE: PRT
<213> ORGANISM: Artificial Sequence
<220> FEATURE:
<223> OTHER INFORMATION: Primer

<400> SEQUENCE: 79

Ala Leu Tyr Phe Thr Phe Ser Ser Leu Thr Ser Val Gly Phe Gly Asn
 1               5                  10                  15

-continued

```
<210> SEQ ID NO 80
<211> LENGTH: 2571
<212> TYPE: DNA
<213> ORGANISM: H. sapiens
<220> FEATURE:
<221> NAME/KEY: CDS
<222> LOCATION: (110)...(1051)

<400> SEQUENCE: 80
gctgccgcgc ctgtagcact cccggaactg gaactaggtg ccagacggtc c ggaggcggg        60 ggccacgtca gcggggccac ccagggctcg cggggtcccg gtgggtgcc at g cgg agg       118
                                                        Met Arg Arg
                                                         1 ggc gcg ctt ctg gcg ggc gcc ttg gcc gcg t ac gcc gcg tac ctg gtg        166
Gly Ala Leu Leu Ala Gly Ala Leu Ala Ala T yr Ala Ala Tyr Leu Val
  5                  10                  15 ctg ggc gcg ctg ttg gtg gcg cgg ctg gag g gg ccg cac gaa gcc agg        214
Leu Gly Ala Leu Leu Val Ala Arg Leu Glu G ly Pro His Glu Ala Arg
 20                  25                  30                  35 ctc cga gcc gag ctg gag acg ctg cgg gcg c ag ctg ctt cag cgc agc        262
Leu Arg Ala Glu Leu Glu Thr Leu Arg Ala G ln Leu Leu Gln Arg Ser
                 40                  45                  50 ccg tgt gtg gct gcc ccc gcc ctg gac gcc t tc gtg gag cga gtg ctg        310
Pro Cys Val Ala Ala Pro Ala Leu Asp Ala P he Val Glu Arg Val Leu
     55                  60                  65 gcg gcc gga cgg ctg ggg cgg gtc gtg ctt g ct aac gct tcg ggg tcc        358
Ala Ala Gly Arg Leu Gly Arg Val Val Leu A la Asn Ala Ser Gly Ser
 70                  75                  80 gcc aac gcc tcg gac ccc gcc tgg gac ttc g cc tct gct ctc ttc ttc        406
Ala Asn Ala Ser Asp Pro Ala Trp Asp Phe A la Ser Ala Leu Phe Phe
 85                  90                  95 gcc agc acg ctg atc acc acc gtg ggc tat g gg tac aca acg cca ctg        454
Ala Ser Thr Leu Ile Thr Thr Val Gly Tyr G ly Tyr Thr Thr Pro Leu
100                 105                 110                 115 act gat gcg ggc aag gcc ttc tcc atc gcc t tt gcg ctc ctg ggc gtg        502
Thr Asp Ala Gly Lys Ala Phe Ser Ile Ala P he Ala Leu Leu Gly Val
                120                 125                 130 ccg acc acc atg ctg ctg ctg acc gcc tca g cc cag cgc ctg tca ctg        550
Pro Thr Thr Met Leu Leu Leu Thr Ala Ser A la Gln Arg Leu Ser Leu
                    135                 140                 145 ctg ctg act cac gtg ccc ctg tct tgg ctg a gc atg cgt tgg ggc tgg        598
Leu Leu Thr His Val Pro Leu Ser Trp Leu S er Met Arg Trp Gly Trp
                150                 155                 160 gac ccc cgg cgg gcg gcc tgc tgg cac ttg g tg gcc ctg ttg ggg gtc        646
Asp Pro Arg Arg Ala Ala Cys Trp His Leu V al Ala Leu Leu Gly Val
165                 170                 175 gta gtg acc gtc tgc ttt ctg gtg ccg gct g tg atc ttt gcc cac ctc        694
Val Val Thr Val Cys Phe Leu Val Pro Ala V al Ile Phe Ala His Leu
180                 185                 190                 195 gag gag gcc tgg agc ttc ttg gat gcc ttc t ac ttc tgc ttt atc tct        742
Glu Glu Ala Trp Ser Phe Leu Asp Ala Phe T yr Phe Cys Phe Ile Ser
                200                 205                 210 ctg tcc acc atc ggc ctg ggc gac tac gtg c cc ggg gag gcc cct ggc        790
Leu Ser Thr Ile Gly Leu Gly Asp Tyr Val P ro Gly Glu Ala Pro Gly
                215                 220                 225 cag ccc tac cgg gcc ctc tac aag gtg ctg g tc aca gtc tac ctc ttc        838
Gln Pro Tyr Arg Ala Leu Tyr Lys Val Leu V al Thr Val Tyr Leu Phe
                230                 235                 240 ctg ggc ctg gtg gcc atg gtg ctg gtg ctg c ag acc ttc cgc cac gtg        886
Leu Gly Leu Val Ala Met Val Leu Val Leu G ln Thr Phe Arg His Val
    245                 250                 255
```

```
tcc gac ctc cac ggc ctc acg gag ctc atc c tg ctg ccc cct ccg tgc    934
Ser Asp Leu His Gly Leu Thr Glu Leu Ile L eu Leu Pro Pro Pro Cys
260                 265                 270                 275 cct gcc agt ttc aat gcg gat gag gac gat c gg gtg gac atc ctg ggc    982
Pro Ala Ser Phe Asn Ala Asp Glu Asp Asp A rg Val Asp Ile Leu Gly
                280                 285                 290 ccc cag ccg gag tcg cac cag caa ctc tct g cc agc tcc cac acc gac   1030
Pro Gln Pro Glu Ser His Gln Gln Leu Ser A la Ser Ser His Thr Asp
            295                 300                 305 tac gct tcc atc ccc agg tag ctggggcagc tctgcca gg cttgggtgtg       1081
Tyr Ala Ser Ile Pro Arg
                310 cctggcctgg gactgagggg tccaggcgac cagagctggc tgtacaggaa t gtccacgag  1141
cacagcaggt gatcttgagg ccttgccgtc caccgtctct cctttgtttc c cagcatctg  1201
gctgggatgt gaagggcagc actccctgtc cccatgtccc gggctccact g ggcaccaac  1261
ataaccttgt tctctgtcct ttctctcatc ctctttacac tgtgtctctc t ggctctctg  1321
gcattctcgc tgcctctgtc tttccctctt gctgtctctg tttctcattc t ctttcatgt  1381
tccgtctgtg tctctcaatt aaccactcgt caactgctga ttctactggg c tgtgggctc  1441
agacctcatt tcaggcacca gattggtcgc tacaccctgg acaagtgact g cccgtctct  1501
gagccttgat ttcctcagct gccaaatggg aagaatagaa gaatttgccc c taaacccct  1561
cctgtgtgct ggccctgtgc tagacagtgc tggagacata gttgggggtg g agaactgcc  1621
cttatggagc ttgcagtcca gtgaggtgga cagacctgtc cccagacagt g atggcccaa  1681
aatggtcagc actttaatgg aggaggtgag gtgttgaaag cacaggcaga g tggtcaggg  1741
ctgaagtcgg agaagcatag ggactaggcc caatccagcc tggaaagtca g ggaggactt  1801
cctagaggaa gggacatcga actaagacct gaactatgag aaataggcag g aagaagttg  1861
tacctgactc atttttctca ggtgtctcca gggagcagga cccatggagg g acccctggt  1921
gtaggcctgg gcgatagact cttcctcagc agcctggcag gcaggaaaca g acataggac  1981
cccagcccag atctgaatgg catgggaggt gctgcccttta accatgacac c attgtaaga  2041
gctgtccaca tttgtatgtt gtgccctgga atcagcctgg ttgagctcaa a tcccaactt  2101
agccacgtct ggcctgtgtc cttgggcagt cacactacct ctctgatttt g tttccttat  2161
ctgtaaaatg gtgatcatca taatacaact tcaaaggat ttcaggctga g tgtggtggc  2221
tcacgcctat acacccagca cttggaagg ctgaggaagg aggatcgctt g aggccagga  2281
gtttgagact agcctaggca acacagtgag gccttatctc aacaacaacc a caaaatcta  2341
aaaattagct gggtgtggtg gtgcatgcct gtgatcctgg ctacttcaga g gctgaggtg  2401
gaaggatcac ttgaggccag gagtttgagg ctgcagtgag ttatgatggc a ctgctgcac  2461
tccagcctgc gggacagagt gagaccctgt ctgaaagaaa gagagaaaga a agaaagaaa  2521
gagagagaaa gaaagaaaga aagaaaggga aagatggaag gaaggaagga              2571
```

<210> SEQ ID NO 81
<211> LENGTH: 313
<212> TYPE: PRT
<213> ORGANISM: H. sapiens

<400> SEQUENCE: 81

```
Met Arg Arg Gly Ala Leu Leu Ala Gly Ala L eu Ala Ala Tyr Ala Ala
 1               5                  10                  15

Tyr Leu Val Leu Gly Ala Leu Leu Val Ala A rg Leu Glu Gly Pro His
```

```
                  20                  25                  30
Glu Ala Arg Leu Arg Ala Glu Leu Glu Thr L eu Arg Ala Gln Leu Leu
                35                  40                  45
Gln Arg Ser Pro Cys Val Ala Pro Ala L eu Asp Ala Phe Val Glu
        50                  55                  60
Arg Val Leu Ala Ala Gly Arg Leu Gly Arg V al Val Leu Ala Asn Ala
 65                  70                  75                  80
Ser Gly Ser Ala Asn Ala Ser Asp Pro Ala T rp Asp Phe Ala Ser Ala
                85                  90                  95
Leu Phe Phe Ala Ser Thr Leu Ile Thr Thr V al Gly Tyr Gly Tyr Thr
               100                 105                 110
Thr Pro Leu Thr Asp Ala Gly Lys Ala Phe S er Ile Ala Phe Ala Leu
               115                 120                 125
Leu Gly Val Pro Thr Thr Met Leu Leu Leu T hr Ala Ser Ala Gln Arg
           130                 135                 140
Leu Ser Leu Leu Leu Thr His Val Pro Leu S er Trp Leu Ser Met Arg
145                 150                 155                 160
Trp Gly Trp Asp Pro Arg Arg Ala Ala Cys T rp His Leu Val Ala Leu
               165                 170                 175
Leu Gly Val Val Val Thr Val Cys Phe Leu V al Pro Ala Val Ile Phe
               180                 185                 190
Ala His Leu Glu Glu Ala Trp Ser Phe Leu A sp Ala Phe Tyr Phe Cys
           195                 200                 205
Phe Ile Ser Leu Ser Thr Ile Gly Leu Gly A sp Tyr Val Pro Gly Glu
       210                 215                 220
Ala Pro Gly Gln Pro Tyr Arg Ala Leu Tyr L ys Val Leu Val Thr Val
225                 230                 235                 240
Tyr Leu Phe Leu Gly Leu Val Ala Met Val L eu Val Leu Gln Thr Phe
               245                 250                 255
Arg His Val Ser Asp Leu His Gly Leu Thr G lu Leu Ile Leu Leu Pro
           260                 265                 270
Pro Pro Cys Pro Ala Ser Phe Asn Ala Asp G lu Asp Asp Arg Val Asp
       275                 280                 285
Ile Leu Gly Pro Gln Pro Glu Ser His Gln G ln Leu Ser Ala Ser Ser
   290                 295                 300
His Thr Asp Tyr Ala Ser Ile Pro Arg
305                 310

<210> SEQ ID NO 82
<211> LENGTH: 3300
<212> TYPE: DNA
<213> ORGANISM: H. sapiens
<220> FEATURE:
<221> NAME/KEY: CDS
<222> LOCATION: (50)...(1285)

<400> SEQUENCE: 82
aaatgcctgc ccgtgcagct cggagcgcgc agcccgtctc tgaataaga at g gcg gca         58
                                                      Met Ala Ala
                                                        1 cct gac ttg ctg gat cct aaa tct gcc gct c ag aac tcc aaa ccg agg        106
Pro Asp Leu Leu Asp Pro Lys Ser Ala Ala G ln Asn Ser Lys Pro Arg
     5                  10                  15 ctc tcg ttt tcc acg aaa ccc aca gtg ctt g ct tcc cgg gtg gag agt       154
Leu Ser Phe Ser Thr Lys Pro Thr Val Leu A la Ser Arg Val Glu Ser
 20                  25                  30                  35
```

-continued

```
gac acg acc att aat gtt atg aaa tgg aag a cg gtc tcc acg ata ttc      202
Asp Thr Thr Ile Asn Val Met Lys Trp Lys T hr Val Ser Thr Ile Phe
                40                  45                  50 ctg gtg gtt gtc ctc tat ctg atc atc gga g cc acc gtg ttc aaa gca      250
Leu Val Val Val Leu Tyr Leu Ile Ile Gly A la Thr Val Phe Lys Ala
            55                  60                  65 ttg gag cag cct cat gag att tca cag agg a cc acc att gtg atc cag      298
Leu Glu Gln Pro His Glu Ile Ser Gln Arg T hr Thr Ile Val Ile Gln
        70                  75                  80 aag caa aca ttc ata tcc caa cat tcc tgt g tc aat tcg acg gag ctg      346
Lys Gln Thr Phe Ile Ser Gln His Ser Cys V al Asn Ser Thr Glu Leu
    85                  90                  95 gat gaa ctc att cag caa ata gtg gca gca a ta aat gca ggg att ata      394
Asp Glu Leu Ile Gln Gln Ile Val Ala Ala I le Asn Ala Gly Ile Ile
100                 105                 110                 115 ccg tta gga aac acc tcc aat caa atc agt c ac tgg gat ttg gga agt      442
Pro Leu Gly Asn Thr Ser Asn Gln Ile Ser H is Trp Asp Leu Gly Ser
                120                 125                 130 tcc ttc ttc ttt gct ggc act gtt att aca a cc ata gga ttt gga aac      490
Ser Phe Phe Phe Ala Gly Thr Val Ile Thr T hr Ile Gly Phe Gly Asn
            135                 140                 145 atc tca cca cgc aca gaa ggc ggc aaa ata t tc tgt atc atc tat gcc      538
Ile Ser Pro Arg Thr Glu Gly Gly Lys Ile P he Cys Ile Ile Tyr Ala
        150                 155                 160 tta ctg gga att ccc ctc ttt ggt ttt ctc t tg gct gga gtt gga gat      586
Leu Leu Gly Ile Pro Leu Phe Gly Phe Leu L eu Ala Gly Val Gly Asp
    165                 170                 175 cag cta ggc acc ata ttt gga aaa gga att g cc aaa gtg gaa gat acg      634
Gln Leu Gly Thr Ile Phe Gly Lys Gly Ile A la Lys Val Glu Asp Thr
180                 185                 190                 195 ttt att aag tgg aat gtt agt cag acc aag a tt cgc atc atc tca aca      682
Phe Ile Lys Trp Asn Val Ser Gln Thr Lys I le Arg Ile Ile Ser Thr
                200                 205                 210 atc ata ttt ata cta ttt ggc tgt gta ctc t tt gtg gct ctg cct gcg      730
Ile Ile Phe Ile Leu Phe Gly Cys Val Leu P he Val Ala Leu Pro Ala
            215                 220                 225 atc ata ttc aaa cac ata gaa ggc tgg agt g cc ctg gac gcc att tat      778
Ile Ile Phe Lys His Ile Glu Gly Trp Ser A la Leu Asp Ala Ile Tyr
        230                 235                 240 ttt gtg gtt atc act cta aca act att gga t tt ggt gac tac gtt gca      826
Phe Val Val Ile Thr Leu Thr Thr Ile Gly P he Gly Asp Tyr Val Ala
    245                 250                 255 ggt gga tcc gat att gaa tat ctg gac ttc t at aag cct gtc gtg tgg      874
Gly Gly Ser Asp Ile Glu Tyr Leu Asp Phe T yr Lys Pro Val Val Trp
260                 265                 270                 275 ttc tgg atc ctt gta ggg ctt gct tac ttt g ct gct gtc ctg agc atg      922
Phe Trp Ile Leu Val Gly Leu Ala Tyr Phe A la Ala Val Leu Ser Met
                280                 285                 290 att gga gat tgg ctc cga gtg ata tct aaa a ag aca aaa gaa gag gtg      970
Ile Gly Asp Trp Leu Arg Val Ile Ser Lys L ys Thr Lys Glu Glu Val
            295                 300                 305 gga gag ttc aga gca cac gct gct gag tgg a ca gcc aac gtc aca gcc     1018
Gly Glu Phe Arg Ala His Ala Ala Glu Trp T hr Ala Asn Val Thr Ala
        310                 315                 320 gaa ttc aaa gaa acc agg agg cga ctg agt g tg gag att tat gac aag     1066
Glu Phe Lys Glu Thr Arg Arg Arg Leu Ser V al Glu Ile Tyr Asp Lys
    325                 330                 335 ttc cag cgg gcc acc tcc atc aag cgg aag c tc tcg gca gaa ctg gct     1114
Phe Gln Arg Ala Thr Ser Ile Lys Arg Lys L eu Ser Ala Glu Leu Ala
340                 345                 350                 355
```

-continued

```
gga aac cac aat cag gag ctg act cct tgt a gg agg acc ctg tca gtg      1162
Gly Asn His Asn Gln Glu Leu Thr Pro Cys A rg Arg Thr Leu Ser Val
                360                     365                 370 aac cac ctg acc agc gag agg gat gtc ttg c ct ccc tta ctg aag act      1210
Asn His Leu Thr Ser Glu Arg Asp Val Leu P ro Pro Leu Leu Lys Thr
            375                 380                 385 gag agt atc tat ctg aat ggt ttg acg cca c ac tgt gct ggt gaa gag      1258
Glu Ser Ile Tyr Leu Asn Gly Leu Thr Pro H is Cys Ala Gly Glu Glu
        390                 395                 400 att gct gtg att gag aac atc aaa tag ccctctct tt aaataacctt            1305
Ile Ala Val Ile Glu Asn Ile Lys
    405                 410 aggcatagcc ataggtgagg acttctctat gctctttatg actgttgctg g tagcatttt    1365
ttaaattgtg catgagctca aagggggaac aaaatagata cacccatcat g gtcatctat   1425
catcaagaga atttggaatt ctgagccagc actttctttc tgatgatgct t gttgaacgg   1485
tccactttct tgatgagtg gaatgacaag caatgtctga tgccttttg t gcccagact     1545
gttttcctct ctctttccct aatgtgccat aaggcctcag aatgaatgag a attgtttct   1605
ggtaacaatg tagctttgag ggatcagttc ttaacttttc agggtctacc t aactgagcc   1665
tagatatgga ccatttatgg atgacaacaa ttttttttt gtaaatgaca a gaaattctt    1725
atgcagcctt ttacctaaga aattttctgt cagtgcctta tcttatgaag a aacagaacc   1785
tctctagcta atgtgtggtt tctccttccc tgccccacc cctaggctca c ctctgcagt    1845
cttttacccc agttctccca tttgaatacc ataccttgct ggaaacagtg t gtaaaatga   1905
ctgaagtgat gatgcccgaa gatgaaatag atgccaaatt agatggacat t gaagcaaca   1965
ctcagcgttg cctagcgtta aaggcactgc agagaaatga ggtgcagagg t ggcccctct   2025
gagtatttat ttgactcagg taccagtggt acatatatac agtgtaatta t gaccaggct   2085
ggtaaaattg gctgctcgca acaatcccc ttttttcctg gcagtatttg g aatttatca    2145
tttattaata actatacatt tttaaaggca gaagaagaaa atctatctat c atctatcta   2205
tctatctatc tatctatcta tctatctatc tatctatcta tctatctaaa t gacctgaca   2265
gaagaaaact gttaaaaatg gatattattg gaggggattt aaaacagtgg g tgtgaatta   2325
tcattctgat ggaaagaaaa tagcaaaaca atgtgttaca agtatttgct a ataaacagt   2385
atactgccag cttctaattg cttttttgatg tatgaaaggc ttatataatt t tcttttcgt   2445
tgggtgactt ttgccagatg agaggaggtg gcacagtggt gagtgcaggg c acagtccta   2505
gccttctgtg ggtatacttt tggagttgtg acttggctgt gagggcagaa g ttgaagttg   2565
ggatcactgt gactttgcac atggaaaaat gcagattgca ggcataattc a tctctgaca   2625
ttagagaaaa agctgttata gcacaattta aattttgaga gtttgctgtg t tttttttc    2685
acataaaaga ggctgattat tcttttagt ttaattttat atcctgtaat t ctttggatg    2745
gttccaagat tcagaaaaaa ttcagtaaat gcacccgta aattgctacc c tttccttta    2805
ttttcatact tagatctgct gtacattgta tatatatata attttaaaa t gcagaaaga   2865
aaataatttc cctaaatata attgcaaact gatttctttt acttttttgt g tctgggggt   2925
gggagctgta tctgaataag tggcattcag attagggtct tgaaaaataa a cccagaatc   2985
tttaaaagaa gcaaataaac taatagacgc ttatttttcca aaatttaaat t taagctaga   3045
aatgtaaata ttcaattaat ttgttaaaag tacttttata aagttaaaaa a aatccaacc   3105
aaaattttag aaagtcaggc tcttttagaa agaaagctac acccatttcc t caaataact   3165
```

-continued

```
gttccgaaaa tttatatggt ggaatgcgcc atgtataaac tgtgaattgt a ttgacaaat    3225 aaagtttgta attaaagtca aaaaaaaaaa aaaaaaaaaa aaaaaaaaaa a aaaaaaaa    3285 aaaaaaaaaa aaaaa                                                      3300
```

<210> SEQ ID NO 83
<211> LENGTH: 411
<212> TYPE: PRT
<213> ORGANISM: H. sapiens

<400> SEQUENCE: 83

```
Met Ala Ala Pro Asp Leu Leu Asp Pro Lys Ser Ala Ala Gln Asn Ser
 1               5                  10                  15

Lys Pro Arg Leu Ser Phe Ser Thr Lys Pro Thr Val Leu Ala Ser Arg
            20                  25                  30

Val Glu Ser Asp Thr Thr Ile Asn Val Met Lys Trp Lys Thr Val Ser
        35                  40                  45

Thr Ile Phe Leu Val Val Leu Tyr Leu Ile Ile Gly Ala Thr Val
    50                  55                  60

Phe Lys Ala Leu Glu Gln Pro His Glu Ile Ser Gln Arg Thr Thr Ile
65                  70                  75                  80

Val Ile Gln Lys Gln Thr Phe Ile Ser Gln His Ser Cys Val Asn Ser
                85                  90                  95

Thr Glu Leu Asp Glu Leu Ile Gln Gln Ile Val Ala Ala Ile Asn Ala
           100                 105                 110

Gly Ile Ile Pro Leu Gly Asn Thr Ser Asn Gln Ile Ser His Trp Asp
       115                 120                 125

Leu Gly Ser Ser Phe Phe Ala Gly Thr Val Ile Thr Thr Ile Gly
130                 135                 140

Phe Gly Asn Ile Ser Pro Arg Thr Glu Gly Gly Lys Ile Phe Cys Ile
145                 150                 155                 160

Ile Tyr Ala Leu Leu Gly Ile Pro Leu Phe Gly Phe Leu Leu Ala Gly
                165                 170                 175

Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205

Ile Ser Thr Ile Ile Phe Ile Leu Phe Gly Cys Val Leu Phe Val Ala
    210                 215                 220

Leu Pro Ala Ile Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
                245                 250                 255

Tyr Val Ala Gly Gly Ser Asp Ile Glu Tyr Leu Asp Phe Tyr Lys Pro
            260                 265                 270

Val Val Trp Phe Trp Ile Leu Val Gly Leu Ala Tyr Phe Ala Ala Val
        275                 280                 285

Leu Ser Met Ile Gly Asp Trp Leu Arg Val Ile Ser Lys Lys Thr Lys
    290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Arg Leu Ser Val Glu Ile
                325                 330                 335

Tyr Asp Lys Phe Gln Arg Ala Thr Ser Ile Lys Arg Lys Leu Ser Ala
            340                 345                 350
```

```
Glu Leu Ala Gly Asn His Asn Gln Glu Leu Thr Pro Cys Arg Arg Thr
        355                 360                 365

Leu Ser Val Asn His Leu Thr Ser Glu Arg Asp Val Leu Pro Pro Leu
    370                 375                 380

Leu Lys Thr Glu Ser Ile Tyr Leu Asn Gly Leu Thr Pro His Cys Ala
385                 390                 395                 400

Gly Glu Glu Ile Ala Val Ile Glu Asn Ile Lys
                405                 410

<210> SEQ ID NO 84
<211> LENGTH: 20
<212> TYPE: DNA
<213> ORGANISM: H. sapiens

<400> SEQUENCE: 84
catagccata ggtgaggact                                                20

<210> SEQ ID NO 85
<211> LENGTH: 20
<212> TYPE: DNA
<213> ORGANISM: H. sapiens

<400> SEQUENCE: 85
gagaggaaaa cagtctgggc                                                20

<210> SEQ ID NO 86
<211> LENGTH: 20
<212> TYPE: DNA
<213> ORGANISM: H. sapiens

<400> SEQUENCE: 86
ggacatcgaa ctaagacctg                                                20

<210> SEQ ID NO 87
<211> LENGTH: 20
<212> TYPE: DNA
<213> ORGANISM: H. sapiens

<400> SEQUENCE: 87
tcccatgcca ttcagatctg                                                20
```

NUCLEIC ACID ENCODING HUMAN POTASSIUM CHANNEL K+ NOV1 PROTEIN

CROSS REFERENCE TO RELATED APPLICATIONS

This application claims the benefit of prior U.S. Provisional Application Serial No. 60/095,836 filed Aug. 7, 1998 and prior U.S. Provisional Application Serial No. 60/116,448 filed Jan. 19, 1999, and prior International Application No. PCT/US99/03826 filed Feb. 22, 1999, which applications are incorporated herein by reference.

BACKGROUND

Ion channels are multi-subunit, membrane bound proteins critical for maintenance of cellular homeostasis in nearly all cell types. Channels are involved in a myriad of processes including modulation of action potentials, regulation of cardiac myocyte excitability, heart rate, vascular tone, neuronal signaling, activation and proliferation of T-cells, and insulin secretion from pancreatic islet cells. In humans, ion channels comprise extended gene families with hundreds, or perhaps thousands, of both closely related and highly divergent family members. The majority of known channels regulate the passage of sodium ($Na^+$), chloride ($Cl^-$), calcium ($Ca^{++}$) and potassium ($K^+$) ions across the cellular membrane.

Given their importance in maintaining normal cellular physiology, it is not surprising that ion channels have been shown to play a role in heritable human disease. Indeed, ion channel defects are involved in predisposition to epilepsy, cardiac arrhythmia (long QT syndrome), hypertension (Bartter's syndrome), cystic fibrosis, (defects in the CFTR chloride channel), several skeletal muscle disorders (hyperkalemic periodic paralysis, paramyotonia congenita, episodic ataxia) and congenital neural deafness (Jervell-Lange-Nielson syndrome), amongst others.

The potassium channel gene family is believed to be the largest and most diverse ion channel family. $K^+$ channels have critical roles in multiple cell types and pathways, and are the focus of significant investigation. Four human conditions, episodic ataxia with myokymia, long QT syndrome, epilepsy and Bartter's syndrome have been shown to be caused by defective $K^+$ ion channels. As the $K^+$ channel family is very diverse, and given that these proteins are critical components of virtually all cells, it is likely that abnormal $K^+$ channels will be involved in the etiology of additional renal, cardiovascular and central nervous system disorders of interest to the medical and pharmaceutical community.

The $K^+$ channel superfamily can be broadly classified into groups, based upon the number of transmembrane domain (TMD) segments in the mature protein. The mink (IsK) gene contains a single TMD and although not a channel by itself, minK associates with different $K^+$ channel subunits, such as KvLQT1 and HERG to modify the activity of these channels. The inward rectifying K+ channels (GIRK, IRK, CIR, ROMK) contain 2 TMD domains and a highly conserved pore domain. Twik-1 is a member of the newly emerging 4TMD $K^+$ channel subset. Twik-like channels (leak channels) are involved in maintaining the steady-state $K^+$ potentials across membranes and therefore the resting potential of the cell near the equilibrium potential for potassium (Duprat et al. (1997) *EMBO J* 16(17):5464–5471). These proteins are particularly intriguing targets for therapeutic regulation. The 6TMD, or Shaker-like channels, presently comprise the largest subset of known $K^+$ channels. The slopoke (sIo) related channels, or $Ca^{++}$ regulated channels apparently have either 10 TMD, or 6 TMD with 4 additional hydrophobic domains.

Four transmembrane domain, tandem pore domain K+ channels (4T/2P channels) represent a new family of potassium selective ion channels involved in the control of background membrane conductances. In mammals, five channels fitting the 4T/2P architecture have been described: TWIK, TREK, TASK-1, TASK-2 and TRAAK. The 4T/2P channels all have distinct characteristics, but are all thought to be involved in maintaining the steady-state $K^+$ potentials across membranes and therefore the resting potential of the cell near the equilibrium potential for potassium (Duprat et al. (1997) *EMBO J* 16(17):5464–5471). These proteins are particularly intriguing targets for therapeutic regulation. Within this group, TWIK-1, TREK-1 and TASK-1 and TASK-2 are widely distributed in many different tissues, while TRAAK is present exclusively in brain, spinal cord and retina. The 4T/2P channels have different physiologic properties; TREK-1 channels, are outwardly rectifying (Fink et al. (1996) *EMBO J* 15(24):6854–62), while TWIK-1 channels, are inwardly rectifying (Lesage et al. (1996) *EMBO J* 15(5):1004–11. TASK channels are regulated by changes in PH while TRAAK channels are stimulated by arachidonic acid (Reyes et al. (1998) *JBC* 273(47):30863–30869).

The degree of sequence homology between different $K^+$ channel genes is substantial. At the amino acid level, there is about 40% similarity between different human genes, with distinct regions having higher homology, specifically the pore domain. It has been estimated that the K+ channel gene family contains approximately $10^2$–$10^3$ individual genes. Despite the large number of potential genes, an analysis of public sequence databases and the scientific literature demonstrates that only a small number, approximately 20–30, have been identified. This analysis suggests that many of these important genes remain to be identified.

Potassium channels are involved in multiple different processes and are important regulators of homeostasis in nearly all cell types. Their relevance to basic cellular physiology and role in many human diseases suggests that pharmacological agents could be designed to specific channel subtypes and these compounds then applied to a large market (Bulman, D. E. (1997) *Hum Mol Genet* 6:1679–1685; Ackerman, M. J. and Clapham D. E. (1997) *NEJM* 336:1575–1586, Curran, M. E. (1998) *Current Opinion in Biotechnology* 9:565–572). The variety of therapeutic agents that modulate K+ channel activity reflects the diversity of physiological roles and importance of K+ channels in cellular function. A difficulty encountered in therapeutic use of therapeutic agents that modify K+ channel activity is that the presently available compounds tend to be non-specific and elicit both positive and negative responses, thereby reducing clinical efficacy. To facilitate development of specific compounds it is desirable to have further characterize novel K+ channels for use in in vitro and in vivo assays.

Relevant Literature

A large body of literature exists in the general area of potassium channels. A review of the literature may be found in the series of books, "The Ion Channel Factsbook", volumes 1–4, by Edward C. Conley and William J. Brammar, Academic Press. An overview is provided of: extracellular ligand-gated ion channels (ISBN: 0121844501), intracellular ligand-gated channels (ISBN: 012184451X), Inward rectifier and intercellular channels (ISBN: 0121844528), and voltage gated channels (ISBN: 0121844536). Hille, B. (1992) "Ionic Channels of Excitable Membranes", 2$^{nd}$ Ed. Sunderland MA:Sinauer Associates, also reviews potassium channels.

Jan and Jan (1997) *Annu. Rev. Neurosci.* 20:91–123 review cloned potassium channels from eukaryotes and prokaryotes. Ackerman and Clapham (1997) *N. Engl. J. Med.* 336:1575–1586 discuss the basic science of ion channels in connection with clinical disease. Bulman (1997) *Hum. Mol. Genet.* 6:1679–1685 describe some phenotypic variation in ion channel disorders.

Stephan et al. (1994) *Neurology* 44:1915–1920 describe a pedigree segregating a myotonia with muscular hypertrophy and hyperirritability as an autosomal dominant trait (rippling muscle disease, Ricker et al. (1989) *Arch. Neurol.* 46405–408). Electromyography demonstrated that mechanical stimulation provoked electrically silent contractions. The responsible gene was localized to the distal end of the long arm of chromosome 1, in a 12-cM region near D1S235.

Type II pseudohypoaldosteronism is the designation used for a syndrome of chronic mineralocorticoid-resistant hyperkalemia with hypertension. The primary abnormality in type II PHA is thought to be a specific defect of the renal secretory mechanism for potassium, which limits the kaliuretic response to, but not the sodium and chloride reabsorptive effect of, mineralocorticoid. By analysis of linkage in families with autosomal dominant transmission, Mansfield et al. (1997) *Nature Genet.* 16:202–205 demonstrated locus heterogeneity of the trait, with linkage of the PHA2 gene to 1q31-q42 and 17p1 1-q21.

Sequences of four transmembrane, two pore potassium channels have been previously described. Reyes et al. (1998) *J Biol Chem* 273(47):30863–30869 discloses a pH sensitive channel. As with the related TASK-1 and TRAAK channels, the outward rectification is lost at high external K+ concentration. The TRAAK channel is described by Fink et al. (1998) *EMBO J* 17(12):3297–308. A cardiac two-pore channel is described in Kim et al. (1998) *Circ Res* 82(4):513–8. An open rectifier potassium channel with two pore domains in tandem and having a postsynaptic density protein binding sequence at the C terminal was cloned by Leonoudakis et al. (1998) *J Neurosci* 18(3):868–77.

The electrophysiological properties of Task channels are of interest, (Duprat et al. (1997) *EMBO J* 16:5464–71). TASK currents are K+-selective, instantaneous and non-inactivating. They show an outward rectification when external [K+] is low, which is not observed for high [K+]out, suggesting a lack of intrinsic voltage sensitivity The absence of activation and inactivation kinetics as well as voltage independence are characteristic of conductances referred to as leak or background conductances. TASK is very sensitive to variations of extracellular pH in a narrow physiological range, a property probably essential for its physiological function, and suggests that small pH variations may serve a communication role in the nervous system.

SUMMARY OF THE INVENTION

Isolated nucleotide compositions and sequences are provided for K+Hnov genes. The K+Hnov nucleic acid compositions find use in identifying homologous or related genes; in producing compositions that modulate the expression or function of its encoded proteins; for gene therapy; mapping functional regions of the proteins; and in studying associated physiological pathways. In addition, modulation of the gene activity in vivo is used for prophylactic and therapeutic purposes, such as treatment of potassium channel defects, identification of cell type based on expression, and the like.

DESCRIPTION OF THE SPECIFIC EMBODIMENTS

Nucleic acid compositions encoding K+Hnov polypeptides are provided. They are used in identifying homologous or related genes; in producing compositions that modulate the expression or function of the encoded proteins; for gene therapy; mapping functional regions of the proteins; and in studying associated physiological pathways. The K+Hnov gene products are members of the potassium channel gene family, and have high degrees of homology to known potassium channels. The encoded polypeptides may be alpha subunits, which form the functional channel, or accessory subunits that act to modulate the channel activity.

Characterization of K+Hnov

The sequence data predict that the provided K+Hnov genes encode potassium channels. Table 1 summarizes the DNA sequences, corresponding SEQ ID NOs, chromosomal locations, and polymorphisms. The provided sequences may encode a predicted K$^+$channel, e.g. voltage gated, inward rectifier, etc. or a modulatory subunit.

Electrophysiologic characterization of ion channels is an important part of understanding channel function. Full length ion channel cDNAs may be combined with proper vectors to form expression constructs of each individual channel. Functional analyses of expressed channels can be performed in heterologous systems, or by expression in mammalian cell lines. For expression analyses in heterologous systems such as Xenopus oocytes, synthetic mRNA is made through in vitro transcription of each channel construct. mRNA is then injected, singly or in combination with interacting channel subunit mRNAs, into prepared oocytes and the cells allowed to express the channel for several days. Oocytes expressing the channel of interest are then analyzed by whole cell voltage clamp and patch clamp techniques.

To determine the properties of each channel when expressed in mammalian cells expression vectors specific to this type of analyses may be constructed and the resultant construct used to transform the target cells (for example human embryonic kidney (HEK) cells). Both stable and transiently expressing lines may be studied using whole cell voltage clamp and patch clamp techniques. Data obtained from EP studies includes, but is not limited to: current profiles elicited by depolarization and hyperpolarization, current-voltage (I–V) relationships, voltage dependence of activation, biophysical kinetics of channel activation, deactivation, and inactivation, reversal potential, ion selectivity, gating properties and sensitivity to channel antagonists and agonists.

Heterologous or mammalian cell lines expressing the novel channels can be used to characterize small molecules and drugs which interact with the channel. The same experiments can be used to assay for novel compounds which interact with the expressed channels.

In many cases the functional ion channel formed by K+Hnov polypeptides will be heteromultimers. Heteromultimers are known to form between different voltage gated, outward rectifying potassium channel a subunits, generally comprising four subunits, and frequently associated with auxiliary, β subunits. Typically such α subunits share a six-transmembrane domain structure (S1–S6), with one. highly positively charged domain (S4) and a pore region situated between S5 and S6. Examples of such subunits are K+Hnov4, K+Hnov9, and K+Hnov12. Channels are also formed by multimerization of subunits of the two transmembrane and one pore architecture. It is predicted that two subunits of K+Hnov49 or K+Hnov59 will be required to form a functional channel.

Heteromultimers of greatest interest are those that form between subunits expressed in the same tissues, and are a combination of subunits from the same species. In addition, the formation of multimers between the subject polypeptides and subunits that form functional channels are of particular interest. The resulting channel may have decreased or increased conductance relative to a homomultimer, and may be altered in response to beta subunits or other modulatory molecules.

Known voltage gated K+ channel α subunits include Kv1.1–1.8 (Gutman et al. (1993) Sem. Neurosci. 5:101–106); Kv2.1–2.2; Kv3.1–3.4; Kv4.14.3; Kv5.1; Kv6.1; Kv7.1; Kv8.1; Kv9.1–9.2. The subunits capable of forming ion inducing channels include all of those in the kv1 through Kv4; and Kv7 families. The Kv5.1, Kv6.1, Kv8.1 and Kv9.1–9.2 subunits may be electrically silent, but functional in modifying the properties in heteromultimers.

sequence elements are exons and 3' and 5' non-coding regions. Normally mRNA species have contiguous exons, with the intervening introns, when present, removed by nuclear RNA splicing, to create a continuous open reading frame encoding a K+Hnov protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated

TABLE 1

| Name | cDNA SEQ | Protein SEQ | Polymorphisms | Chromosome Position | Channel Type |
|---|---|---|---|---|---|
| K + Hnov1 | SEQ ID NO:1 | SEQ ID NO:2 | Alternative poly(A) tail: 1236, 2395 | 2q37 | ATP-sensitive inward rectifying |
| K + Hnov4 | SEQ ID NO:3 | SEQ ID NO:4 | A312C T335C A377G T344C A401G CA410-411GG (Ala/Thr) | unknown | Voltage gated K+ channel |
| K + Hnov6 | SEQ ID NO:5 | SEQ ID NO:6 | | 2p23 | Delayed rectifying K+ channel |
| K + Hnov9 | SEQ ID NO:7 | SEQ ID NO:8 | Alternative poly(A) tail: 2304 | 8q23 | Voltage gated K+ channel |
| K + Hnov12 | SEQ ID NO:9 | SEQ ID NO:10 | C321T (Pro/Leu) A375G (Glu/Gly) C407T (Leu/Phe) | Xp21 | Voltage gated K+ channel |
| K + Hnov15 | SEQ ID NO:11 | SEQ ID NO:12 | Alternative poly(A) tail: 1427 A689G (Gly/Arg) | 13q14 | modulatory subunit |
| K + Hnov27 | SEQ ID NO:13 | SEQ ID NO:14 | T365A (Ile/Asn) | 18q12 | modulatory subunit |
| K + Hnov2 | SEQ ID NO:15 | SEQ ID NO:16 | N/A | N/A | 4 transmembrane domain, 2 pore domain K+ channel |
| K + Hnov 11 | SEQ ID NO:17 | SEQ ID NO:18 | N/A | N/A | Human ortholog of murine gene, 6 transmembrane dominas, voltage gated, delayed rectifier K+ channel |
| K + Hnov 14 | SEQ ID NO:19 | SEQ ID NO:20 | C3168T | 12q14 | 6 transmembrane domain, voltage gated K+ channel |
| K + Hnov28 | SEQ ID NO:21–24 | SEQ ID NO:25 | 4 alternative 5' splices | 3q29 | Modulatory subunit |
| K + Hnov42 | SEQ ID NO:26 | SEQ ID NO:27 | G1162A; T1460A; T2496A | 8q11 | Homology to K+ channel protein of C. elegans |
| K + Hnov44 | SEQ ID NO:28–29 | SEQ ID NO:30 | N/A | 22p13 | beta-subunit. |
| K + Hnov49 | SEQ ID NO:80 | SEQ ID NO:81 | (ATCT)$_n$ repeats in the 3' UTR sequence, starting at position 2186 | 1q41 | 4T/2P channel; linked to the disease loci for rippling muscle disease 1 (RMD1), and type II pseudohypoaldosteronism |
| K + Hnov59 | SEQ ID NO:82 | SEQ ID NO:83 | N/A | chr19 | 4T/2P channel |

K+Hnov Nucleic Acid Compositions

As used herein, the term "K+Hnov" is generically used to refer to any one of the provided genetic sequences listed in Table 1. Where a specific K+Hnov sequence is intended, the numerical designation, e.g. K49 or K59, will be added. Nucleic acids encoding K+Hnov potassium channels may be cDNA or genomic DNA or a fragment thereof. The term "K+Hnov gene" shall be intended to mean the open reading frame encoding any of the provided K+Hnov polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where K+Hnov genes are expressed. The tissue specific expression is useful for determining the pattern of expression, and for providing promoters that mimic the native pattern of expression. Naturally occurring polymorphisms in the promoter regions are useful for determining natural variations in expression, particularly those that may be associated with disease.

Alternatively, mutations may be introduced into the promoter regions to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of K+Hnov expression, especially in different tissues or stages of development, and to identify cis acting sequences and trans acting factors that regulate or mediate K+Hnov expression. Such transcription or translational control regions may be operably linked to a K+Hnov gene in order to promote expression of wild type or altered K+Hnov or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The K+Hnov genes are isolated and obtained in substantial purity, generally as other than an intact chromosome. Usually, the DNA will be obtained substantially free of other nucleic acid sequences that do not include a K+Hnov sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of K+Hnov gene expression in the sample.

The sequence of a K+Hnov gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111 23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:3541 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:1204 (1989). Such mutated genes may be used to study structure-function relationships of K+Hnov, or to alter properties of the protein that affect its function or regulation.

Homologs and orthologs of K+Hnov genes are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided K+Hnov sequences, e.g. allelic variants, genetically altered versions of the gene, etc., bind to the provided K+Hnov sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between mammalian species, e.g. human and mouse, homologs have substantial sequence similarity, i.e. at least 75% sequence identity between nucleotide sequences, in some cases 80 or 90% sequence identity, and may be as high as 95% sequence identity between closely related species. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), J. Mol. Biol. 215:403–10. In general, variants of the invention have a sequence identity greater than at least about 65%, preferably at least about 75%, more preferably at least about 85%, and may be greater than at least about 90% or more as determined by the Smith-Waterman homology search algorithm as implemented in MPSRCH program (Oxford Molecular). Exemplary search parameters for use with the MPSRCH program in order to identify sequences of a desired sequence identity are as follows: gap open penalty: 12; and gap extension penalty: 1.

K+Hnov Polypeptides

The subject nucleic acid sequences may be employed for producing all or portions of K+Hnov polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a K+Hnov gene, or may be derived from exogenous sources.

The peptide may be expressed in prokaryotes or eukaryotes in accordance with conventional ways, depending upon the purpose for expression. For large scale production of the protein, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to express the K+Hnov gene in eukaryotic cells, where the K+Hnov protein will benefit from native folding and post-translational modifications. Small peptides can also be synthesized in the laboratory. Peptides that are subsets of the complete K+Hnov sequence may be used to identify and investigate parts of the protein important for function, or to raise antibodies directed against these regions.

Fragments of interest include the transmembrane and pore domains, the signal sequences, regions of interaction between subunits, etc. Such domains will usually include at least about 20 amino acids of the provided sequence, more usually at least about 50 amino acids, and may include 100 amino acids or more, up to the complete domain. Binding contacts may be comprised of non-contiguous sequences, which are brought into proximity by the tertiary structure of the protein. The sequence of such fragments may be modified through manipulation of the coding sequence, as described above. Truncations may be performed at the carboxy or amino terminus of the fragment, e.g. to determine the minimum sequence required for biological activity.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed K+Hnov polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of K+Hnov. Antibodies may be raised to isolated peptides corresponding to specific domains, e.g. the pore domain and the transmembrane domain, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

K+Hnov Genotyping

The subject nucleic acid and/or polypeptide compositions may be used to genotyping and other analysis for the presence of polymorphisms in the sequence, or variation in the expression of the subject genes. Genotyping may be performed to determine whether a particular polymorphisms is associated with a disease state or genetic predisposition to a disease state, particularly diseases associated with defects in excitatory properties of cells, e.g. cardiac, muscle, renal and neural cells. Disease of interest include rippling muscle disease, and type II psuedohypoaldosteronism.

Clinical disorders associated with K+ channel defects include long-QT syndrome; a congenital disorder affecting 1 in 10,000–15,000. Affected individuals have a prolonged QT interval in the electrocardiogram due to a delayed repolarization of the ventricle. Genetic linkage analyses identified two loci for long QT syndrome, LQT1, in 11p15.5 and LQT2, in 7q35–36. Positional cloning techniques identified the novel K+ channel KvLQT1 on chromosome 11 while candidate gene analysis identified causative mutations in the HERG K+ channel for LQT2.

The weaver mouse exhibits several abnormal neurological symptoms, including severe ataxia, loss of granule cell neurons in the cerebellum and dopaminergic cells in the substantia nigra, as well as seizures and male infertility. A G-protein-coupled K+ channel having a mutation in the conserved pore domain has been determined to cause the disease. The pancreatic-islet β-cell ATP-sensitive K+ channel (KATP) is composed of two subunits, the sulfonylurea receptor (SUR) and the inward rectifier K+ channel Kir6.2. Mutations in both SUR and Kir6.2 have been identified in patients with persistent hyperinsulinemic hypoglycemia of infancy, which is caused by unregulated secretion of insulin.

Genotyping may also be performed for pharmacogenetic analysis to assess the association between an individual's genotype and that individual's ability to react to a therapeutic agent. Differences in target sensitivity can lead to toxicity or therapeutic failure. Relationships between polymorphisms in channel expression or specificity can be used to optimize therapeutic dose administration.

Genetic polymorphisms are identified in the K+Hnov gene (examples are listed in table 1), e.g. the repeat variation in the 3' UTR of K49. Nucleic acids comprising the polymorphic sequences are used to screen patients for altered reactivity and adverse side effects in response to drugs that act on K+ channels.

K+Hnov genotyping is performed by DNA or RNA sequence and/or hybridization analysis of any convenient sample from a patient, e.g. biopsy material, blood sample, scrapings from cheek, etc. A nucleic acid sample from an individual is analyzed for the presence of polymorphisms in K+Hnov, particularly those that affect the activity, responsiveness or expression of K+Hnov. Specific sequences of interest include any polymorphism that leads to changes in basal expression in one or more tissues, to changes in the modulation of K+Hnov expression, or alterations in K+Hnov specificity and/or activity.

The effect of a polymorphism in K+Hnov gene sequence on the response to a particular agent may be determined by in vitro or in vivo assays. Such assays may include monitoring during clinical trials, testing on genetically defined cell lines, etc. The response of an individual to the agent can then be predicted by determining the K+Hnov genotype with respect to the polymorphism. Where there is a differential distribution of a polymorphism by racial background, guidelines for drug administration can be generally tailored to a particular ethnic group.

Biochemical studies may be performed to determine whether a sequence polymorphism in a K+Hnov coding region or control regions is associated with disease, for example the association of K+Hnov 9 with idiopathic generalized epilepsy. Disease associated polymorphisms may include deletion or truncation of the gene, mutations that alter expression level, that affect the electrical activity of the channel, etc.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of current techniques may be found in Sambrook et al. Molecular Cloning: A Laboratory Manual, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *N.A.R.* 18:2887–2890; and Delahunty et al. (1996) *Am. J. Hum. Genet.*58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. 32P, 35S, 3H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided sequences, e.g. oligonucleotides of at least 12 nt, frequently 20 nt, or larger, and including the sequence flanking a polymorphic position in a $K^+$Hnov sequence; coding sequences for different $K^+$Hnov channels, panels of ion channels comprising one or more of the provided $K^+$ channels; etc. Such an array may comprise a series of oligonucleotides, each of which can specifically hybridize to a different polymorphism. For examples of arrays, see Hacia et al. (1996) *Nature Genetics* 14:441 447; Lockhart et al. (1996) *Nature Biotechnol.* 14:1675–1680; and De Risi et al. (1996) *Nature Genetics* 14:457–460.

Screening for polymorphisms in K+Hnov may be based on the functional or antigenic characteristics of the protein. Protein truncation assays are useful in detecting deletions that may affect the biological activity of the protein. Various immunoassays designed to detect polymorphisms in K+Hnov proteins may be used in screening. Where many diverse genetic mutations lead to a particular disease phenotype, functional protein assays have proven to be effective screening tools. The activity of the encoded K+Hnov protein as a potassium channel may be determined by comparison with the wild-type protein.

Antibodies specific for a K+Hnov may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal K+Hnov polypeptides in patient cells. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Modulation of Gene Expression

The K+Hnov genes, gene fragments, or the encoded protein or protein fragments are useful in gene therapy to treat disorders associated with K+Hnov defects. Expression vectors may be used to introduce the K+Hnov gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or K+Hnov protein may be introduced into tissues or host cells by any number of routes, including viral infection, microinjection, or fusion of vesicles. Jet injection may also be used for intramuscular administration, as described by Furth et al. (1992) *Anal Biochem* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the K+Hnov or DNA, then bombarded into skin cells.

Antisense molecules can be used to down-regulate expression of K+Hnov in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5-'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the. natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Genetically Altered Cell or Animal Models for K+ Hnov Function

The subject nucleic acids can be used to generate transgenic animals or site specific gene modifications in cell lines. Transgenic animals may be made through homologous recombination, where the normal K+Hnov locus is altered. Alternatively, a nucleic acid construct is randomly integrated into the genome. Vectors for stable integration include plasmids, retroviruses and other animal viruses, YACs, and the like.

The modified cells or animals are useful in the study of K+Hnov function and regulation. For example, a series of small deletions and/or substitutions may be made in the K+Hnov gene to determine the role of different transmembrane domains in forming multimeric structures, ion channels, etc. Of interest are the use of K+Hnov to construct transgenic animal models for epilepsy and other neurological defects, where expression of K+Hnov is specifically reduced or absent. Specific constructs of interest include anti-sense K+Hnov, which will block K+Hnov expression, expression of dominant negative K+Hnov mutations, etc. One may also provide for expression of the K+Hnov gene or variants thereof in cells or tissues where it is not normally expressed or at abnormal times of development.

DNA constructs for homologous recombination will comprise at least a portion of the K+Hnov gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymologqy* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old super-ovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on Ras or related gene activation, oncogenesis, etc.

Testing of K+Hnov Function and Responses

Potassium channels such as K+Hnov polypeptides are involved in multiple biologically important processes. Pharmacological agents designed to affect only specific channel subtypes are of particular interest. Presently available compounds tend to be non-specific and elicit both positive and negative responses, thereby reducing clinical efficacy.

The subject polypeptides may be used in in vitro and in vivo models to test the specificity of novel compounds, and of analogs and derivatives of compounds known to act on potassium channels. Numerous pharmacological agents have profound affects on K+ channel activity. As examples, Sotalol (BETAPACE) is a class III antiarrhythmic drug that prolongs cardiac action potentials by inhibiting delayed rectifier K+ channels. Sulfonylurea drugs, such as Glipizide (GLUCOTROL) and Tolazamide (TOLAMIDE) function as antidiabetic drugs by blocking ATP-sensitive K+ channels present in pancreatic islet cells, thereby regulating insulin secretion. Diazoxide (HYPERSTAT IV) is an antihypertensive drug that activates ATP-sensitive K+ channels, resulting in the relaxation of vascular smooth muscle. There are several other examples of drugs that have antidiabetic, antihypertensive, or antiarrhythmic activities. A number of drugs that activate K+ channels that have been proposed as coronary vasodilators for the treatment of both vasospastic and chronic stable angina. The availability of multiple K+ channel subunits allows in vitro reconstruction of functional channels, which may comprise different alpha and beta subunits. The individual components may be modified by sequence deletion, substitution, etc. to determine the functional role of specific domains.

Drug screening may be performed using an in vitro model, a genetically altered cell or animal, or purified K+Hnov protein, either as monomers, homomultimers or hetermultimers. One can identify ligands or substrates that bind to, modulate or mimic the action of K+Hnov. Drug screening identifies agents that provide a replacement for K+Hnov function in abnormal cells. Of particular interest are screening assays for agents that have a low toxicity for human cells. A wide variety of assays may be used for this purpose, including monitoring cellular excitation and conductance, labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of K+Hnov polypeptide. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific-binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–100 wt. %. The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats Stabilizing agents, wetting and emulsifying agents, salts for varying the osmotic pressure or buffers for securing an adequate pH value, and skin penetration enhancers can be used as auxiliary agents.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Methods

Two different types of sequence searches were performed. The first centered on the most highly conserved region of the K+ channel family, the pore domain. The pore is composed of 15–17 amino acids and can be divided into subfamilies based on the number of transmembrane segments present in the channel. Eleven variant peptide sequences corresponding to the, pore domain were used in TBLASTN searches against the EST division of Genbank. Significant matches were identified, and classified into 2 categories: identical to known human K+ channels and related to known K+ channels. The pore sequences are shown in Table 2.

TABLE 2

| SEQ ID NO | Genbank # | |
|---|---|---|
| 49 | L02751 | TGGTGGGCTGTGGTGACCATGACMCTGTGGGCTATGGGGACATG |
| 50 | M60451 | TGGTGGGCAGTGGTCACCATGACCACTGTGGGCTACGGGGACATG |
| 51 | L02752 | TGGTGGGCAGTCGTCTCCATGACAACTGTAGGCTATGGAGACATG |
| 52 | M55515 | TGGTGGGCAGTGGTAACCATGACAACAGTGGGTTACGGCGATATG |
| 53 | Z11585 | TGGTGGGCTGTGGTCACCATGACGACCCTGGGCTATGGAGACATG |
| 54 | U40990 | TGGTGGGGGTGGTCACAGTCACCACCATCGGCTATGGGGACMG |
| 55 | 126643 | TGGTGGGCAGTGGTCACCATGACCACGGTGGCTATGGGGACATG |
| 56 | M96747 | TGGTGGGCCGTGGTCACCATGACGACCCTGGGCTATGGAGACATG |
| 57 | M64678 | TGGTGGGCTGTGGTCACCATGACGACACTGGGCTACGGAGACATG |
| 58 | M55514 | TGGTGGGCTGTGGTGACCATGACMCTGTGGGCTATGGGGACATG |
| 59 | X83582 | TTCCTGUCTCCAUGAGACCGAMCMCCAUGGGTATGGCUCCG |
| 60 | S78684 | UTUAUCTCMTAGAGACAGAMCCACCAUGGUATGGCTACCG |
| 61 | U22413 | TTCCTCTTCTCCAUGAGACCCAGACMCCATAGGCTATGGTUCAG |
| 62 | U24056 | UCCTGUCTCGGTGGAGACGCAGACGACCATCGGCTATGGGUCCG |
| 63 | U52155 | UCCTCTTCTCCCTTGMTCCCAAACCACCAUGGCTATGGCUCCG |
| 64 | D87291 | UTCTCTUTCCCTGGMTCCCAGACMCCAUGGCTATGGAGTCCG |
| 65 | D50582 | UCCTTTTCTCCATTGAGGTCCMGTGACTATTGGCUTGGGGGCG |
| 66 | D50315 | TTTCTCUCTCCAUGMGUCAAGUACCAUGGGTUGGAGGGAG |
| 67 | U04270 | GCGCTCTACTTCACCUCAGCAGCCTCACCAGTGTGGGCUCGGCMC |

The unique pore peptides sequences are shown in Table 3

TABLE 3

| SEQ ID NO: | Amino Acid Sequence |
|---|---|
| 68 | WWAVVSMWTTVGYGDM |
| 69 | WWAWTMTTLGYGDM |
| 70 | WWGVVTVTTIGYGDK |
| 71 | WWAWTMTTVGYGDM |
| 72 | FLFSIEVQVTIGFGG |
| 73 | FLFSLESQTTIGYGV |
| 74 | FLFSIETETTIGYGY |
| 75 | FLFSIETQTTIGYGF |
| 76 | FLFSVETQTTIGYGF |
| 77 | FLFSLESQTTIGYGF |
| 78 | FLFSIETETTIGYGF |
| 79 | ALYFTFSSLTSVGFGN |

The second set of experiments was based on a complex, reiterative process. Annotated protein and DNA sequences were obtained from GenBank for all known K+ channels from all species. The TBLASTN and BLASTN programs were used to identify homologous ESTs, which were then analyzed using the BLASTX and BLASTN algorithms to identify ESTS which were related to K+ channels yet not identical to any known human K+ channel gene.

Novel human K+ channels were defined as those that had clear homology to known K+ channels from any species and were not present as identities or near identities to any human-derived sequences in any division of Genbank.

Isolation of full length cDNA sequence. EST clones were picked from the IMAGE consortium cDNA library and end-sequenced with vector primers. Gap closure was achieved either by primer walking or transposon sequencing. GeneTrapper (Life Technologies) was used to isolate larger cDNA clones according to the provided protocol RACE was used to extend the sequences as necessary using standard protocols.

Sequences were assembled in Sequencer (Gene Codes). The presence of open reading frames was assessed as well as potential start codons. Potential polymorphisms were detected as sequence variants between multiple independent clones. Sequence homologies were detected using the BLAST algorithms.

The completed gene sequences and predicted amino acid sequences are provided as SEQ ID NO:1, 3, 5, 7, 9, 11, 13, 15, 17, 19, 21–24, 26 and 28–29. Polymorphisms, chromosome locations and family assignments are shown in Table 1.

ESTs that had top human hits with >95% identity over 100 amino acids were discarded. This was based upon the inventors' experience that these sequences were usually identical to the starting probe sequences, with the differences due to sequence error. The remaining BLASTN and BLASTX outputs for each EST were examined manually, i.e., ESTs were removed from the analysis if the inventors determined that the variation from the known related probe sequence was a result of poor database sequence. Poor database sequence was usually identified as a number of 'N' nucleotides in the database sequence for a BLASTN search and as a base deletion or insertion in the database sequence, resulting in a peptide frameshift, for a BLASTX output. ESTs for which the highest scoring match was to non-related sequences were also discarded at this stage. The EST sequences that correspond to each clone are shown in Table 4.

TABLE 4

| Genbank Accession# | K + Hnov | clone ID | Trace | IMAGE Plate Coordinates | Read 5/40 /3' |
|---|---|---|---|---|---|
| N39619 | K + Hnov2 | 277113 | yy51h05.s1 | 611p10 | 3' |
| N46767 | K + Hnov2 | 277113 | yy51h05.r1 | 611p10 | 5' |
| R19352 | K + Hnov11 | 33144 | yg24f12.r1 | 155o24 | 5' |
| R44628 | K + Hnov11 | 33144 | yg24f12.s1 | 155o24 | 3' |
| R35526 | K + Hnov14 | 37299 | yg64e08.r1 | 165o15 | 5' |
| R73353 | K + Hnov14 | 157854 | yl10e04.r1 | 251g07 | 5' |
| AA397616 | K + Hnov14 | 728558 | zt79c08.r1 | 1787j15 | 5' |
| AA286692 | K + Hnov28 | 700757 | zs48h03.r1 | 1715d6 | 5' |
| AA150494 | K + Hnov42 | 491748 | zl08e07.s1 | 1170o13 | 3' |
| AA156697 | K + Hnov42 | 491748 | zl08e07.r1 | 1170o13 | 5' |
| AA191752 | K + Hnov42 | 626699 | zp82d06.r1 | 1522f12 | 5' |
| AA216446 | K + Hnov42 | 626699 | zp82d06.s1 | 1522f12 | 3' |
| AA430591 | K + Hnov42 | 773611 | zw51f10.r1 | 1904o20 | 5' |
| AA236930 | K + Hnov44 | 683888 | zs01a05.s1 | 1671e9 | 3' |
| AA236968 | K + Hnov44 | 683888 | zs01a05.r1 | 1671e9 | 5' |

Example 2

Chromosomal Localization

Two primers were designed in the 3'-untranslated regions of each gene sequence to amplify a product across the Stanford G3 radiation hybrid map, or the Whitehead GB4 panel. The PCR data were submitted for automatic two-point analysis. Mapping data were correlated with cytoband information and comparisons with the OMIM human gene map data base were made. The following primers were made:

K+Hnov1 on GB4
(SEQ ID NO:31) F: 5' TATCCACATCAATGGACAAGC 3'
(SEQ ID NO:32) R: 5' TGCATAACTGGCTGGGTGTA 3'
Results: 1.71 cR from D2S331, Cytogenetic location of 2q37
K+Hnov2 on G3
F: 5' GTCAGGTGACCGAGTTCA 3'
R: 5' GCTCCATCTCCAGATTCTTC 3'
Results: 0.0 cR from SHGC-1320, Cytogenetic location of 11q12
K+HnoV6 on GB4
(SEQ ID NO:33) F: 5' TGACATCACTGGATGMCTTGA 3'
(SEQ ID NO:34) R: 5' TGCCTGCAAAGTTTGAACAT 3'
Results: 5.23 cR from WI-5509, Cytogenetic location of 2p23
K+Hnov9 on GB4
(SEQ ID NO:35) F: 5' TGACATCACTGGATGAACTTGA 3'
(SEQ ID NO:36) R: 5'TGCCTGCAAGTTTGAACAT 3'
Results 1 21 cR from AFM200VC7 Cytogenetic location of 8q23
K+Hnov 11 on G84
(SEQ ID NO 37) F 5' ACCTGGTGGTATGGAAGCAT 3'
(SEQ ID NO 38) R 5' TTTCTCCTGGCCRCRACCC 3'
Results: 2.43 cR from WI-6756, Cytogenetic location of 8q23
K+Hnov12 on G3
(SEQ ID NO39) F. 5' TCCCTCTTGGGTGACCTTC 3'
(SEQ ID NO:40) R: 5' ATCTTTGTCAGCCACCAGCT 3'
Results: 7.45 cR from SHGC-32925, Cytogenetic location of Xp21
K+Hnov14 on GB4
(SEQ ID NO:41) F: 5' AGGTGTGCTGCCATCTGCTGT-TCG3'
(SEQ ID NO:42) R: 5' AGCCTATCCTCTCTGAGAGT-CAGG
Results: 7.69 cR from WI-7107, Cytogenetic location of 12q14
K+Hnov28 on GB4
(SEQ ID NO:43) F: 5' AAGCAGAGTACTCATGATGCC 3'
(SEQ ID NO:44) R: 5' TCTGGTAGACAGTACAGTGG 3'
Results: 35.38 cR from WI-9695, Cytogenetic location of 3q29
K+Hnov42 on G3
(SEQ ID NO:45) F: 5' CATTTGGCTGGTCCAAGATG 3'
(SEQ ID NO:46) R: 5' AGTCATTGGTAGGGAGGTAC 3'
Results: 7.45 cR from SHGC-32925, Cytogenetic location of Xp21
K+Hnov44 on G3
(SEQ ID NO:47) F: 5° CATGCTTCTACAGTCCAGCC 3'
(SEQ ID NO:48) R: 5' GGTCCTCAGTTGCAGAAATC 3'
Results: 7.45 cR from SHGC-32925, Cytogenetic location of Xp21
Map positions for K+Hnov15 and K+Hnov27 were obtained from public databases. K+Hnov2 and K+Hnov4 have not been mapped.

Example 3

Expression Analysis

RT-PCR was utilized to characterize the expression pattern of the novel ion channels. This approach used RNA from 30 different tissues to generate first strand cDNA. Total RNA was purchased (Clontech, Invitrogen) and used to synthesize first strand cDNA using M-MLV reverse transcriptase and the supplied buffer (Gibco-BRL). The 20 μl reaction contained 5 μg total RNA, 100 ng of random primers, 10 mM DTT.

0 5 mM each dNTP, and an RNAse inhibitor (Gibco-BRL). Identical reactions were set up without reverse transcriptase to control for DNA contamination in the RNA samples The synthesis reaction proceeded for 1 hour at 37° C. followed by 10 minutes at 95° C. These cDNAs, along with control cDNA synthesis reactions without reverse transcriptase, were diluted 1:5 and 2 μl of each sample were arrayed into 96-well trays, dried, and resuspended in PCR buffer prior to PCR amplification. The cDNAs were tested with primers with defined expression patterns to verify the presence of amplifiable cDNA from each tissue. Gene-specific primers were used to amplify the cDNAs in 20 μl PCR reactions with standard conditions, 2.5 mM MgCl$_2$, Taq Gold, and an appropriate annealing temperature.

This approach provides for relatively high-throughput analysis of gene expression in a large set of tissues in a cost-efficient manner and provides qualitative analysis of gene expression only. Modifications can be employed, such as the use of internal control primers, limited cycling parameters, and dilution series to convert this to a quantitative experiment.

Results: Cytogenetic location 1q41, 4.6cR from framework marker D1S217
K+Hnov59 on Whitehead GB4 RH mapping panel
Primer 1 (SEQ ID NO:7): 5'-GGACATCGAACTAAGACCTG-3'
Primer 2 (SEQ ID NO:8): 5'-TCCCATGCCATTCAGATCTG-3'
Results: Cytogenetic location 19q13.2, 8.34cr from framework marker D19S425
Expression Analysis of K+Hnov49
A probe was created from a fragment corresponding to nucleotides 50 to 1284 of SEQ ID NO:83 (K+Hnov49) and purified DNA fragment was labeled with [$^{32}$P]dCTP (Amersham) by the random primer method. Adult human Multiple Tissue Northern (MTM™) Blots (Clontech) were hybridized with the [$^{32}$P]-labeled fragment in ExpressHyb™

TABLE 3

| Anchor name | Adipose | Adrenal Gland | Bladder | Brain | Cerebellum | Cervix | Colon | Esophagus | Fetal Brain | Fetal Liver | Heart | HeLa Cell |
|---|---|---|---|---|---|---|---|---|---|---|---|---|
| K + Hnov1 | + | + | + | + | + | − | + | + | + | + | + | + |
| K + Hnov2 | + |   | + | + | + | + | + | + | − | + | + | + |
| K + Hnov4 |   | − | − | + | + |   | + |   | + | − | − | − |
| K + Hnov6 |   | + | + | + | + |   | + | + | + | − | + | − |
| K + Hnov9 |   | + | − | + | + |   | − |   | − | − | − | − |
| K + Hnov11 |   |   | + | + | + |   | − |   | + | + | + | + |
| K + Hnov12 | + | + | + | − | − | − |   | − | + | − | − | − |
| K + Hnov14 | − | + | + | − | + | + | + | + | + | + | − | + |
| K + Hnov15 |   | + | + | + | + |   | + |   | + | + | + | + |
| K + Hnov27 | + | + | + | + | + | + | + | + | + | + | + | + |
| K + Hnov28 | − | + | + | + | + |   | + | + | + | + | + | + |
| K + Hnov42 |   |   |   |   |   |   |   |   |   |   |   |   |
| K + Hnov44 | + | + | + | + | + | + | + | + | + | + | + | + |

| Anchor name | Kidney | Liver | Lung | Mammary Gland | Pancreas | Placenta | Prostate | Rectum | Salivary Gland | Skeletal Muscle | Skin | Small Intestine | Spleen |
|---|---|---|---|---|---|---|---|---|---|---|---|---|---|
| K + Hnov1 | + | + | + | + | + | + | + |   | + | + |   | + | + |
| K + Hnov2 | + | + | + | + | − | + | + | + | − | + | − | + |   |
| K + Hnov4 | − | − | − | + | − | − | + |   | + | + |   | + | − |
| K + Hnov6 | + | + | + | + | + | + | + | + | + | + | + | + | + |
| K + Hnov9 | + | − | − | − | + | − |   | − | + | − |   | − | + |
| K + Hnov11 | + | + | + | + | + | + | + |   | + |   |   | + |   |
| K + Hnov12 | − | + | − | − | − | − | − |   | − | − | − | − | + |
| K + Hnov14 | + | + | + | + | + | + | + | + | + | + | + | + | − |
| K + Hnov15 | + | + | + | + | + | + | + |   | + | + |   | + | + |
| K + Hnov27 | + | + | + | + | + | + | + | + | + | + | + | + | + |
| K + Hnov28 | + | + | + | + | + | + | + |   | + | + |   | + | + |
| K + Hnov42 |   |   |   |   |   |   |   |   |   |   |   |   |   |
| K + Hnov44 | + | + | + | + | + | + | + | + | + | + | + | + | − |

| Anchor name | Stomach | Testis | Thymus | Trachea | Uterus |
|---|---|---|---|---|---|
| K + Hnov1 | + | + | + | + | + |
| K + Hnov2 | + | + | + | − | + |
| K + Hnov4 | − | − | − | − | − |
| K + Hnov6 | + | + | + | + | + |
| K + Hnov9 | − | + | + | + |   |
| K + Hnov11 | + |   | − | + | + |
| K + Hnov12 | − | − | − | − | + |
| K + Hnov14 | − | + | + | + | + |
| K + Hnov15 | + | + | + | + | + |
| K + Hnov27 | + | + | + | + | + |
| K + Hnov28 | + | + | + | + | + |
| K + Hnov42 |   |   |   |   |   |
| K + Hnov44 | + | + | + | + | + |

A "+" indicates expression in the tissue, a "−" indicates no expression, and blank square indicates no data for that sample.

K+Hnov49 on Whitehead GB4 RH mapping panel:

Primer 1 (SEQ ID NO:5): 5'-CATAGCCATAGGTGAGGACT-3'
Primer 2: (SEQ ID N:6) 5'-GAGAGGAAAACAGTCTGGGC-3' solution (Clontech) for four hours, washed to a final stringency of 0.1×SSC, 0.1% SDS at 65° C. and subjected to autoradiography for 24 hours.

Analysis revealed that K+Hnov49 is expressed as an approximately 4.2 kb mRNA. Expression levels of K+Hnov49 are high in brain and liver and low in kidney tissues. No mRNA was detectable on these Northern blots for heart, skeletal muscle, colon, thymus, spleen, small intestine, placenta, lung or peripheral blood leukocytes indicating either a very low level of expression or that it is not expressed in these tissues. Expression analysis was also carried out by RT-PCR across an extended series of tissues. The results of these analyses are shown in Table 4. Primer pairs used for amplification of K+Hnov49 and 59 are the same as those used for RH mapping as indicated above.

TABLE 4

| | Adipose | Adrenal Gland | Bladder | Brain | Cerebellum | Cervix | Colon | Esophagus | Fetal Brain | Fetal Liver | Heart | HeLa Cell |
|---|---|---|---|---|---|---|---|---|---|---|---|---|
| #49 | + | + | + | + | + | + | - | + | + | - | + | + |
| #59 | - | - | - | - | - | + | - | + | - | + | + | - |

| | Kidney | Liver | Lung | Mammary Gland | Pancreas | Placenta | Prostate | Rectum | Salivary Gland | Skeletal Muscle | Skin | Small Intestine |
|---|---|---|---|---|---|---|---|---|---|---|---|---|
| #49 | + | - | + | + | - | - | + | - | + | + | - | + |
| #59 | - | + | + | + | + | - | + | + | + | - | - | + |

| | Spleen | Stomach | Testis | Thymus | Trachea | Uterus |
|---|---|---|---|---|---|---|
| #49 | - | + | + | + | - | - |
| #59 | + | + | + | + | + | + |

What is claimed is:

1. An isolated nucleic acid encoding a polypeptide comprising a subunit of an inward rectifying potassium channel, the nucleic acid comprising a nucleotide sequence of SEQ ID NO:1.

2. The isolated nucleic acid of claim 1, wherein the nucleic acid encodes a polypeptide comprising an alpha subunit of a homomeric potassium channel.

3. An expression vector encoding the nucleic acid of claim 1.

4. A host cell transfected with the expression vector of claim 3.

5. An isolated nucleic acid encoding a polypeptide comprising a subunit of an inward rectifying potassium channel, the nucleic acid hybridizing under stringent conditions, wherein the hybridization reaction is incubated at 50° C. or above in a solution comprising 0.1×SSC and washed at 55° C. in a solution comprising 1×SSC, to the complement of a nucleotide sequence of SEQ ID NO:1.

6. An isolated nucleic acid encoding a polypeptide comprising a subunit of an inward rectifying potassium channel, the polypeptide comprising an amino acid sequence of SEQ ID NO:2.

* * * * *